United States Patent
Berenson et al.

(10) Patent No.: US 10,857,152 B2
(45) Date of Patent: Dec. 8, 2020

(54) METHODS AND COMPOSITIONS FOR TREATING VIRAL OR VIRALLY-INDUCED CONDITIONS

(71) Applicants: VIRACTA THERAPEUTICS, INC., San Diego, CA (US); TRUSTEES OF BOSTON UNIVERSITY, Boston, MA (US)

(72) Inventors: Ronald J. Berenson, Mercer Island, WA (US); Douglas V. Faller, Weston, MA (US)

(73) Assignees: TRUSTEES OF BOSTON UNIVERSITY, Boston, MA (US); VIRACTA THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 15/959,482

(22) Filed: Apr. 23, 2018

(65) Prior Publication Data

US 2019/0091221 A1 Mar. 28, 2019

Related U.S. Application Data

(63) Continuation of application No. 15/335,776, filed on Oct. 27, 2016, now abandoned, which is a continuation of application No. 14/728,592, filed on Jun. 2, 2015, now abandoned, which is a continuation of application No. 13/912,637, filed on Jun. 7, 2013, now abandoned, which is a continuation of application No. 13/046,555, filed on Mar. 11, 2011, now abandoned.

(60) Provisional application No. 61/430,931, filed on Jan. 7, 2011, provisional application No. 61/313,052, filed on Mar. 11, 2010.

(51) Int. Cl.

| | |
|---|---|
| *A61K 31/506* | (2006.01) |
| *A61K 31/52* | (2006.01) |
| *A61K 31/522* | (2006.01) |
| *A61K 31/167* | (2006.01) |
| *A61K 31/19* | (2006.01) |
| *A61K 31/27* | (2006.01) |
| *A61K 31/4045* | (2006.01) |
| *A61K 31/513* | (2006.01) |
| *A61K 45/06* | (2006.01) |
| *A61K 38/12* | (2006.01) |
| *A61K 31/18* | (2006.01) |
| *A61K 9/00* | (2006.01) |
| *A61K 31/165* | (2006.01) |
| *A61K 31/473* | (2006.01) |
| *A61K 31/4402* | (2006.01) |
| *A61K 38/15* | (2006.01) |

(52) U.S. Cl.
CPC .......... *A61K 31/506* (2013.01); *A61K 9/0053* (2013.01); *A61K 31/165* (2013.01); *A61K 31/167* (2013.01); *A61K 31/18* (2013.01); *A61K 31/19* (2013.01); *A61K 31/27* (2013.01); *A61K 31/4045* (2013.01); *A61K 31/4402* (2013.01); *A61K 31/473* (2013.01); *A61K 31/513* (2013.01); *A61K 31/52* (2013.01); *A61K 31/522* (2013.01); *A61K 38/12* (2013.01); *A61K 38/15* (2013.01); *A61K 45/06* (2013.01); *Y02A 50/467* (2018.01)

(58) Field of Classification Search
CPC .... A61K 31/506; A61K 31/522; A61K 31/52; C07D 401/14; C07D 473/16
See application file for complete search history.

(56) References Cited

U.S. PATENT DOCUMENTS

| | | | |
|---|---|---|---|
| 3,471,513 | A | 10/1969 | Chinn |
| 3,904,612 | A | 9/1975 | Nagasawa |
| 4,008,323 | A | 2/1977 | Cousse |
| 4,011,336 | A | 3/1977 | Amann |
| 4,026,895 | A | 5/1977 | Tanaka |
| 4,031,243 | A | 6/1977 | Aparicio |
| 4,058,558 | A | 11/1977 | Cousse |
| 4,131,617 | A | 12/1978 | Esanu |
| 4,176,193 | A | 11/1979 | Esanu |
| 4,234,599 | A | 11/1980 | Van Scott |
| 4,613,616 | A | 9/1986 | Winston |
| 4,671,901 | A | 6/1987 | Green |
| 4,699,926 | A | 10/1987 | Abraham |
| 4,704,402 | A | 11/1987 | Abraham |
| 4,723,958 | A | 2/1988 | Pope |
| 4,731,381 | A | 3/1988 | Abraham |

(Continued)

FOREIGN PATENT DOCUMENTS

| | | |
|---|---|---|
| CA | 1209037 A | 8/1986 |
| CA | 2173976 A1 | 4/1995 |

(Continued)

OTHER PUBLICATIONS

O'Malley et al "Adenovirus-mediated gene therapy for human head and neck squamous cell cancer in a nude mouse model", Cancer Res 55(5) 1080-5 1995.

(Continued)

*Primary Examiner* — Jeffrey E. Russel
(74) *Attorney, Agent, or Firm* — Nixon Peabody LLP

(57) ABSTRACT

Provided are methods and compositions for the prevention and/or treatment of viral conditions, virally-induced conditions and inflammatory conditions. The methods can comprise administering to a subject a viral inducing agent with an antiviral agent, and optionally an additional agent. The viral inducing agent can be a HDAC inhibitor administered orally.

11 Claims, 21 Drawing Sheets

Specification includes a Sequence Listing.

(56) References Cited

U.S. PATENT DOCUMENTS

| | | | |
|---|---|---|---|
| 4,732,914 A | 3/1988 | Morton |
| 4,735,967 A | 4/1988 | Neesby |
| 4,747,825 A | 5/1988 | Linkie |
| 4,751,244 A | 6/1988 | Abraham |
| 4,766,116 A | 8/1988 | Tatsuoka |
| 4,820,711 A | 4/1989 | Pearlman |
| 4,822,821 A | 4/1989 | Perrine |
| 4,849,426 A | 7/1989 | Pearlman |
| 4,851,229 A | 7/1989 | Magruder |
| 4,853,388 A | 8/1989 | Pearlman |
| 4,880,624 A | 11/1989 | Metcalf |
| 4,894,364 A | 1/1990 | Greer |
| 4,925,873 A | 5/1990 | Friedhoff |
| 4,948,592 A | 8/1990 | Ayer |
| 4,952,560 A | 8/1990 | Kigaswa |
| 4,958,592 A | 9/1990 | Anthony |
| 4,965,251 A | 10/1990 | Stamatoyannopoulos |
| 4,997,815 A | 3/1991 | Perrine |
| 5,023,251 A | 6/1991 | Sattler |
| 5,025,029 A | 6/1991 | Perrine |
| 5,032,507 A | 7/1991 | Yu |
| 5,039,703 A | 8/1991 | Breuer |
| 5,081,124 A | 1/1992 | Hughes |
| 5,100,647 A | 3/1992 | Agus |
| 5,137,734 A | 8/1992 | Spiegelman |
| 5,185,436 A | 2/1993 | Villa |
| 5,199,942 A | 4/1993 | Gillis |
| 5,208,333 A | 5/1993 | Paul |
| 5,216,004 A | 6/1993 | Perrine |
| 5,258,367 A | 11/1993 | Bazer |
| 5,270,458 A | 12/1993 | Lemischka |
| 5,366,996 A | 11/1994 | Elford |
| 5,378,716 A | 1/1995 | Hamanaka |
| 5,403,590 A | 4/1995 | Forse |
| 5,403,867 A | 4/1995 | Okumura |
| 5,468,731 A | 11/1995 | Matsuo |
| 5,635,532 A | 6/1997 | Samid |
| 5,635,533 A | 6/1997 | Samid |
| 5,661,179 A | 8/1997 | Samid |
| 5,674,898 A | 10/1997 | Cheng |
| 5,674,912 A | 10/1997 | Martin |
| 5,679,707 A | 10/1997 | Okumura |
| 5,710,178 A | 1/1998 | Samid |
| 5,750,571 A | 5/1998 | Cheng |
| 5,780,451 A | 7/1998 | Demichele |
| 5,843,994 A | 12/1998 | Samid |
| 5,846,528 A | 12/1998 | Podsakoff |
| 5,852,056 A | 12/1998 | Samid |
| 5,858,365 A | 1/1999 | Faller |
| 5,883,123 A | 3/1999 | Tung |
| 5,912,269 A | 6/1999 | Tung |
| 5,932,545 A | 8/1999 | Henkin |
| 5,939,456 A | 8/1999 | Perrine |
| 5,945,407 A | 8/1999 | Bemis |
| 5,952,314 A | 9/1999 | Demichele |
| 6,011,000 A | 1/2000 | Perrine |
| 6,030,961 A | 2/2000 | Nudelman |
| 6,043,389 A | 3/2000 | Nudelman |
| 6,110,955 A * | 8/2000 | Nudelman | C07C 69/612 424/85.5 |
| 6,197,743 B1 | 3/2001 | Faller |
| 6,231,880 B1 | 5/2001 | Perrine |
| 6,403,647 B1 | 6/2002 | Perrine |
| 6,451,334 B2 | 9/2002 | Perrine |
| 6,677,302 B2 | 1/2004 | Faller |
| 7,192,715 B2 | 3/2007 | Harley |
| 7,265,153 B2 | 9/2007 | Faller |
| 8,618,068 B2 | 12/2013 | Perrine et al. |
| 8,993,581 B2 | 3/2015 | Perrine et al. |
| 2001/0009922 A1 | 7/2001 | Faller |
| 2001/0027215 A1 | 10/2001 | Perrine |
| 2003/0018069 A1 | 1/2003 | Faller |
| 2003/0077297 A1 | 4/2003 | Chen |
| 2005/0025839 A1 | 2/2005 | Polli |
| 2006/0074046 A1 | 4/2006 | Redkar |
| 2007/0072793 A1 | 3/2007 | Chung |
| 2007/0232528 A1 | 10/2007 | Franke |
| 2008/0015190 A1 | 1/2008 | Chakravarty |
| 2008/0027136 A1 | 1/2008 | Faller |
| 2008/0057086 A1 | 3/2008 | Etter |
| 2008/0146591 A1 | 6/2008 | Bachynsky |
| 2008/0175849 A1 | 7/2008 | Smith |
| 2008/0207590 A1 | 8/2008 | Deziel |
| 2008/0254026 A1 | 10/2008 | Long |
| 2009/0048300 A1 | 2/2009 | Chen |
| 2009/0082444 A1 | 3/2009 | Perrine |
| 2009/0130134 A1 | 5/2009 | Pancre |
| 2009/0131367 A1 | 5/2009 | Gore |
| 2009/0270497 A1 | 10/2009 | Buggy |
| 2009/0298924 A1 | 12/2009 | Davidson |
| 2010/0010010 A1 | 1/2010 | Davidson |
| 2010/0152155 A1 | 6/2010 | Moffat |
| 2010/0168004 A1 | 7/2010 | Williams |
| 2010/0280113 A1 | 11/2010 | Faller |
| 2010/0317678 A1 | 12/2010 | Moffat |
| 2011/0033946 A1 | 2/2011 | Berenson |
| 2011/0086869 A1 | 4/2011 | Perrine |
| 2011/0251149 A1 | 10/2011 | Perrine |
| 2011/0281950 A1* | 11/2011 | Baiocchi ............ A61K 31/167 514/575 |

FOREIGN PATENT DOCUMENTS

| | | |
|---|---|---|
| CA | 2303268 A1 | 12/1998 |
| EP | 0069659 B1 | 4/1986 |
| EP | 0224599 A1 | 6/1987 |
| EP | 0324574 A2 | 7/1989 |
| EP | 0350287 A2 | 1/1990 |
| EP | 0320726 A2 | 6/1990 |
| EP | 0320726 A3 | 8/1990 |
| EP | 0350287 A3 | 8/1990 |
| EP | 0324574 A3 | 12/1990 |
| EP | 0546261 A2 | 6/1993 |
| EP | 0546261 A3 | 8/1993 |
| EP | 0617966 A1 | 10/1994 |
| EP | 0371789 B1 | 1/1997 |
| EP | 22983050 A2 | 3/2011 |
| GB | 2126082 A | 3/1984 |
| JP | 61180740 A | 8/1986 |
| JP | 5089335 B2 | 12/2012 |
| WO | 1990/011071 A1 | 10/1990 |
| WO | 1991/001719 A1 | 2/1991 |
| WO | 1992/003155 A1 | 3/1992 |
| WO | 1992/004913 A1 | 4/1992 |
| WO | 1993/007866 A2 | 4/1993 |
| WO | 1993/007866 A3 | 5/1993 |
| WO | 1993/018761 A1 | 9/1993 |
| WO | 1994/004671 A1 | 3/1994 |
| WO | 1995/010271 A2 | 4/1995 |
| WO | 1995/011699 A1 | 5/1995 |
| WO | 1995/010271 A3 | 6/1995 |
| WO | 1996/002244 A1 | 2/1996 |
| WO | 1996/027369 A2 | 9/1996 |
| WO | 1996/027369 A3 | 11/1996 |
| WO | 1997/004761 A1 | 2/1997 |
| WO | 1998/004290 A2 | 2/1998 |
| WO | 1998/004290 A3 | 8/1998 |
| WO | 1998/040078 A1 | 9/1998 |
| WO | 1998/056370 A2 | 12/1998 |
| WO | 1998/056370 A3 | 4/1999 |
| WO | 2007/133653 A2 | 11/2007 |
| WO | 2007/133653 A3 | 1/2008 |
| WO | 2008/097654 A1 | 8/2008 |

OTHER PUBLICATIONS

Ormandy et al "Coordinate regulation of oestrogen and prolactin receptor expression by sodium butyrate in human breast cancer cells", Biochem Biophys Res Commun 182(2) 740-5 1992.

Osato et al "Epstein-Barr virus and gastric carcinoma", Semin Cancer Biol 7(4) 175-82 1996.

Pace et al "Short-chain fatty acid derivatives induce fetal globin expression and erythropoiesis in vivo", Blood 100(13) 4640-8 2002.

(56) References Cited

OTHER PUBLICATIONS

Pagano et al "Epstein-Barr virus: the first human tumor virus and its role in cancer", Proc Assoc Am Physicians 111(6) 573-80 1999.
Parise et al "Liquid chromatography-mass spectrometric assay for quantitation of the short-chain fatty acid, 2,2-dimethylbutyrate (NSC 741804), in rat plasma", J Chromatoqr B Analyt Technol Biomed Life Sci 862(1-2) 168-74 2008.
Partington et al "Human globin gene transcription in injected Xenopus oocytes: enhancement by sodium butyrate", EMBO J 3(12) 2787-92 1984.
Patel et al "Transcriptional activation potential of normal and tumor-associated myb isoforms does not correlate with their ability to block GCSF-induced terminal differentiation of murine myeloid precursor cells", Oncogene 13(6) 1197-208 1996.
Perez et al "Bryostatin-1 synergizes with histone deacetylase inhibitors to reactivate HIV-1 from latency", Curr HIV Res 8(6) 418-29 2010.
Perrin et al "An interleukin 2/sodium butyrate combination as immunotherapy for rat colon cancer peritoneal carcinomatosis", Gastroenterology 107(6) 1697-708 1994.
Perrine et al "A phase 1/2 trial of arginine butyrate and ganciclovir in patients with Epstein-Barr virus-associated lymphoid malignancies", Blood 109(6) 2571-8 2007.
Perrine et al "A short-term trial of butyrate to stimulate fetal-globin-gene expression in the beta-globin disorders", N Engl J Med 328(2) 81-6 1993.
Perrine et al "Benign sickle-cell anaemia", Lancet 2(7788) 1163-7 1972.
Perrine et al "Butryic acid analogues augment gamma globin gene expression in neonatal erythroid progenitors", Biochem Biophys Res Commun 148(2) 694-700 1987.
Perrine et al "Butyrate derivatives. New agents for stimulating fetal globin production in the beta-globin disorders", Am J Pediatr Hematol Oncol 16(1) 67-71 1994.
Perrine et al "Butyrate infusions in the ovine fetus delay the biologic clock for globin gene switching", Proc Natl Acad Sci USA 85(22) 8540-2 1988.
Perrine et al "Butyrate-induced reactivation of the fetal globin genes: a molecular treatment for the beta-hemoglobinopathies", Experientia 49(2) 133-7 1993.
Perrine et al "Fetal globin induction—can it cure beta thalassemia", Hematology Am Soc Hematol Educ Program 38-44 2005.
Perrine et al "HQK-1001 has additive hbf-inducing activity in combination with hydroxyurea and decitabine", 977 2009.
Perrine et al "Induction of fetal globin in beta-thalassemia: Cellular obstacles and molecular progress", Ann NY Acad Sci 1054 257-65 2005.
Perrine et al "Isobutyramide, an orally bioavailable butyrate analogue, stimulates fetal globin gene expression in vitro and in vivo", Br J Haematol 88(3) 555-61 1994.
Perrine et al "Natural history of sickle cell anemia in Saudi Arabs. A study of 270 subjects", Ann Intern Med 88(1) 1-6 1978.
Powars et al "Is there a threshold level of fetal hemoglobin that ameliorates morbidity in sickle cell anemia?", Blood 63(4) 921-6 1984.
Prasad "Butyric acid: a small fatty acid with diverse biological functions", Life Sci 27(15) 1351-8 1980.
Prochownik et al "Deregulated expression of c-myc by murine erythroleukaemia cells prevents differentiation", Nature 322(6082) 848-50 1986.
Rachmilewitz et al "The role of recombinant human erythropoietin in the treatment of thalassemia", Ann NY Acad Sci 850 129-38 1998.
Reiss et al "Induction of tumor cell differentiation as a therapeutic approach: preclinical models for hematopoietic and solid neoplasms", Cancer Treat Rep 70(1) 201-18 1986.
Rephaeli et al "Anti-leukimic effect of butyrate in-vitro and in-vivo and the development of a potent butyrate prodrug", Blood 76 115a 1990.
Reynolds "The extra pharmacopoeia", 29 1359 1989.
Rickinson et al "Epstein-Barr virus", Fields Virology 2(3) 2397-2446 1996.
Rius et al "The induction of vimentin gene expression by sodium butyrate in human promonocytic leukemia U937 cells", Exp Cell Res 188(1) 129-34 1990.
Rodgers et al "Augmentation by erythropoietin of the fetal-hemoglobin response to hydroxyurea in sickle cell disease", N Engl J Med 328(2) 73-80 1993.
Roediger et al "Selective reduction of fatty acid oxidation in colonocytes: correlation with ulcerative colitis", Lipids 25(10) 646-52 1990.
Rotili et al "Non-cancer uses of histone deacetylase inhibitors: effects on infectious diseases and beta-hemoglobinopathies", Curr Top Med Chem 9(3) 272-91 2009.
Rowe et al "Colonic short-chain fatty acids: fuel from the lumen?", Gastroenterology 103(1) 336-8 1992.
Rowinsky et al "Prolonged infusion of hexamethylene bisacetamide: a phase I and pharmacological study", Cancer Res 47(21) 5788-95 1987.
Roychowdhury et al "Selective efficacy of depsipeptide in a xenograft model of Epstein-Barr virus-positive lymphoproliferative disorder", J Natl Cancer Inst 96(19) 1447-57 2004.
Rubenstein et al "A pilot clinical trial of oral sodium 4-phenylbutyrate (Buphenyl) in deltaF508-homozygous cystic fibrosis patients: partial restoration of nasal epithelial CFTR function", Am J Respir Crit Care Med 157(2) 484-90 1998.
Rubenstein et al "In vitro pharmacologic restoration of CFTR-mediated chloride transport with sodium 4-phenylbutyrate in cystic fibrosis epithelial cells containing delta F508-CFTR", J Clin Invest 100(10) 2457-65 1997.
Evans et al "A population-based case-control study of EBV and other viral antibodies among persons with Hodgkin's disease and their siblings", Int J Cancer 34(2) 149-157 1984.
Faller et al "Arginine butyrate-induced susceptibility to ganciclovir in an epstein-barr virus (EBV) associated lymphoma", Blood 86(10)(1) 342a 1995.
Faller et al "Arginine butyrate-induced susceptibility to ganciclovir in an epstein-barr virus (EBV)-associated lymphomas", Proceedings of the American Association for Cancer Research 37 411-12 1996.
Faller et al "Phase I/II trial of arginine butyrate to induce viral tk gene expression in epstein-barr virus (EBV)-associated lymphomas", Proc Am Assn for Cancer Research 41 544 2000.
Fathallah et al "Neonatal invasive candidiasis in Tunisian hospital: incidence, risk factors, distribution of species and antifungal susceptibility", Mycoses 55(6) 493-500 2012.
Faucitano et al "Reaction of gases with irradiated organic solids. I. preliminary results on propionamide, n-butyramide, and isobutyramide", Ric Sci 37(12) 1149-55 1967.
Feng et al "Valproic acid enhances the efficacy of chemotherapy in EBV-positive tumors by increasing lytic viral gene expression", Cancer Res 66(17) 8762-9 2006.
Fibach et al "Enhanced fetal hemoglobin production by phenylacetate and 4-phenylbutyrate in erythroid precursors derived from normal donors and patients with sickle cell anemia and beta-thalassemia", Blood 82(7) 2203-9 1993.
Flyer et al "Retrovirus-induced changes in major histocompatibility complex antigen expression influence susceptibility to lysis by cytotoxic T lymphocytes", J Immunol 35(4) 2287-92 1985.
Forrester et al "Molecular analysis of the human beta-globin locus activation region", Proc Natl Acad Sci USA 86(14) 5439-43 1989.
Foss et al "Biomodulatory effects of butyric-acid derivatives on leukemia and lymphoma-cells" Blood 82(10) 564a 1993.
Franco et al "The effect of fetal hemoglobin on the survival characteristics of sickle cells", Blood 108(3) 1073-6 2006.
Franke et al "[Experiences with alpha-aminoisobutyric acid in the treatment of wounds]", Zentralbl Chir 79(18) 769-76 1954.
Fraser et al "Each hypersensitive site of the human beta-globin locus control region confers a different developmental pattern of expression on the globin genes", Genes Dev 7(1) 106-13 1993.
Fritsch et al "Characterisation of deletions which affect the expression of fetal globin genes in man", Nature 279(5714) 589-603 1979.

(56) References Cited

OTHER PUBLICATIONS

Fucharoen et al "Alpha- and beta-thalassemia in Thailand", Ann NY Acad Sci 850 412-4 1998.
Fucharoen et al "Clinical and hematologic aspects of hemoglobin E beta-thalassemia", Curr Opin Hematol 7(2) 106-12 2000.
Fucharoen et al "Hemoglobinopathies in Southeast Asia", Hemoglobin 11(1) 65-88 1987.
Fucharoen et al "Thalassemia in SouthEast Asia: problems and strategy for prevention and control", Southeast Asian J Trop Med Public Health 23(4) 647-55 1992.
Gabbianeri et al "Granulocyte-macrophage colony-stimulating factor reactivates fetal hemoglobin synthesis in erythroblast clones from normal adults", Blood 74(8) 2657-67 1989.
Garre et al "Regulation of acetylcholinesterase expression in the K-562 cell line", Cancer Res 44(9) 3749-51 1984.
Garsetti et al "Butyric acid-induced differentiation of HL-60 cells increases the expression of a single lysophospholipase", Biochem J 288 (Pt 3) 831-7 1992.
Gaudet et al :Differential regulation of arylamine and arylalkylamine N-acetyltransferases in human retinoblastoma (Y-79) cells, Neurochem Int 22(3) 271-5 1993.
Gerharz et al "Modulation of invasive potential in different clonal subpopulations of a rat rhabdomyosarcoma cell line (BA-HAN-1) by differentiation induction", Clin Exp Metastasis 11(1) 55-67 1993.
Ghanayem et al "Structure-activity relationships for the in vitro hematotoxicity of N-alkoxyacetic acids, the toxic metabolites of glycol ethers", Chem Biol Interact 70(3-4) 339-52 1989.
Ghosh et al "Short, discontinuous exposure to butyrate effectively sensitizes latently EBV-infected lymphoma cells to nucleoside analogue antiviral agents", Blood Cells Mol Dis 38(1) 57-65 2007.
Gilbert et al "A phase I dose escalation and bioavailability study of oral sodium phenylbutyrate in patients with refractory solid tumor malignancies", Clin Cancer Res 7(8) 2292-300 2001.
Ginder et al "Activation of a chicken embryonic globin gene in adult erythroid cells by 5-azacytidine and sodium butyrate", Proc Natl Acad Sci USA 81(13) 3954-8 1984.
Gladwin "Unraveling the hemolytic subphenotype of sickle cell disease", Blood 106(9) 2925-6 2005.
Gladwin et al "Pulmonary hypertension as a risk factor for death in patients with sickle cell disease", N Engl J Med 350(9) 886-95 2004.
Glaser "HDAC inhibitors: clinical update and mechanism-based potential", Biochem Pharmacol 74(5) 659-71 2007.
Glaser et al "Epstein-Barr virus-associated Hodgkin's disease: epidemiologic characteristics in international data", Int J Cancer 70(4) 375-82 1997.
Golub et al "Induction of dormant HIV-1 by sodium butyrate: involvement of the TATA box in the activation of the HIV-1 promoter", AIDS 5(6) 663-8 1991.
Gradoville et al "Protein kinase C-independent activation of the Epstein-Barr virus lytic cycle", J Virol 76(11) 5612-26 2002.
Gredmark et al "Active cytomegalovirus replication in patients with coronary disease", Scand Cardiovasc J 41(4) 230-4 2007.
Greenspan et al "Replication of Epstein-Barr virus within the epithelial cells of oral "hairy" leukoplakia, an AIDS-associated lesion", N Engl J Med 313(25) 1564-71 1985.
Gross et al "B cell lymphoproliferative disorders following hematopoietic stem cell transplantation: risk factors, treatment and outcome", Bone Marrow Transplant 23(3) 251-8 1999.
Grossi et al "Effects of monosaccharide esters of butyric acid on the synthesis of hemoglobin and chain in an erythroleukemia cell line", Blood 86(10) 2579 1995.
Grufferman et al "Hodgkin's disease in siblings", N Engl J Med 296(5) 248-50 1997.
Guilbaud et al "Effects of differentiation-inducing agents on maturation of human MCF-7 breast cancer cells", J Cell Physiol 145(1) 162-72 1990.
Gum et al "Effects of sodium butyrate on human colonic adenocarcinoma cells. Induction of placental-like alkaline phosphatase", J Biol Chem 262(3) 1092-7 1987.

Hanh et al "Therapeutic outcome of Epstein-Barr virus positive T/NK cell lymphoma in the upper aerodigestive tract", Yonsei Med J 43(2) 175-82 2002.
Hanto et al "Epstein-Barr virus (EBV) induced polyclonal and monoclonal B-cell lymphoproliferative diseases occurring after renal transplantation. Clinical, pathologic, and virologic findings and implications for therapy", Ann Surg 198(3) 356-69 1983.
Harabuchi et al "Epstein-Barr virus in nasal T-cell lymphomas in patients with lethal midline granuloma", Lancet 335 (8682) 128-30 1990.
Harig et al "Treatment of diversion colitis with short-chain-fatty acid irrigation", N Engl J Med 320(1) 23-8 1989.
Henle "Epstein-Barr virus and human malignancies", Adv Virol Oncol 5 201-238 1985.
Henle et al "Relation of Burkitt's tumor-associated herpes-ytpe virus to infectious mononucleosis", Proc Natl Acad Sci USA 59(1) 94-101 1968.
Herbst et al "Epstein-Barr virus latent membrane protein expression in Hodgkin and Reed-Sternberg cells", Proc Natl Acad Sci USA 88(11) 4766-70 1991.
Ho et al "Presence of Epstein-Barr virus DNA in nasal lymphomas of B and 'T' cell type", Hemtol Oncol 8(5) 271-81 1990.
Hock et al "Retrovirus-mediated transfer and expression of drug resistance genes in human haematopoietic progenitor cells", Nature 320(6059) 275-7 1986.
Burns et al "Butyrate induces selective transcriptional activation of a hypomethylated embryonic globin gene in adult erythroid cells", Blood 72(5) 1536-42 1988.
Byrd et al "Two types of transglutaminase in the PC12 pheochromocytoma cell line. Stimulation by sodium butyrate", J Biol Chem 262(24) 11699-709 1987.
Callery et al "Identification of metabolites of the cell-differentiating agent hexamethylene bisacetamide in humans", Cancer Res 46(10) 4900-3 1986.
Canceill et al "Stereochemistry of reduction of beta-keto esters, beta-keto amides and beta-keto nitriles by hydrides" Bulletin de la Societe Chimique de France (6) 2180-7 1970.
Caruso et al "Regression of established macroscopic liver metastases after in situ transduction of a suicide gene", Proc Natl Acen Sci USA 90(15) 7024-8 1993.
Castaneda et al "Enhancement of growth and survival and alterations in Bcl-family proteins in beta-thalassemic erythroid progenitors by novel short-chain fatty acid derivatives", Blood Cells Mol Dis 35(2) 217-26 2005.
Chang et al "An analysis of fetal hemoglobin variation in sickle cell disease: the relative contributions of the X-linked factor, beta-globin haplotypes, alpha-globin gene number, gender, and age", Blood 85(4) 1111-7 1995.
Chany et al "Antitumor effect of arginine butyrate in conjunction with *Corynebacterium parvum* and interferon", Int J Cancer 30(2) 489-93 1982.
Chany et al "Effect of coordinated therapeutic assays using *C. parvum*, interferon and arginine butyrate on spontaneous disease and survival of AKR mice", Int J Cancer 32(3) 379-383 1983.
Charache et al "Hydroxyurea-induced augmentation of fetal hemoglobin production in patients with sickle cell anemia", Blood 69(1) 109-16 1987.
Charache et al "Treatment of sickle cell anemia with 5-azacytidine results in increased fetal hemoglobin production and is associated with nonrandom hypomethylation of DNA around the gamma-delta-beta-globin gene complex", Proc Natl Acad Sci USA 80(15) 4842-6 1983.
Chen et al "Tributyrin: a prodrug of butyric acid for potential clinical application in differentiation therapy", Cancer Res 54(13) 3292-9 1994.
Cheng et al "Functional activation of the cystic fibrosis trafficking mutant delta F508-CFTR by overexpression", AM J Physiol 268(4 PT 1) L615-24 1995.
Chu et al "In situ detection of Epstein-Barr virus in breast cancer", Cancer Lett 124(1) 53-7 1998.

(56) References Cited

OTHER PUBLICATIONS

Chung et al "A novel approach for nasopharyngeal carcinoma treatment uses phenylbutyrate as a protein kinase C modulator: implications for radiosensitization and EBV-targeted therapy", Clin Cancer Res 6(4) 1452-8 2000.
Clegg et al "Abnormal human haemoglobins. Separation and characterization of the alpha and beta chains by chromatography, and the determination of two new variants, hb Chesapeak and hb J (Bangkok)", J Mol Biol 19(1) 91-108 1966.
Coates et al "Persistence of Epstein-Barr virus in Reed-Sternberg cells throughout the course of Hodgkin's disease", J Pathol 164(4) 291-7 1991.
Cohen et al "Thalassemia", Hematology Am Soc Hematol Educ Program 14-34 2004.
Collins et al "Safety of the calcium antagonist lacidipine evaluated from a phase III-IV trial database", J Hypertens Suppl 14(2) S15-20 1996.
Colombo "Natural history and pathogenesis of hepatitis C virus related hepatocellular carcinoma", J Hepatol 31 Suppl 1 25-30 1999.
Constantaoulakis et al "n the induction of fetal hemoglobin by butyrates: in vivo and in vitro studies with sodium butyrate and comparison of combination treatments with 5-AzaC and AraC", Blood 74(6) 1963-71 1989.
Cook et al "Effect of sodium butyrate on alpha-fetoprotein gene expression in rat hepatoma cells in vitro", Cancer Res 45(7) 3215-9 1985.
Copeland et al "Mast cell growth factor maps near the steel locus on mouse chromosome 10 and is deleted in a number of steel alleles", Cell 63(1) 175-83 1990.
Cossman et al "Induction of differentiation in a case of common acute lymphoblastic leukemia", N Engl J Med 307(20) 1251-4 1982.
Countryman et al "Histone hyperacetylation occurs on promoters of lytic cycle regulatory genes in Epstein-Barr virus-infected cell lines which are refractory to disruption of latency by histone deacetylase inhibitors", J Virol 82(10) 4706-19 2008.
Curtis et al "Risk of lymphoproliferative disorders after bone marrow transplantation: a multi-institutional study", 94(7) 2208-16 1999.
Dakshinamurty et al "Ternary liquid equilibrium systems ethanol-water-methyl isobutyl carbinol and acetic acid-water-ethyl butyrate", Journal of Chemical and Engineering Data 17(3) 379-383 1972.
Daniel "Pharmacokinetic study of butyric acid administered in vivo as sodium and arginine butyrate salts", Clin Chim Acta 181(3) 255-63 1989.
Dantchev et al "[Behavior of certain pyrimidine compounds, of fumaric acid and of maleic acid in regard to the protection of erythrocytes of rabbits poisoned by phenylhydrazine]", C R Acad Scu Hebd Seances Acad Sci D 264(11) 1467-70 1967.
De Bruin et al "Detection of Epstein-Barr virus nucleic acid sequences and protein in nodal T-cell lymphomas: relation between latent membrane protein-1 positivity and clinical course", Histopathology 23(6) 509-18 1993.
De Bruin et al "Presence of Epstein-Barr virus in extranodal T-cell lymphomas: differences in relation to site", Blood 83(6) 1612-8 1994.
De Vente et al "Effects of adenosine and adenosine-analogs on adenylate cyclase activity in the rat adipocyte plasma membrane: comparison of the properties of the enzyme with $Mn^{2+}$ and $Mg^{2+}$ as divalent cations", Mol Cell Biochem 40(2) 65-73 1981.
Dimaio et al "Directed enzyme pro-drug gene therapy for pancreatic cancer in vivo", Surgery 116(2) 205-13 1994.
Dokmanovic et al "Histone deacetylase inhibitors: overview and perspectives", 5(10) 981-9 2007.
Donaldson et al "Cytotoxicity of the anticancer agents cisplatin and taxol during cell proliferation and the cell cycle", Int J Cancer 57(6) 847-55 1994.
Douillard et al "Phase I trial of interleukin-2 and high-dose arginine butyrate in metastatic colorectal cancer", Cancer Immunol Immunother 49(1) 56-61 2000.
Dover et al "Fetal hemoglobin levels in sickle cell disease and normal individuals are partially controlled by an X-linked gene located at Xp22.2", Blood 80(3) 816-24 1992.
Dover et al "Hydroxyurea induction of hemoglobin F production in sickle cell disease: relationship between cytotoxicity and F cell production", Blood 67(3) 735-8 1986.
Dover et al "Induction of fetal hemoglobin production in subjects with sickle cell anemia by oral sodium phenylbutyrate", Blood 84(1) 339-43 1994.
Egorin et al "Phase I clinical and pharmacokinetic study of hexamethylene bisacetamide (NSC 95580) administered as a five-day continuous infusion", Cancer Res 47(2) 617-23 1987.
El Rassi et al "Beta-thalassemia intermedia: an overview", Pediatr Ann 37(5) 322-8 2008.
Elaut et al "The pharmaceutical potential of histone deacetylase inhibitors", Curr Pharm Des 13(25) 2584-620 2007.
El-Beshlawy et al "Fetal globin induction in beta-thalassemia", Hemoglobin 33 Suppl1: S197-203 2009.
Ellis et al "Synthetic human beta-globin 5'HS2 constructs function as locus control regions only in multicopy transgene concatamers", EMBO J 12(1) 127-34 1993.
El-Nawawy et al "Organic pesticides. II. (arylthio) acetic acids, (arylenedithio) diacetic acids, and several of their s-alkylisothiuronium salts", Alexandria J Agr Res 16(2) 173-184 1970.
Endo et al "Differential induction of adult and fetal globin gene expression in the human CML cell subline KU-812F/33", J Biochem 115(3) 540-4 1994.
EP 10184726 Search Report dated Jan. 20, 2011.
European office action dated Aug. 11, 2010 for Application No. 6021311.3.
European search report dated Jun. 16, 2005 for Application No. 94930734.2.
European search report dated Jun. 9, 2009 for Application No. 6021311.3.
Hoessly et al "Factors responsible for variable reported lineages of HL-60 cells induced to mature with butyric acid", Cancer Res 49(13) 3594-7 1989.
Hoey et al "Molecular cloning and functional analysis of *Drosophila* TAF110 reveal properties expected of coactivators", Cell 72(2) 247-60 1993.
Hoffman LaRoche Monograph pp. 1-10 (2007).
HSU et al "Epstein-barr virus-associated malignancies: epidemiologic patterns and etiologic implications", Crit Rev Oncol Hematol 34(1) 27-53 2000.
Huang et al "The hematopoietic growth factor KL is encoded by the SI locus and is the ligand of the c-kit receptor, the gene product of the W locus", Cell 63(1) 225-33 1990.
Huber et al "In vivo antitumor activity of 5-fluorocytosine on human colorectal carcinoma cells genetically modified to express cytosine deaminase", Cancer Res 53(19) 4619-26 1993.
Huber et al "Metabolism of 5-fluorocytosine to 5-fluorouracil in human colorectal tumor cells transduced with the cytosine deaminase gene: significant antitumor effects when only a small percentage of tumor cells express cytosine deaminase", Proc Natl Acad Sci USA 91(17) 8302-6 1994.
Hurford et al "Gene therapy of metastatic cancer by in vivo retroviral gene targeting", Nat Genet 10(4) 430-5 1995.
Ikuta et al "Alterations in protein-DNA interactions in the gamma-globin gene promoter in response to butyrate therapy", Blood 92(8) 2924-33 1998.
Inati et al "Beta-thalassemia: the Lebanese experience", Clin Lab Haematol 28(4) 217-27 2006.
International search report and written opinion dated Oct. 25, 2011 for PCT Application No. US11/28214.
International search report and written opinion dated Dec. 15, 2010 for PCT Application No. US10/50191.
International search report dated Jan. 2, 1995 for PCT Application No. US94/11565.
International search report dated Oct. 12, 2000 for PCT Application No. US1999/03014.

(56) References Cited

OTHER PUBLICATIONS

International search report dated Mar. 2, 2010 for PCT Application No. US2009/069035.
International search report dated Sep. 30, 1996 for PCT Application No. US1996/02907.
Jaffe et al "Classification of cytotoxic T-cell and natural killer cell lymphomas", Semin Hematol 40(3) 175-84 2003.
Jane et al "Hemoglobin switching in man and chicken is mediated by a heteromeric complex between the ubiquitous transcription factor CP2 and a developmentally specific protein", EMBO J 14(1) 97-105 1995.
Jiang et al "cMYB is involved in the regulation of fetal hemoglobin production in adults", Blood 108(3) 1077-83 2006.
Jiwa et al "Epstein-Barr virus DNA in Reed-Sternberg cells of Hodgkin's disease is frequently associated with CR2 (EBV receptor) expression", Histopathology 21(1) 51-7 1992.
Johansson et al "Epstein-Barr virus (EBV)-associated antibody patterns in malignant lymphoma and leukemia. I. Hodgkin's disease", Int J Cancer 6(3) 450-62 1970.
Johnson "L-carnitine for treatment of distal ulcerative colitis", Gastroenterology 103(5) 1709-10 1992.
Jones et al "Sodium valproate in combination with ganciclovir induces lysis of EBV-infected lymphoma cells without impairing EBV-specific T-cell immunity", Int J Lab Hematol 32(1 PT 1) 169-74 2010.
Jones et al "T-cell lymphomas containing Epstein-Barr viral DNA in patients with chronic Epstein-Barr virus infections", N Engl J Med 318(12) 733-41 1988.
Kanavaros et al "Nasal T-cell lymphoma: a clinicopathologic entity associated with peculiar phenotype and with Epstein-Barr virus", Blood 81(10) 2688-95 1993.
Karlsson et al "Developmental regulation of human globin genes", Annu Rev Biochem 54 1071-108 1985.
Kato et al "Deconstructing sickle cell disease: reappraisal of the role of hemolysis in the development of clinical subphenotypes", Blood Rev 21(1) 37-47 2007.
Kattamis "Treatment of thalassemia with hydroxyurea: an indispensable alternative therapy", J Pediatr Hematol Oncol 29(11) 729-30 2007.
Kawa "Epstein-Barr virus—associated diseases in humans", Int J Hematol 71(2) 108-17 2000.
Keedy et al "A limited group of class I histone deacetylases acts to repress human immunodeficiency virus type 1 expression", J Virol 83(10) 4749-56 2009.
Kim et al "Modification of thermosensitivity of HeLa cells by sodium butyrate, dibutyryl cyclic adenosine 3':5'-monophosphate, and retinoic acid", Cancer Res 44(2) 697-702 1984.
Kirk et al "Arginine stimulates wound healing and immune function in elderly human beings", Surgery 114(2) 155-9 1993.
Kleer et al "Detection of Epstein-Barr virus in rapidly growing fibroadenomas of the breast in immunosuppressed hosts", Mod Pathol 15(7) 759-64 2002.
Koeffler "Induction of differentiation of human acute myelogenous leukemia cells: therapeutic implications", Blood 62(4) 709-21 1983.
Konstan et al "Effect of high-dose ibuprofen in patients with cystic fibrosis", N Engl J Med 332(13) 848-54 1995.
Korbjuhn et al "Frequent latent Epstein-Barr virus infection of neoplastic T cells and bystander B cells in human immunodeficiency virus-negative European peripheral pleomorphic T-cell lymphomas", Blood 82(1) 217-23 1993.
Koren et al "Response to hydroxyurea therapy in beta-thalassemia", Am J Hematol 83(5) 366-70 2008.
Krantis et al "Augmentation of cysteamine-induced ulceration of rat duodenum by systemically administered gamma-aminobutyric acid (GABA)", Dig Dis Sci 34(8) 1211-6 1989.
Kwong et al "Natural killer cell lymphoma/leukemia: pathology and treatment", Hematol Oncol 15(2) 71-9 1997.

Labie et al "Common haplotype dependency of high G gamma-globin gene expression and high Hb F levels in beta-thalassemia and sickle cell anemia patients", Proc Natl Acad Sci USA 82(7) 2111 1985.
Langdon et al "Effect of sodium butyrate and other differentiation inducers on poorly differentiated human ovarian adenocarcinoma cell lines", Cancer Res 48(21) 6161 1988.
Lea et al "Butyramide and monobutyrin: growth inhibitory and differentiating agents", Anticancer Res 13(1) 145-9 1993.
Leavitt et al "Butyric acid suppression of the in vitro neoplastic state of Syrian hamster cells", Nature 271(5642) 262-5 1978.
Leder et al "Differentiation of erythroleukemic cells in the presence of inhibitors of DNA synthesis", Science 190 (4217) 893-4 1975.
Lee et al "Essential role of PKCdelta in histone deacetylase inhibitor-induced Epstein-Barr virus reactivation in nasopharyngeal carcinoma cells", J Gen Virol 89(Pt 4) 878-83 2008.
Lee et al "The association of Epstein-Barr virus with smooth-muscle tumors occurring after organ transplantation", N Engl J Med 332(1) 19-25 1995.
Leoncini et al "Epstein-Barr virus and gastric cancer: data and unanswered questions", Int J Cancer 53(6) 898-901 1993.
Letvin et al "Augmentation of fetal-hemoglobin production in anemic monkeys by hydroxyurea", N Engl J Med 310 (14) 869-73 1984.
Ley et al "5-Azacytidine increases gamma-globin synthesis and reduces the proportion of dense cells in patients with sickle cell anemia", Blood 62(2) 370-80 1983.
Ley et al "5-azacytidine selectively increases gamma-globin synthesis in a patient with beta+ thalassemia", N Engl J Med 307(24) 1469-75 1982.
Liakopoulou et al "Induction of fetal hemoglobin by propionic and butyric acid derivatives: correlations between chemical structure and potency of Hb F induction", Blood Cells Mol Dis 29(1) 48-56 2002.
Liakopoulou et al "Stimulation of fetal hemoglobin production by short chain fatty acids", Blood 86(8) 3227-35 1995.
Lilbert et al "Common vascular changes in the jugular vein of saline controls in continuous infusion in the beagle dog", Toxicol Pathol 32(6) 694-700, 2004.
Little et al "Metabolic persistence of fetal hemoglobin", Blood 85(7) 1712-8 1995.
Lokeshwar et al "Enhancement of radiation response of prostatic carcinoma by taxol: therapeutic potential for late-stage malignancy", Anticancer Res 15(1) 93-8 1995.
Magrath et al "Breast cancer: a new Epstein-Barr virus-associated disease?", J Natl Cancer Inst 91(16) 1349-50 1999.
Maia et al "Chronic, active Epstein-Barr virus infection", Curr Opin Hematol 7(1) 59-63 2000.
Mankidy et al "Short-chain fatty acids induce gamma-globin gene expression by displacement of a HDAC3-NCoR repressor complex", Blood 108(9) 3179-86 2006.
Mares et al "Evaluation of gas chromatograph packings for the separation of butyric acid from serum-catalyzed hydrolysis of ethyl butyrate", Anal Biochem 90(2) 824-8 1978.
Matalon et al "The histone deacetylase inhibitor ITF2357 decreases surface CXCR4 and CCR5 expression on CD4 (+) T-cells and monocytes and is superior to valproic acid for latent HIV-1 expression in vitro", J Acquir Immune Defic Syndr 54(1) 1-9 2010.
Mathias et al "Ineffective erythropoiesis in beta-thalassemia major is due to apoptosis at the polychromatophilic hormoblast stage", Exp Hematol 28(12) 1343-53 2000.
Maziarz et al "Distinct effects of interferon-gamma and MHC class I surface antigen levels on resistance of the K562 tumor cell line to natural killer-mediated lysis", 130(2) 329-38 1990.
Maziarz et al "The regulation of exogenous and endogenous class I MHC genes in a human tumor cell line, K562", Mol Immunol 27(2) 135-42 1990.
McCafferty et al "Inhibition of butyric acid-induced colitis in mice by 16,16-dimethyl prostaglandin E2", Agents Actions C79-81 1992.
McCafferty et al "Short chain fatty acid-induced colitis in mice", Int J Tissue React 11(4) 165-8 1989.
McClain et al "Association of Epstein-Barr virus with leiomyosarcomas in young people with AIDS", N Engl J Med 332(1) 12-8 1995.

(56) References Cited

OTHER PUBLICATIONS

McDonagh et al "The upstream region of the human gamma-globin gene promoter. Identification and functional analysis of nuclear protein binding sites", J Biol Chem 266(18) 11965-74 1991.
McGovern HFD-570 pp. 123-131 (1998).
Medeiros et al "Localization of Epstein-Barr viral genomes in angiocentric immunoproliferative lesions", Am J Surg Pathol 16(5) 439-47 1992.
Meijer et al "Epstein-Barr virus and human T-cell lymphomas", Semin Cancer Biol 7(4) 191-6 1996.
Migliaccio et al "Influence of recombinant hematopoietins and of fetal bovine serum on the globin synthetic pattern of human BFUe", Blood 76(6) 1150-7 1990.
Miller et al "Antibodies to butyrate-inducible antigens of Kaposi's sarcoma-associated herpesvirus in patients with HIV-1 infection", N Engl J Med 334(20) 1292-7 1996.
Miller et al "Clinical pharmacology of sodium butyrate in patients with acute leukemia", Eur J Cancer Clin Oncol 23(9) 1283-7 1987.
Miller et al "Influence of steel factor on hemoglobin synthesis in sickle cell disease", Blood 79(7) 1861-8 1992.
Miller et al "Toxicity of methoxyacetic acid in rats", Fundam Appl Toxicol 2(4) 158-60 1982.
Modell et al "Epidemiology of haemoglobin disorders in Europe: an overview", Scand J Clin Lab Invest 67(1) 39-69 2007.
Moffat et al "Discovery of 2-(6-{[(6-fluoroquinolin-2-yl)methyl]amino}bicyclo[3.1.0]hex-3-yl)-N-hydroxypyrimidine-5-carboxamide (CHR-3996), a class I selective orally active histone deacetylase inhibitor", J Med Chem 53(24) 8663-78 2010.
Moi et al "Synergistic enhancement of globin gene expression by activator protein-1-like proteins", Proc Natl Acad Sci USA 87(22) 9000-4 1990.
Morita et al "Effect of sodium butyrate on alkaline phosphatase in HRT-18, a human rectal cancer cell line", Cancer Res 42(11) 4540-5 1982.
Mueller et al "Hodgkin's disease and Epstein-Barr virus. Altered antibody pattern before diagnosis", N Engl J Med 320(11) 689-95 1989.
Mueller et al "In vivo footprinting of a muscle specific enhancer by ligation mediated PCR", Science 246(4931) 780-6 1989.
Nagai et al "Studies on the synergistic action and anti-ulcerous activity of cortisone-GABOB", Arzneimittelforschung 21(1) 96-7 1971.
Nagel et al "F reticulocyte response in sickle cell anemia treated with recombinant human erythropoietin: a double-blind study", Blood 81(1) 9-14 1993.
Nagel et al "Structural bases of the inhibitory effects of hemoglobin F and hemoglobin A2 on the polymerization of hemoglobin S", Proc Natl Acad Sci USA 76(2) 670-2 1979.
Naguib et al "Effects of N,N-dimethylformamide and sodium butyrate on enzymes of pyrimidine metabolism in cultured human tumor cells", Leuk Res 11(10) 855-61 1987.
Nathan "Regulation of fetal hemoglobin synthesis in the hemoglobinopathies", Ann NY Acad Sci 445 177-87 1985.
Newman et al "Induction of the insulin receptor and other differentiation markers by sodium butyrate in the Burkitt lymphoma cell, Raji", Biochem Biophys Res Commun 161(1) 101-6 1989.
Newman et al "Sodium n-butyrate enhancement of prostaglandin D2 antitumor efficacy", Biochem Pharmacol 34(20) 3771-4 1985.
Ney et al., "Purification of the human NF-E2 complex: cDNA cloning of the hematopoietic cell-specific subunit and evidence for an associated partner", Mol Cell Biol 13(9) 5604-5612 (1993).
Nguyen et al., "Chemical targeting of the innate antiviral response by histone deacetylase inhibitors renders refractory cancers sensitive to viral oncolysis", Proc Natl Acad Sci USA 105(39) 14981-14986 (2008).
Niedobitek "The role of Epstein—Barr virus in the pathogenesis of Hodgkin's disease", Ann Oncol 7(Suppl 4) 11-7 1996.
Niedobitek et al "Epstein-Barr virus gene expression in Hodgkin's disease", Blood 78(6) 1628-30 1991.

Nienhuis et al "Pharmacological manipulation of fetal hemoglobin synthesis in patients with severe beta-thalassemia", Ann NY Acad Sci 445 198-211 1985.
Nisli et al "Recombinant human erythropoietin trial in thalassemia intermedia", J Trop Prediatr 42(6) 330-4 1996.
Noguchi et al "Inhibition of sickle hemoglobin gelation by amino acids and related compounds", Biochemistry 17(25) 5455-9 1978.
Nioguchi et al "Levels of fetal hemoglobin necessary for treatment of sickle cell disease", N Engl J Med 318(2) 96-9 1988.
Novogrodsky et al "Effect of polar organic compounds on leukemic cells. Butyrate-induced partial remission of acute myelogenous leukemia in a child", Cancer 51(1) 9-14 1983.
Nudel et al "Differential effects of chemical inducers on expression of beta globin genes in murine erythroleukemia cells", Proc Natl Acad Sci USA 74(3) 1100-4 1977.
Nudelman et al "Novel anticancer prodrugs of butyric acid. 2", J Med Chem 35(4) 687-94 1992.
Oldfield et al "Gene therapy for the treatment of brain tumors using intra-tumoral transduction with the thymidine kinase gene and intravenous ganciclovir", Hum Gene Ther 4(1) 39-69 1993.
Abbott et al., "Quantitative structure-anticonvulsant activity relationships of valproic acid, related carboxylic acids and tetrazoles", Neuropharmacology 27(3) 287-294 (1988).
Abe et al., "Sodium butyrate induction of milk-related antigens in human MCF-7 breast carcinoma cells", Cancer Res 44(10) 4574-4577 (1984).
Abraham et al "Synthesis of the minor fetal hemoglobin Fic in colonies of erythropoietic precursors isolated from human umbilical cord blood", Am J Hematol 12(3) 207-2013 (1982).
Abraham et al., "Design, synthesis, and testing of potential antisickling agents. 1. Halogenated benzyloxy and phenoxy acids", J Med Chem 25(9) 1015-1017 (1982).
Al-Khatti et al., "Erythropoietin stimulates F-reticulocyte formation in sickle cell anemia", Trans Assoc Am Physicians 101: 54-61 (1988).
Anderson et al., "Molecular cloning of mast cell growth factor, a hematopoietin that is active in both membrane bound and soluble forms", cell 63(1) 235-243 (1990).
Andrews et al "Erythroid transcription factor NF-E2 is a haematopoietic-specific basic-leucine zipper protein", Nature 362(6422) 722-8 (1993).
Andrews et al., "A rapid micropreparation technique for extraction of DNA-binding proteins from limiting numbers of mammalian cells", Nucleic Acids Res 19(9) 2499 (1991).
Angasiniotis et al., "Global epidemiology of hemoglobin disorders", Ann N Y Acad Sci 850: 251-269 (1998).
Antoni et al., "NF-kappa B-dependent and -independent pathways of HIV activation in a chronically infected T cell line", Virology 202(2) 684-694 (1994).
Archin et al., "Antiretroviral intensification and valproic acid lack sustained effect on residual HIV-1 viremia or resting CD4+ cell infection", PLoS One 5(2) e9390 (2010).
Archin et al., "Expression of latent HIV induced by the potent HDAC inhibitor suberoylanilide hydroxamic acid", AIDS Res Hum Retrovirus 25(2) 207-212 (2009).
Archin et al., "Expression of latent human immunodeficiency type 1 is induced by novel and selective histone deacetylase inhibitors", AIDS 23(14) 1799-1806 (2009).
Archin et al., "Valproic acid without intensified antiviral therapy has limited impact on persistent HIV infection of resting CD4+ T cells", AIDS 22(1) 1131-1135 (2008).
Armstrong et al., "Criteria for the definition of Epstein-Barr virus association in Hodgkin's disease", Leukemia 6(9) 869-874 (1992).
Atweh et al., "Pharmacological induction of fetal hemoglobin in sickle cell disease and beta-thalassemia", Semin Hematol 38(4) 367-373 (2001).
Atweh et al., "Sustained induction of fetal hemoglobin by pulse butyrate therapy in sickle cell disease", Blood 93(6) 1790-1797 (1999).
Augeron et al., "Emergence of permanently differentiated cell clones in a human colonic cancer cell line in culture after treatment with sodium butyrate", Cancer Res 44(9) 3961-3969 (1984).

(56) References Cited

OTHER PUBLICATIONS

Barbul et al., "Arginine enhances wound healing and lymphocyte immune responses in humans", Surgery 108(2) 331-336 (1990).
Barker et al., "The actions of cyclic AMP, its butyryl derivatives and Na butyrate on the proliferation of malignant trophoblast cells in vitro", Br J Cancer 35(3) 314-321 (1977).
Bartam et al., "Proliferation of human colonic mucosa as an intermediate biomarker of carcinogenesis: effects of butyrate, deoxycholate, calcium, ammonia, and pH", Cancer Res 53(14) 3283-3288 (1993).
Barton et al., "The erythroid protein cGATA-1 functions with a stage-specific factor to activate transcription of chromatin-assembled beta-globin genes", Genes Dev 7(9) 1796-1809 (1993).
Basson et al., "Butyrate-induced enterocyte differentitation and mucosal wound healing", Gastroentreology 104(4) supp !235 (1993).
Belcheva et al., "Up-regulation of delta opioid receptors in neuroblastoma hybrid cells: evidence for differences in the mechanisms of action of sodium butyrate and naltrexone", J Pharmacol Exp Ther 259(1) 302-309 (1991).
Berkovitch et al., "Pharmacokinetics of arginine butyrate in patients with hemoglobinopathy", Environ Toxicol Pharmacol 2(4) 403-405 (1996).
Bernards et al., "Physical mapping of the globin gene deletion in hereditary persistence of foetal haemoglobin (HPFH)", Nucleic Acids Res 8(7) 1521-1534 (1980).
Bingham, "Patty's Toxicology" John Wiley and Sonds, Inc. Jan. 1, 2005, 707-711.
Birgens et al., "The thalassaemia syndromes", Scand J Clin Lab Invest 67(1) 11-25 (2007).
Blau et al., "Fetal hemoglobin induction with butyric acid: efficacy and toxicity", Blood 81(2) 529-537 (1993).
Bloch et al., "Induced cell differentiation in cancer therapy", Cancer Treat Rep 68(1) 199-205 (1984).
Bohacek et al., "Identification of novel small-molecule inducers of fetal hemoglobin using pharmacophore and PSEUDO' receptor models", Chem Biol Drug Des 67(5) 318-328 (2006).
Bohan et al., "Mutational analysis of sodium butyrate inducible elements in the human immunodeficiency virus type I long terminal repeat", Virology 172(2) 573-583 (1989).
Bohan et al., "Sodium butyrate activates human immunodeficiency virus long terminal repeat—directed expression", Biochem Biophys Res Commun 148(3) 899-905 (1987).
Bokiri et al., "Swine experiment with a feed containing sodium-n-butyrate", Chemical Abstracts 112(3) 438 (1990).
Bonnet et al. "Detection of Epstein-Barr virus in invasive breast cancers", J Natl Cancer Inst 91(16):1376-81 (1999).
Boosalis et al. "Short-chain fatty acid derivatives stimulate cell proliferation and induce STAT-5 activation", Blood 97(10) 3259-67 (2001).
Borgna-Pignatti et al "Survival and complications in thalassemia", Ann NY Acad Sci 1054: 40-7 (2005).
Borgna-Pignatti et al. "Modern treatment of thalassaemia intermedia", Br J Haematol 138(3) 291-304 (2007).
Boulikas "Poly(ADP-ribose) synthesis in blocked and damaged cells and its relation to carcinogenesis", Anticancer Res. 12(3) 885-98 (1992).
Bourantas et al. "Administration of high doses of recombinant human erythropoietin to patients with beta-thalassemia intermedia: a preliminary trial", Eur J. Haematol 58(1) 22-5 (1997).
Bourgeade et al. "Effect of sodium butyrate on the antiviral and anticellular action of interferon in normal and MSV-transformed cells", Int J Cancer 24(3) 314-8 (1979).
Bourgeade et al. "Enhancement of interferon antitumor action by sodium butyrate", Cancer Res 39(11) 4720-3 (1979).
Breitman et al. "Combinations of retinoic acid with either sodium butyrate, dimethyl sulfoxide, or hexamethylene bisacetamide synergistically induce differentiation of the human myeloid leukemia cell line HL60", Cancer Res 50(19) 6268-73 (1990).

Breuer et al. "Rectal irrigation with short-chain fatty acids for distal ulcerative colitis. Preliminary report", Dig Dis Sci 36(2) 185-7 (1991).
Briz et al "Epstein-Barr virus associated B-cell lymphoma after autologous bone marrow transplantation for T-cell acute lymphoblastic leukaemia", Br J Haematol 98(2) 485-7 (1997).
Brooks et al "The a- and b-wave latencies as a prognostic indicator of neovascularisation in central retinal vein occlusion", Doc Ophthalmol 99(2) 123-33 (1999).
Brousset et al "Detection of Epstein-Barr virus messenger RNA in Reed-Stemberg cells of Hodgkin's disease by in situ hybridization with biotinylated probes on specially processed modified acetone methyl benzoate xylene (ModAMeX) sections", 77(8) 1781-6 (1991).
Bugaut et al "Biological effects of short-chain fatty acids in non-ruminant mammals", Annu Rev Nutr 13: 217-41 (1993).
Bunn "Pathogenesis and treatment of sickle cell disease", N Engl J Med 337(11) 762-9 1997.
Burkitt "A sarcoma involving the jaws in African children", Br J Surg 46(197) 218-23 1958.
Williams et al "Identification of a ligand for the c-kit proto-oncogene", Cell 63(1) 167-74 1990.
Winichagoon et al "Beta-thalassemia in Thailand", Ann NY Acad Sci 612 31-42 1990.
Witt et al "Induction of fetal hemoglobin expression by the histone deacetylase inhibitor apicidin." Blood 101.5 2001-2007 2003.
Wittstruck et al "A nuclear magnetic resonance study of transmission of electronic effects. Ethylbenzenes, dihydrocinnamic acids, and cis—and trans-cinnamic acids", Journal of the American Chemical Society 89(15) 3803-3809 1967.
Wood et al "Hb F synthesis in sickle cell anaemia: a comparison of Saudi Arab cases with those of African origin", Br J Haematol 45(3) 431-45 1980.
Wu et al "Detection of EBV gene expression in Reed-Stemberg cells of Hodgkin's disease", Int J Cancer 46(5) 801-4 1990.
Yeivin et al "Sodium butyrate selectively induces transcription of promoters adjacent to the MoMSV viral enhancer", Gene 116(2) 159-64 1992.
Young et al "Phase I trial and clinical pharmacological evaluation of hexamethylene bisacetamide administration by ten-day continuous intravenous infusion at twenty-eight-day intervals", Cancer Res 48(24 Pt 1) 7304-9 1988.
Zeitlin et al "Evidence of CFTR function in cystic fibrosis after systemic administration of 4-phenylbutyrate", Mol Ther 6(1) 119-26 2002.
Zhang et al "Effect of (E)-5-(2-bromovinyl)-2'-deoxyuridine on several parameters of Epstein-Barr virus infection", J Gen Virol 65(Pt 1) 37-46 1984.
Zhang et al "Strategies in developing promising histone deacetylase inhibitors", Med Res Rev 30(4) 585-602 2010.
Zituik et al "The silencing of .gamma.-globin gene exin a .beta.-globin locus yac can be arrested by a .alpha.-aminobutyric acid", Abstract of ASH Annual Meeting, Seattle, Washington, Dec. 1-5, 1995.
Zsebo et al "Identification, purification, and biological characterization of hematopoietic stem cell factor from buffalo rat liver—conditioned medium", Cell 63(1) 195-201 1990.
Zsebo et al "Stem cell factor is encoded at the SI locus of the mouse and is the ligand for the c-kit tyrosine kinase receptor", Cell 63(1) 213-24 1990.
Zur Hausen et al "EBV DNA in biopsies of Burkitt tumours and anaplastic carcinomas of the nasopharynx", Nature 228(5276) 1056-8 1970.
Rund et al "Beta-thalassemia", N Engl J Med 353(11) 1135-46 2005.
Sachs "Cell differentiation and bypassing of genetic defects in the suppression of malignancy", Cancer Res 47(8) 1981-6 1987.
Sadaie et al "Induction of developmentally programmed cell death and activation of HIV by sodium butyrate", Virology 202(1) 513-8 1994.
Safaya et al "Augmentation of gamma-globin gene promoter activity by carboxylic acids and components of the human beta-globin locus control region", Blood 84(11) 3929-35 1994.

(56) References Cited

OTHER PUBLICATIONS

Saito et al "A synthetic inhibitor of histone deacetylase, MS-27-275, with marked in vivo antitumor activity against human tumors", Proc Natl Acad Sci USA 96(8) 4592-7 1999.
Scheppach et al "Effect of butyrate enemas on the colonic mucosa in distal ulcerative colitis", Gastroenterology 103 (1) 51-6 1992.
Scherr et al "School contact among persons with Hodgkin's disease", Am J Epidemiol 120(1) 29-38 1984.
Search Report and Written Opinion dated Feb. 11, 2011 for Application No. PCT/US10/59584.
Search Report issued during the prosecution of EP Appl. No. 10184726, dated May 11, 2011.
Seifter et al "An outlier theory of cancer curability. Tumor cell differentiation as a therapeutic goal", Am J Med 83(4) 757-60 1987.
Sher et al "Rapid healing of chronic leg ulcers during arginine butyrate therapy in patients with sickle cell disease and thalassemia", Blood 84(7) 2378-80 1994.
Shibata et al "Epstein-Barr virus-associated non-Hodgkin's lymphoma in patients infected with the human Immunodeficiency virus", Blood 81(8) 2101-9 1993.
Singer et al "Fetal haemoglobin augmentation in E/beta(0) thalassaemia: clinical and haematological outcome", Br J Haematol 131(3) 378-88 2005.
Slamon et al "Expression of cellular oncogenes in human malignancies", Science 224(4646) 256-62 1984.
Speck et al "Infection of breast epithelial cells with Epstein-Barr virus via cell-to-cell contact", J Natl Cancer Inst 92(22) 1849-51 2000.
Spyrou et al "Compounds of the anthracycline family of antibiotics elevate human γ-globin expression both in erythroid cultures and in a transgenic mouse model", Blood Cells, Molecules, and Diseases 44.2 100-106 (2010).
Sripichai et al "A scoring system for the classification of beta-thalassemia/Hb E disease severity", Am J Hematol 83(6) 482-4 2008.
Stamatoyannopolous et al "Fetal hemoglobin induction by acetate, a product of butyrate catabolism", Blood 84(9) 3198-204 1994.
Stamatoyannopolous et al "The regulation of hemoglobin switching", Johns Hopkins Uni Press 425-426 1990.
Steinberg et al "Effect of hydroxyurea on mortality and morbidity in adult sickle cell anemia: risks and benefits up to 9 years of treatment", JAMA 289(13) 1645-51 2003.
Steinberg et al "Fetal hemoglobin in sickle cell anemia: determinants of response to hydroxyurea. Multicenter Study of Hydroxyurea", Blood 89(3) 1078-88 1997.
Steinberg et al "Pharmacologic modulation of fetal hemoglobin", Medicine (Baltimore) 80(5) 328-44 2001.
Steinberg et al "Predicting clinical severity in sickle cell anaemia", Br J Haematol 129(4) 465-81 2005.
Su et al "Aggressive peripheral T-cell lymphomas containing Epstein-Barr viral DNA: a clinicopathologic and molecular analysis", Blood 77(4) 799-808 1991.
Sutherland et al "Induction of the expression of HLA class I antigens on K562 by interferons and sodium butyrate", Hum Immunol 12(2) 65-73 1985.
Swinnen "Overview of posttransplant B-cell lymphoproliferative disorders", Semin Oncol 26(5 Suppl n14) 21-5 1999.
Takahashi et al "Differentiation of cultured Friend leukemia cells induced by short-chain fatty acids", Gan 66(5) 577-80 1975.
Tang et al "Memory of butyrate induction by the Moloney murine sarcoma virus enhancer-promoter element", Biochem Biophys Res Commun 189(1) 141-7 1992.
Testa "Apoptotic mechanisms in the control of erythropoiesis", Leukemia 18(7) 1176-99 2004.
Torrealba-De Ron et al "Perturbations in the erythroid marrow progenitor cell pools may play a role in the augmentation of HbF by 5-azacytidine", Blood 63(1) 201-10 1984.
Toussirot et al "Epstein-Barr virus in autoimmune diseases", Best Pract Res Clin Rheumatol 22(5) 883-96 2008.
Tsai et al "Interplay between PKCδ and Sp1 on histone deacetylase inhibitor-mediated Epstein-Barr virus reactivation", J Virol 85(5) 2373-85 2011.
Tsao et al "Differential effects of sodium butyrate, dimethyl sulfoxide, and retinoic acid on membrane-associated antigen, enzymes, and glycoproteins of human rectal adenocarcinoma cells", Cancer Res 42(3) 1982.
Tsapis et al "HDAC inhibitors induce apoptosis in glucocorticoid-resistant acute lymphatic leukemia cells despite a switch from the extrinsic to the intrinsic death pathway", Int J Biochem Cell Biol 39(7-8) 1500-9 2007.
Tuan et al "Different 3' end points of deletions causing delta beta-thalassemia and hereditary persistence of fetal hemoglobin: implications for the control of gamma-globin gene expression in man", Proc Natl Acad Sci USA 80(22) 6937-41 1983.
Ulrich "Function of normal and mutated gamma-globin gene promoters in electroporated K562 erythroleukemia cells", Blood 75(4) 990-9 1990.
Vile et al "Systemic gene therapy of murine melanoma using tissue specific expression of the HSVtk gene involves an immune component", Cancer Res 54(23) 6228-34 1994.
Vinchinsky "Changing patterns of thalassemia worldwide", Ann NY Acad Sci 1054 18-24 2005.
Vinchinsky "Hemoglobin e syndromes", Hematology Am Soc Hematol Educ Program 79-83 2007.
Vinchinsky et al "Changes in the epidemiology of thalassemia in North America: a new minority disease", Pediatrics 116(6) e818-25 2005.
Volkov et al "Cinnamic acid in analytical chemistry. X determination of scandium as cinnamate and its separation for the rare earth elements and yttrium", Zh Anal Khim 22(3) 340-345 1967.
Walsh et al "Combination of drug and gene delivery by gelatin nanospheres for the treatment of cystic fibrosis", Proceedings of the Controlled Release Society (24) 75-76 1997.
Walter "The merck index of chemicals and drugs: an encyclopedia for chemists, pharmacists, physicians, and members of allied professions", JAMA 173(16) 1960.
Wasseman et al "Differential effects of sodium butyrate and dimethylsulfoxide on gamma-glutamyl transpeptidase and alkaline phosphatase activities in MCF-7 breast cancer cells", Pathobiology 55(4) 189-193 1987.
Watkins et al "Choleretic effect of structural analogs of valproic acid in the rat", Res Commun Chem Pathol Pharmacol 39(3) 355-66 1983.
Watson "Butyric acid in the treatment of cancer", The Lancet 221(5719) 746-48 1993.
Weatherall et al "A model for the persistence or reactivation of fetal haemoglobin production", Lancet 2(7987) 660-3 1976.
Weiss et al "Detection of Epstein-Barr viral genomes in Reed-Stemberg cells of Hodgkin's disease", N Engl J Med 320(8) 502-6 1989.
Weiss et al "Epstein-Barr viral DNA in tissues of Hodgkin's disease", Am J Pathol 129(1) 86-91 1987.
Weiss et al "Epstein-Barr virus and Hodgkin's disease. A correlative in situ hybridization and polymerase chain reaction study", Am J Pathol 139(6) 1259-65 1991.
Perrine et al "Phase 1 clinical testing of HQK-1001, a novel oral fetal globin gene inducer", Abstract from ASH Annual Meeting and Exposition 130 2008.
Perrine et al "Phase 1 clinical testing of HQK-1001, a novel oral fetal globin gene inducer", Slides presented at ASH Annual Meeting and Exposition 130 2008.
Perrine et al "Rh-Activin increases erythroid progenitor growth and HbF in childhood red cell failure syndromes and hemoglobinopathies", Blood 74(7) 1989.
Perrine et al "Sodium butyrate enhances fetal globin gene expression in erythroid progenitors of patients with Hb SS and beta thalassemia", Blood 74(1) 454-9 1989.
Planchon et al "Differential effects of butyrate derivatives on human breast cancer cells grown as organotypic nodules in vitro and as xenografts in vivo", In Vivo 6(6) 605-10 1992.

(56) References Cited

OTHER PUBLICATIONS

Planchon et al "Morphology and intermediate filament composition of human mammary epithelial cells treated with stable butyrate derivative", Anticancer Res 12(6B) 2315-20 1992.

Planchon et al "New stable butyrate derivatives alter proliferation and differentiation in human mammary cells", Int J Cancer 48(3) 443-9 1991.

Platt et al "Mortality in sickle cell disease. Life expectancy and risk factors for early death", N Engl J Med 330(23) 1639-44 1994.

Platt et al "Pain in sickle cell disease. Rates and risk factors", N Engl J Med 325(1) 11-6 1991.

Pootrakul et al "A correlation of erythrokinetics, ineffective erythropoiesis, and erythroid precursor apoptosis in Thai patients with thalassemia", Blood 96(7) 2606-12 2000.

Pouillart et al "Enhancement by stable butyrate derivatives of antitumor and antiviral actions of interferon", Int J Cancer 51(4) 596-601 1992.

* cited by examiner

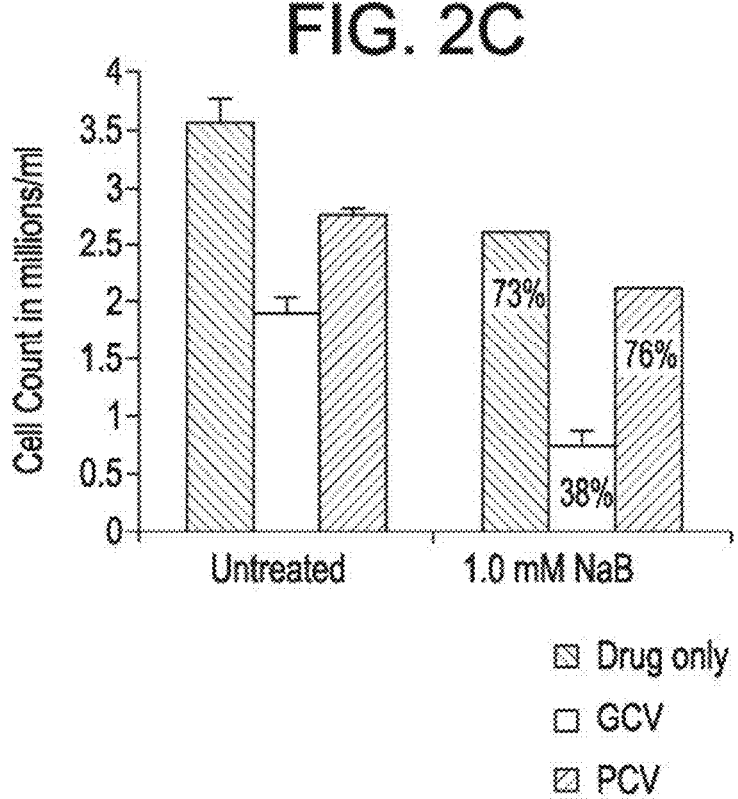
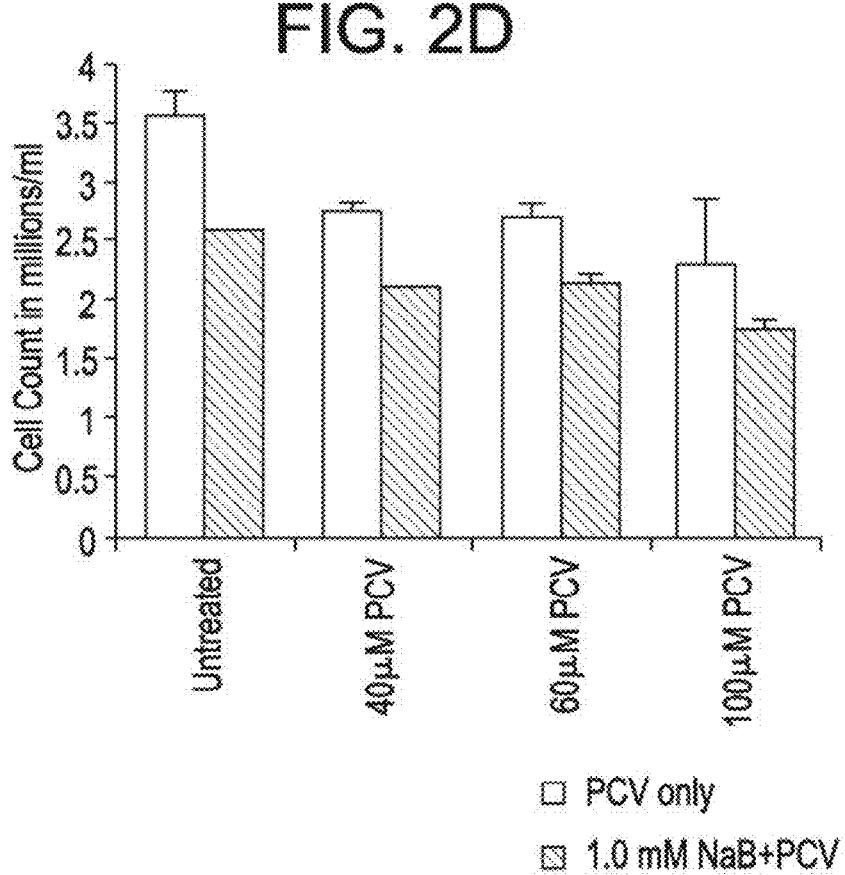

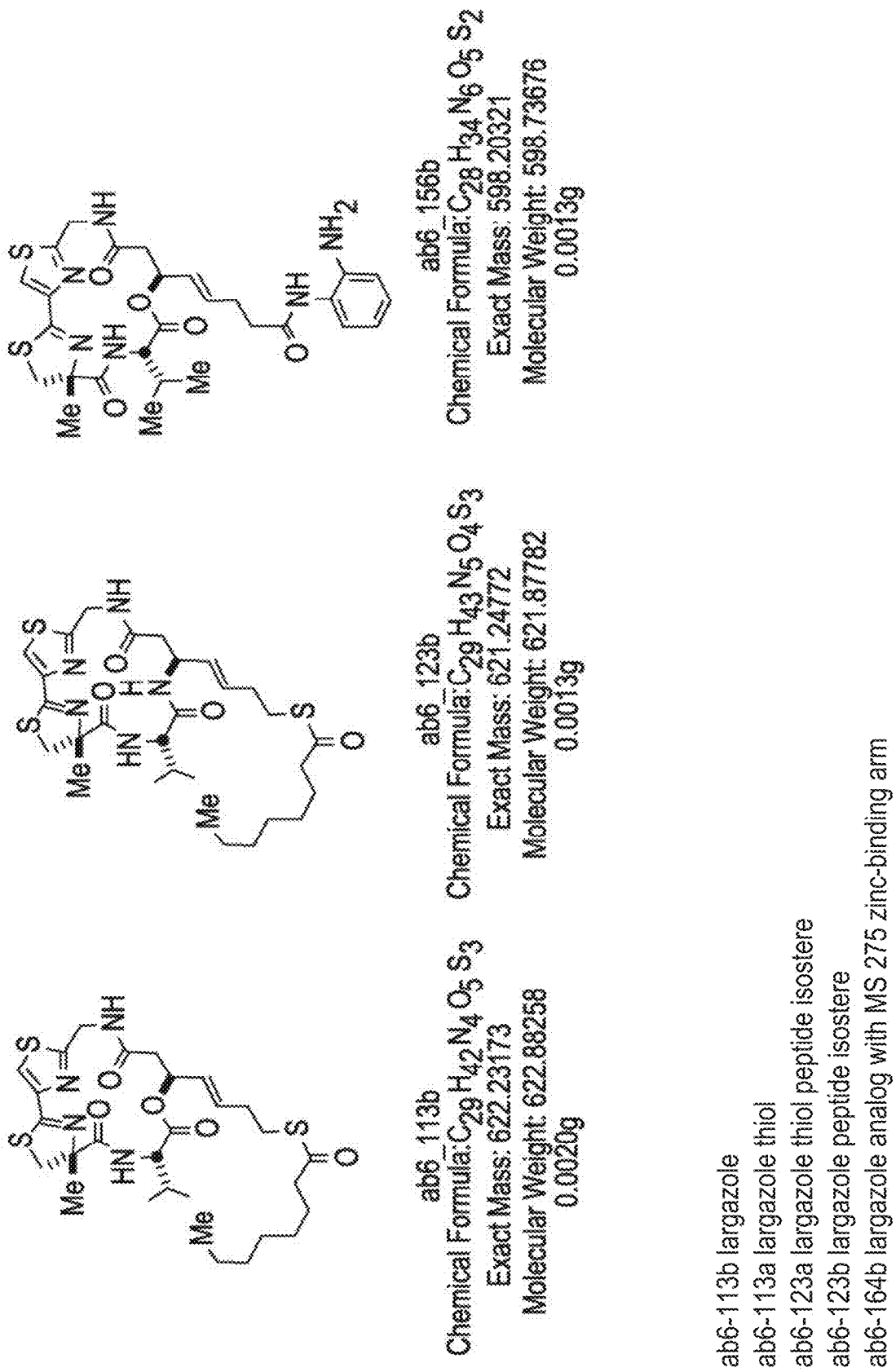

METHODS AND COMPOSITIONS FOR TREATING VIRAL OR VIRALLY-INDUCED CONDITIONS

CROSS-REFERENCE TO RELATED APPLICATIONS

This application is a continuation application of co-pending U.S. patent application Ser. No. 15/335,776 filed Oct. 27, 2016, which is a continuation application of U.S. patent application Ser. No. 14/728,592 filed Jun. 2, 2015, which is a continuation application of U.S. patent application Ser. No. 13/912,637 filed Jun. 7, 2013, which is a continuation application of U.S. patent application Ser. No. 13/046,555 filed on Mar. 11, 2011, which claims the benefit under 35 U.S.C. § 119(e) of U.S. Provisional Application No. 61/430,931 filed on Jan. 7, 2011, and U.S. Provisional Application No. 61/313,052 filed on Mar. 11, 2010, the contents of each of which are incorporated herein by reference in their entireties.

In compliance with 37 C.F.R. § 1.71(g)(1), disclosure is herein made that the claimed invention was made pursuant to a Joint Research Agreement as defined in 35 U.S.C. 103(c)(3), that was in effect on or before the date the claimed invention was made, and as a result of activities undertaken within the scope of the Joint Research Agreement, by or on the behalf of Boston University and Hemaquest Pharmaceuticals, Inc., now Viracta Therapeutics, Inc.

SEQUENCE LISTING

The instant application contains a Sequence Listing which has been submitted in ASCII format via EFS-Web and is hereby incorporated by reference in its entirety. Said ASCII copy, created on Apr. 19, 2018, is named 701586-070085_SL.txt and is 1,296 bytes in size.

BACKGROUND OF THE INVENTION

Many patients can have latent infections in which a virus is present but is not expressing viral proteins such as viral thymidine kinase or protein kinase, the target for common anti-viral drugs such as acyclovir and ganciclovir. A viral inducing drug such as a histone deacetylase inhibitor (HDAC inhibitor—HDACi) can be used to re-induce the expression of viral thymidine kinase or protein kinase in viral infected cells in the subject; the subject can then be treatment with antiviral drugs to eliminate latent viral infections. As EBV and/or other latent viral infections can be associated with a variety of conditions, many of which are inflammatory conditions, such as lymphomas, autoimmune conditions, allergic conditions, eliminating the latent virus with this therapy can be used to prevent or treat such conditions.

EBV can induce autoimmune conditions through a number of potential mechanisms, e.g.: 1) activating B cells to produce auto-antibodies, 2) turning on T cells that attack host tissue, 3) molecular mimicry in which EBV antigens cross react with host antigens such that autoimmune condition results when T cells or antibodies reactive with these antigens cross react with host antigens causing damage to host tissues, 4) EBV infected B cells produce cytokines which turn on other elements of the immune system and increase inflammation which can also exacerbate autoimmune condition, 5) EBV infected B or T cells can become immortalized via EBV proteins indirectly turning out anti-apoptotic or survival pathways. Autoimmune conditions with evidence of an EBV relationship include multiple sclerosis, systemic lupus erythematosus, rheumatoid arthritis and Sjogren's syndrome. Cytomegalovirus and herpes simplex virus have been associated with coronary artery condition.

There is a need for methods of treating and/or preventing viral conditions, viral-induced conditions, and related inflammatory conditions.

SUMMARY OF THE INVENTION

In one aspect, a method for treating and/or preventing a viral condition, a virally-induced condition, or an inflammatory condition comprising administering a histone deacetylase inhibitor (HDAC inhibitor) and an antiviral agent wherein the HDAC inhibitor is a pyrimidine hydroxamic acid derivative is provided.

In another aspect, a method for treating and/or preventing a viral or virally-induced condition is provided comprising administering a HDAC inhibitor and an antiviral agent wherein the viral or virally-induced condition is caused by a DNA virus and the HDAC inhibitor is administered at dose of less than 2 mg/kg per dose.

In yet another aspect, a method for treating and/or preventing a viral condition, a virally-induced condition, or an inflammatory condition is provided comprising administering a HDAC inhibitor and an antiviral agent wherein the MW of the HDAC inhibitor is greater than 275 g/mol.

In another aspect, a method for treating and/or preventing a viral condition or a virally-induced condition is provided, comprising administering a HDAC inhibitor wherein the HDAC inhibitor is a pyrimidine hydroxamic acid derivative.

In another aspect, a composition comprising a (i) HDAC inhibitor and (ii) an antiviral agent is provided, wherein the HDAC inhibitor is a pyrimidine hydroxamic acid derivative.

Provided herein, in one aspect, is a method for treating and/or preventing a viral or virally-induced condition comprising administering a HDAC inhibitor and an antiviral agent wherein the viral or virally-induced condition is caused by a DNA virus and the HDAC inhibitor is administered at dose of less than 2 mg/kg per dose. In some embodiments, the HDAC inhibitor is Vorinostat/suberoyl anilide hydroxamic acid, JNJ-26481585 (N-hydroxy-2-(4-((((1-methyl-1H-indol-3-yl)methyl)amino)methyl)piperidin-1-yl)pyrimidine-5-carboxamide), R306465/JNJ-16241199 (N-hydroxy-5-(4-(naphthalen-2-ylsulfonyl)piperazin-1-yl) pyrimidine-2-carboxamide), CHR-3996 (2-(6-{[(6-Fluoroquinolin-2-yl)methyl]amino}-3-azabicyclo[3.1.0]hex-3-yl)-N-hydroxypyrimidine-5-carboxamide), Belinostat/PXD101, Panobinostat/LBH-589, trichostatin A/TSA (7-[4-(dimethylamino)phenyl]-N-hydroxy-4,6-dimethyl-7-oxohepta-2,4-dienamide), ITF2357, CBHA, Givinostat/ITF2357, romidepsin (Istodax™), PCI-24781, depsipeptide (FR901228 or FK228), butyrate, phenylbutyrate, valproic acid, AN-9, CI-994, Entinostat/MS-275, SNDX-275, mocetinostat/MGCD0103 (N-(2-aminophenyl)-4-((4-pyridin-3-ylpyrimidin-2-ylamino)methyl)benzamide), m-carboxycinnamic acid, bishydroxamic acid, suberic bishydroxamic acid, oxamflatin, ABHA, SB-55629, pyroxamide, propenamides, aroyl pyrrolyl hydroxamides, and LAQ824 (((E)-N-hydroxy-3-[4-[[2-hydroxyethyl-[2-(1H-indol-3-yl)ethyl]amino]methyl]phenyl]prop-2-enamide). In other embodiments, the HDAC inhibitor is a largazole derivative. In certain embodiments, the HDAC inhibitor is a N-hydroxypyrimidine-5-carboxamide, wherein the HDAC inhibitor comprises an azabicyclo-hexane, wherein the HDAC inhibitor comprises a fluoroquinoline group, or wherein the HDAC inhibitor is a non-piperidine-containing pyrimidine hydroxamic acid derivative.

In certain embodiments, the DNA virus is a herpes virus. In some embodiments, the herpes virus is an Epstein-Barr virus.

In some embodiments, the HDAC inhibitor and the antiviral agent are co-formulated. In certain embodiments, the co-formulation comprises a unit dose of no greater than 80 mg of the HDAC inhibitor and no greater than 1500 mg of the antiviral agent.

In certain embodiments, the HDAC inhibitor can penetrate the blood brain barrier.

In some embodiments, the method further comprises administering an additional agent. In certain embodiments, the additional agent is an antiviral agent, a HDAC inhibitor, or a chemotherapeutic.

In certain embodiments, the virally-induced condition is a cancerous condition, an inflammatory condition, an autoimmune condition, an allergic condition, or a skin condition. In some embodiments, the virally-induced condition is a lymphoma, chronic lymphocytic leukemia, nasopharyngeal carcinoma, gastric cancer, Kaposi's sarcoma, rheumatoid arthritis, systemic lupus erythematosus, or multiple sclerosis.

Also provided herein, in an additional aspect, is a method for treating and/or preventing a viral condition, a virally-induced condition, or an inflammatory condition comprising administering a HDAC inhibitor and an antiviral agent wherein the MW of the HDAC inhibitor is greater than 275 g/mol. In some embodiments, the HDAC inhibitor is a N-hydroxypyrimidine-5-carboxamide, wherein the HDAC inhibitor comprises an azabicyclo-hexane, wherein the HDAC inhibitor comprises a fluoroquinoline group, or wherein the HDAC inhibitor is a non-piperidine-containing pyrimidine hydroxamic acid derivative. In certain embodiments, the HDAC inhibitor is JNJ-26481585 (N-hydroxy-2-(4-((((1-methyl-1H-indol-3-yl) methyl)amino)methyl)piperidin-1-yl)pyrimidine-5-carboxamide), R306465/JNJ-16241199 (N-hydroxy-5-(4-(naphthalen-2-ylsulfonyl)piperazin-1-yl)pyrimidine-2-carboxamide), or CHR-3996 (2-(6-{[(6-Fluoroquinolin-2-yl) methyl]amino}-3-azabicyclo[3.1.0]hex-3-yl)-N-hydroxypyrimidine-5-carboxamide). In other embodiments, the HDAC inhibitor is a largazole derivative.

In some embodiments, the viral or virally induced condition is caused by a herpes virus. In certain embodiments, the herpes virus is an Epstein-Barr virus.

In some embodiments, the HDAC inhibitor and the antiviral agent are administered simultaneously. In certain embodiments, the HDAC inhibitor and the antiviral agent are administered orally.

In some embodiments, the HDAC inhibitor is administered at 0.01-1 mg/kg per dose. In certain embodiments, 1, 2, 3, or 4 doses are administered daily. In some embodiments, the total daily dosage of the HDAC inhibitor is no greater than about 200 mg. In certain embodiments, the antiviral agent is valganciclovir and is administered at dose of 500-1500 mg/dose.

In some embodiments, the HDAC inhibitor and the antiviral agent are co-formulated. In certain embodiments, the co-formulation comprises a unit dose of no greater than 80 mg of the HDAC inhibitor and no greater than 1500 mg of the antiviral agent. In some embodiments, the antiviral agent is valganciclovir, and the valganciclovir is a timed release or slow release oral formulation.

In certain embodiments, the viral condition or virally-induced condition is caused by a human immunodeficiency virus, a herpes virus, a parvovirus, a coxsackie virus, a Human T-lymphotropic virus, a BK virus, or a hepatitis virus. In some embodiments, the viral condition or virally-induced condition is caused by a retrovirus or a herpes virus. In certain embodiments, the herpes virus is a herpes simplex virus, a herpes genitalis virus, a varicella zoster virus, an Epstein-Barr virus, a human herpes virus 6, a herpes virus type 1, herpes virus type 2, a human herpes virus type 8, or a cytomegalovirus. In some embodiments, the herpes virus is the Epstein-Barr virus. In certain embodiments, the viral condition or virally-induced condition is caused by a DNA virus. In some embodiments, the viral condition or virally-induced condition is not caused by a retrovirus.

In certain embodiments, the virally-induced condition is a cancer, an inflammatory condition, an allergic condition, an autoimmune condition, or a skin condition. In some embodiments, the virally-induced condition is lymphoma, chronic lymphocytic leukemia, nasopharyngeal carcinoma, gastric cancer, Kaposi's sarcoma, rheumatoid arthritis, systemic lupus erythematosus, or multiple sclerosis. In certain embodiments, the virally-induced condition is not sepsis or viremia. In some embodiments, the inflammatory condition is an autoimmune condition, and allergic condition, or a skin condition.

In certain embodiments, the HDAC inhibitor can penetrate the blood brain barrier. In some embodiments, the antiviral agent is a HIV drug, a Herpes drug, a CMV drug, or a hepatitis drug. In certain embodiments, the antiviral agent is acyclovir, ganciclovir or valganciclovir. In some embodiments, the antiviral agent is not a heat shock protein inhibitor, an immunosuppressant, an antibiotic, a glucocorticoid, a non-steroidal anti-inflammatory drug, a Cox-2-specific inhibitor or a TNF-α binding protein. In certain embodiments, the antiviral agent is not a Hsp90 inhibitor, tacrolimus, cyclosporin, rapamycin (sirolimus), methotrexate, cyclophosphamide, azathioprine, mercaptopurine, mycophenolate, FTY720, levofloxacin, amoxycillin, prednisone, cortisone acetate, prednisolone, methylprednisolone, dexamethasone, betamethasone, triamcinolone, beclometasone, fludrocortisone acetate, deoxycorticosterone acetate, aldosterone, salicylates, arylalkanoic acids, a 2-arylpropionic acid, a N-arylanthranilic acid, an oxicam, a coxib, a sulphonanilide, valdecoxib, celecoxib, rofecoxib, leflunomide, gold thioglucose, gold thiomalate, aurofin, sulfasalazine, hydroxychloroquinine, minocycline, infliximab, etanercept, adalimumab, abatacept, anakinra, interferon-β, interferon-γ, interleukin-2, an allergy vaccine, an antihistamine, an antileukotriene, a beta-agonist, theophylline, or an anticholinergic.

In some embodiments, the method further comprises administering an additional agent. In certain embodiments, the additional agent is an antiviral agent, a HDAC inhibitor, or a chemotherapeutic.

Further provided herein, in one aspect, is a method for treating and/or preventing a viral condition, a virally-induced condition, or an inflammatory condition comprising administering a HDAC inhibitor and an antiviral agent, wherein the HDAC inhibitor is a heterocyclic hydroxamic acid derivative. In some embodiments, the HDAC inhibitor is a pyrimidine hydroxamic acid derivative. In certain embodiments, the HDAC inhibitor is a N-hydroxypyrimidine-5-carboxamide, wherein the HDAC inhibitor comprises an azabicyclo-hexane, wherein the HDAC inhibitor comprises a fluoroquinoline group, or wherein the HDAC inhibitor does not comprise a piperidine group. In some embodiments, the HDAC inhibitor is JNJ-26481585 (N-hydroxy-2-(4-((((1-methyl-1H-indol-3-yl)methyl)amino)

methyl)piperidin-1-yl)pyrimidine-5-carboxamide), R306465/JNJ-16241199 (N-hydroxy-5-(4-(naphthalen-2-ylsulfonyl)piperazin-1-yl)pyrimidine-2-carboxamide), or CHR-3996 (2-(6-{[(6-Fluoroquinolin-2-yl)methyl]amino}-3-azabicyclo[3.1.0]hex-3-yl)-N-hydroxypyrimidine-5-carboxamide).

In some embodiments, the HDAC inhibitor and the antiviral agent are administered simultaneously. In certain embodiments, the HDAC inhibitor and the antiviral agent are administered orally. In some embodiments, the antiviral agent is valganciclovir. In certain embodiments, the HDAC inhibitor is administered at 0.2-2 mg/kg per dose. In some embodiments, 1, 2, 3, or 4 doses are administered daily. In certain embodiments, the total daily dosage of the HDAC inhibitor is no greater than about 100 mg. In some embodiments, valganciclovir is administered at dose of 900 mg/dose or less.

In certain embodiments, the HDAC inhibitor and the antiviral agent are co-formulated. In some embodiments, the co-formulation comprises a unit dose of no greater than 80 mg of the HDAC inhibitor and no greater than 1500 mg of the antiviral agent.

In certain embodiments, the viral condition or virally-induced condition is caused by a human immunodeficiency virus, a herpes virus, a parvovirus, a coxsackie virus, a Human T-lymphotropic virus, a BK virus, or a hepatitis virus. In specific embodiments, the herpes virus is a herpes simplex virus, a herpes genitalis virus, a varicella zoster virus, an Epstein-Barr virus, a human herpes virus 6, a herpes virus type 1, herpes virus type 2, a human herpes virus type 8, or a cytomegalovirus.

In some embodiments, the viral condition or virally-induced condition is caused by a DNA virus. In certain embodiments, the viral condition or virally-induced condition is caused by an Epstein-Barr virus. In some embodiments, the viral condition or virally-induced condition is not caused by a retrovirus. In certain embodiments, the virally-induced condition is a cancer, an inflammatory condition, an allergic condition, an autoimmune condition, or a skin condition. In some embodiments, the virally-induced condition is lymphoma, chronic lymphocytic leukemia, nasopharyngeal carcinoma, gastric cancer, Kaposi's sarcoma, rheumatoid arthritis, systemic lupus erythematosus, or multiple sclerosis. In certain embodiments, the virally-induced condition is not sepsis or viremia. In specific embodiments, the inflammatory condition is an autoimmune condition, and allergic condition, or a skin condition.

In some embodiments, the HDAC inhibitor can penetrate the blood brain barrier.

In certain embodiments, the antiviral agent is a HIV drug, a Herpes drug, a CMV drug, or a hepatitis drug. In some embodiments, the antiviral agent is acyclovir, ganciclovir, or valganciclovir. In certain embodiments, the antiviral agent is not a heat shock protein inhibitor, an immunosuppressant, an antibiotic, a glucocorticoid, a non-steroidal anti-inflammatory drug, a Cox-2-specific inhibitor or a TNF-α binding protein. In other embodiments, the antiviral agent is not a Hsp90 inhibitor, tacrolimus, cyclosporin, rapamycin (sirolimus), methotrexate, cyclophosphamide, azathioprine, mercaptopurine, mycophenolate, FTY720, levofloxacin, amoxycillin, prednisone, cortisone acetate, prednisolone, methylprednisolone, dexamethasone, betamethasone, triamcinolone, beclometasone, fludrocortisone acetate, deoxycorticosterone acetate, aldosterone, salicylates, arylalkanoic acids, a 2-arylpropionic acid, a N-arylanthranilic acid, an oxicam, a coxib, a sulphonanilide, valdecoxib, celecoxib, rofecoxib, leflunomide, gold thioglucose, gold thiomalate, aurofin, sulfasalazine, hydroxychloroquinine, minocycline, infliximab, etanercept, adalimumab, abatacept, anakinra, interferon-β, interferon-γ, interleukin-2, an allergy vaccine, an antihistamine, an antileukotriene, a beta-agonist, theophylline, or an anticholinergic.

In some embodiments, the method further comprises administering an additional agent. In certain embodiments, the additional agent is an antiviral agent, a HDAC inhibitor, or a chemotherapeutic therapy.

Also provided herein, in another aspect, is a method for treating and/or preventing a viral condition or a virally-induced condition comprising administering a HDAC inhibitor wherein the HDAC inhibitor is a pyrimidine hydroxamic acid derivative comprising an azabicyclohexane, or wherein the HDAC inhibitor is a non-piperidine-containing pyrimidine hydroxamic acid derivative. In some embodiments, the HDAC inhibitor is a pyrimidine hydroxamic acid derivative comprising an azabicyclohexane. In certain embodiments, the HDAC inhibitor is a non-piperidine-containing pyrimidine hydroxamic acid derivative. In some embodiments, the HDAC inhibitor comprises a fluoroquinoline group.

In some embodiments, the method further comprises administering an antiviral agent. In certain embodiments, the HDAC inhibitor and antiviral agent are administered simultaneously. In some embodiments, the HDAC inhibitor is administered orally. In certain embodiments, the HDAC inhibitor is administered at 0.01-1 mg/kg per dose. In some embodiments, 1, 2, 3, or 4 doses are administered daily. In certain embodiments, the total daily dosage of the HDAC inhibitor is no greater than about 200 mg. In some embodiments, the antiviral agent is administered at dose of 500-1500 mg/dose.

In certain embodiments, the HDAC inhibitor and the antiviral agent are co-formulated. In some embodiments, the co-formulation comprises a unit dose of no greater than 80 mg of the HDAC inhibitor and no greater than 1500 mg of the antiviral agent. In certain embodiments, the antiviral agent is valganciclovir.

In some embodiments, the viral condition or virally-induced condition is caused by a human immunodeficiency virus, a herpes virus, a parvovirus, a coxsackie virus, a Human T-lymphotropic virus, a BK virus, or a hepatitis virus. In specific embodiments, the herpes virus is a herpes simplex virus, a herpes genitalis virus, a varicella zoster virus, an Epstein-Barr virus, a human herpes virus 6, a herpes virus type 1, herpes virus type 2, a human herpes virus type 8, or a cytomegalovirus. In some embodiments, the herpes virus is the Epstein-Barr virus.

In certain embodiments, the viral condition or virally-induced condition is caused by a DNA virus. In some embodiments, the viral condition or virally-induced condition is not caused by a retrovirus. In certain embodiments, the virally-induced condition is a cancer, an inflammatory condition, an allergic condition, an autoimmune condition, or a skin condition. In some embodiments, the virally-induced condition is a lymphoma, chronic lymphocytic leukemia, nasopharyngeal carcinoma, gastric cancer, Kaposi's sarcoma, rheumatoid arthritis, systemic lupus erythematosus, or multiple sclerosis. In certain embodiments, the virally-induced condition is not sepsis or viremia.

In some embodiments, the HDAC inhibitor can penetrate the blood brain barrier. In certain embodiments, the antiviral agent is a HIV drug, a Herpes drug, a CMV drug, or a hepatitis drug. In some embodiments, the antiviral agent is acyclovir, ganciclovir or valganciclovir. In certain embodiments, the antiviral agent is not a heat shock protein inhibitor, an immunosuppressant, an antibiotic, a glucocorticoid, a non-steroidal anti-inflammatory drug, a Cox-2-specific inhibitor or a TNF-α binding protein. In other embodiments, the antiviral agent is not a Hsp90 inhibitor, tacrolimus, cyclosporin, rapamycin (sirolimus), methotrexate, cyclophosphamide, azathioprine, mercaptopurine, mycophenolate, FTY720, levofloxacin, amoxycillin, prednisone, cortisone acetate, prednisolone, methylprednisolone, dexamethasone, betamethasone, triamcinolone, beclometasone, fludrocortisone acetate, deoxycorticosterone acetate, aldosterone, salicylates, arylalkanoic acids, a 2-arylpropionic acid, a N-arylanthranilic acid, an oxicam, a coxib, a sulphonanilide, valdecoxib, celecoxib, rofecoxib, leflunomide, gold thioglucose, gold thiomalate, aurofin, sulfasalazine, hydroxychloroquinine, minocycline, infliximab, etanercept, adalimumab, abatacept, anakinra, interferon-β, interferon-γ, interleukin-2, an allergy vaccine, an antihistamine, an antileukotriene, a beta-agonist, theophylline, or an anticholinergic.

In some embodiments, the method further comprises administering an additional agent. In certain embodiments, the additional agent is an antiviral agent, a HDAC inhibitor, or a chemotherapeutic therapy.

Further provided herein, in another aspect, is a composition comprising a (i) HDAC inhibitor and (ii) an antiviral agent wherein the HDAC inhibitor is a pyrimidine hydroxamic acid derivative. In some embodiments, the HDAC inhibitor is JNJ-26481585 (N-hydroxy-2-(4-((((1-methyl-1H-indol-3-yl) methyl)amino)methyl)piperidin-1-yl)pyrimidine-5-carboxamide), R306465/JNJ-16241199 (N-hydroxy-5-(4-(naphthalen-2-ylsulfonyl) piperazin-1-yl) pyrimidine-2-carboxamide), or CHR-3996 (2-(6-{[(6-Fluoroquinolin-2-yl) methyl]amino}-3-azabicyclo[3.1.0]hex-3-yl)-N-hydroxypyrimidine-5-carboxamide). In some embodiments, the HDAC inhibitor is not m-carboxycinnamic acid, bishydroxamic acid, suberic bishydroxamic acid, Trichostatin A (7-[4-(dimethylamino)phenyl]-N-hydroxy-4,6-dimethyl-7-oxohepta-2,4-dienamide), SAHA (suberoyl anilide hydroxamic acid)/Vorinostat, oxamflatin, ABHA, SB-55629, pyroxamide, propenamides, aroyl pyrrolyl hydroxamides, Belinostat/PXD101, Papobinostat, LAQ824 (((E)-N-hydroxy-3-[4-[[2-hydroxyethyl-[2-(1H-indol-3-yl)ethyl]amino]methyl]phenyl]prop-2-enamide), LBH589, or TSA. In certain embodiments, the HDAC inhibitor can penetrate the blood brain barrier.

In some embodiments, the antiviral agent is a HIV drug, a Herpes drug, a CMV drug, or a hepatitis drug. In certain embodiments, the antiviral agent is acyclovir, ganciclovir, or valganciclovir. In some embodiments, the antiviral agent is not a heat shock protein inhibitor, an immunosuppressant, an antibiotic, a glucocorticoid, a non-steroidal anti-inflammatory drug, a Cox-2-specific inhibitor or a TNF-α binding protein. In other embodiments, the antiviral agent is not a Hsp90 inhibitor, tacrolimus, cyclosporin, rapamycin (sirolimus), methotrexate, cyclophosphamide, azathioprine, mercaptopurine, mycophenolate, FTY720, levofloxacin, amoxycillin, prednisone, cortisone acetate, prednisolone, methylprednisolone, dexamethasone, betamethasone, triamcinolone, beclometasone, fludrocortisone acetate, deoxycorticosterone acetate, aldosterone, salicylates, arylalkanoic acids, a 2-arylpropionic acid, a N-arylanthranilic acid, an oxicam, a coxib, a sulphonanilide, valdecoxib, celecoxib, rofecoxib, leflunomide, gold thioglucose, gold thiomalate, aurofin, sulfasalazine, hydroxychloroquinine, minocycline, infliximab, etanercept, adalimumab, abatacept, anakinra, interferon-β, interferon-γ, interleukin-2, an allergy vaccine, an antihistamine, an antileukotriene, a beta-agonist, theophylline, or an anticholinergic.

In certain embodiments, the composition further comprises an additional agent. In some embodiments, the additional agent is an antiviral agent, a HDAC inhibitor, or a chemotherapeutic drug.

In some embodiments, the HDAC inhibitor and the antiviral agent are in an oral formulation. In certain embodiments, the HDAC inhibitor is present at 0.01-1 mg/kg per dose. In some embodiments, the oral formulation comprises a unit dose of no greater than 80 mg of the HDAC inhibitor and no greater than 1500 mg of the antiviral agent.

Additionally provided herein, in a further aspect, is a method for treating and/or preventing a virus-induced inflammatory condition in a subject comprising administering a viral inducing agent and an antiviral agent to the subject, thereby treating and/or preventing the inflammatory condition. In some embodiments, the virus is a member of the herpes virus family, human immunodeficiency virus, parvovirus, or coxsackie virus. In certain embodiments, the member of the herpes virus family is herpes simplex virus, herpes genitalis virus, varicella zoster virus, Epstein-Barr virus, human herpesvirus 6, or cytomegalovirus. In some embodiments, the member of the herpes virus family is Epstein-Barr virus, cytomegalovirus, or human herpesvirus 6.

In certain embodiments, the inflammatory condition is an autoimmune condition. In some embodiments, the autoimmune condition is rheumatoid arthritis, multiple sclerosis, Sjogren's syndrome, systemic lupus erythematosus, autoimmune hepatitis, autoimmune thyroiditis, hemophagocytic syndrome, diabetes, Crohn's condition, ulcerative colitis, psoriasis, psoriatic arthritis, idiopathic thrombocytonpenic pupura, polymyositis, dermatomyositis, myasthenia gravis, autoimmune thryroiditis, Evan's syndrome, autoimmune hemolytic anemia, aplastic anemia, autoimmune neutropenia, scleroderma, Reiter's syndrome, ankylosing spondylitis, pemphnigus, pemphigoid or autoimmune hepatitis. In certain embodiments, the inflammatory condition is an allergic condition. In some embodiments, the inflammatory condition is a skin condition. In some embodiments, the inflammatory condition is associated with coronary artery condition or peripheral artery condition. In certain embodiments, the inflammatory condition is retinitis, pancreatitis, cardiomyopathy, pericarditis, colitis, glomerulonephritis, lung inflammation, esophagitis, gastritis, duodenitis, ileitis, meningitis, encephalitis, encephalomyelitis, transverse myelitis, cystitis, urethritis, mucositis, lymphadenitis, dermatitis, hepatitis, osteomyelitis, or herpes zoster. In some embodiments, the inflammatory condition is atherosclerosis. In certain embodiments, the virus is cytomegalovirus or herpes simplex virus.

In some embodiments, the viral inducing agent is one or more of a chemotherapeutic drug, HDAC inhibitor, or DNA demethylating agent. In certain embodiments, the HDAC inhibitor is butyrate or MS-275.

In some embodiments, the viral inducing agent can penetrate the blood brain barrier. In certain embodiments, the viral inducing agent comprises arginine butyrate. In some embodiments, the antiviral agent is ganciclovir or valganciclovir.

In certain embodiments, the method further comprises administering an additional agent. In some embodiments, the additional agent comprises a vaccine. In certain embodiments, the vaccine comprises myelin basic protein and the condition is multiple sclerosis. In some embodiments, the vaccine comprises an antigen and the condition is diabetes. In certain embodiments, the additional agent is aspirin, naproxen, ibuprofen, or a statin. In some embodiments, the inflammatory condition is an autoimmune condition and the additional agent is cyclosporine, azathiorprine, methotrexate, cyclophosphamide, FK506, tacrolimus, monoclonal antibody, anti-T cell monoclonal antibody, anti-B cell monoclonal antibody, IL-2 receptor antibody, or a TNF inhibitor. In certain embodiments, the monoclonal antibody is an anti-B cell antibody. In some embodiments, the anti-B cell antibody is anti-CD20. In certain embodiments, the anti-T cell antibody is an anti-CD3 antibody. In some embodiments, the anti-CD3 antibody is OKT3. In certain embodiments, the TNF inhibitor is infliximab (Remicade™), etanercept (Enbrel™), Adalimumab (Humira™), or an anti-IL-6 antibody.

In certain embodiments, the inflammatory condition is atherosclerosis and the additional agent is a lipid lowering agent. In some embodiments, the lipid lowering agent is rosuvastatin, atorvastatin, simvastatin, or lovastatin. In certain embodiments, the inflammatory condition is multiple sclerosis and the additional agent is mitoxantrone, cladribine, or Campath antibody. In some embodiments, the viral inducing agent is administered to the subject before the antiviral agent.

INCORPORATION BY REFERENCE

All publications, patents, and patent applications mentioned in this specification are herein incorporated by reference to the same extent as if each individual publication, patent, or patent application was specifically and individually indicated to be incorporated by reference.

The following are also incorporated by reference: U.S. Pat. Nos. 6,677,302; 7,399,787; US 2009/0270497; US 2010/0093824; US 2010/0152155; WO1998/04290; WO 2004/113336; WO 2008/097654; Moffat, D. et al, Discovery of 2-(6-{[(6-Fluoroquinolin-2-yl)methyl]amino}bicyclo[3.1.0]hex-3-yl)-N-hydroxypyrimidine-5-carboxamide (CHR-3996), a Class I Selective Orally Active HDAC inhibitor, *Journal of Medicinal Chemistry* (2010), 53, 8663-8678; Glaser, K B, HDAC inhibitors: Clinical update and mechanisms-based potential, *Biochem. Pharmacol.* (2007); Ghosh, S. K., et al. 2007 *Blood Cells, Molecules, and Diseases* 38:57-65.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A and FIG. 1B show pre- and post-treatment, respectively.

FIGS. 2A-2D illustrate results from toxicity assays with anti-herpesvirus drugs ganciclovir (GCV) and penciclovir (PCV). FIG. 2A and FIG. 2B show results from various concentrations of GCV and PCV.

FIG. 2C and FIG. 2D show results from GCV and PCV used in combination with NaB.

FIG. 3A shows cell count results after using NaB. FIG. 3B shows results from VA.

FIG. 3C shows fold of TK expression induced.

FIG. 4A shows cell count results after using scriptaid. FIG. 4B shows fold of TK expression induced.

FIG. 5A shows cell count results after using SAHA. FIG. 5B shows fold of TK expression induced.

FIG. 6A shows cell count results after using LHB589. FIG. 6B shows fold of TK expression induced.

FIG. 8 shows cell count results after using oxamflatin.

FIG. 9 shows cell count results after using apicidin.

FIG. 10A shows cell count results after using MS-275. FIG. 10B shows fold of TK expression induced. FIG. 10C shows cell count results after treating cells in combination for shorter time periods.

FIGS. 11A-11B illustrate chemical structures of largazole compounds used. Shown in both FIG. 11A and FIG. 11B.

FIGS. 12A, 12B, 12C, 12D and 12E show cell count results after using various largazole compounds. FIG. 12F shows fold of TK expression induced from various largazole compounds.

DETAILED DESCRIPTION OF THE INVENTION

Figure 1A:
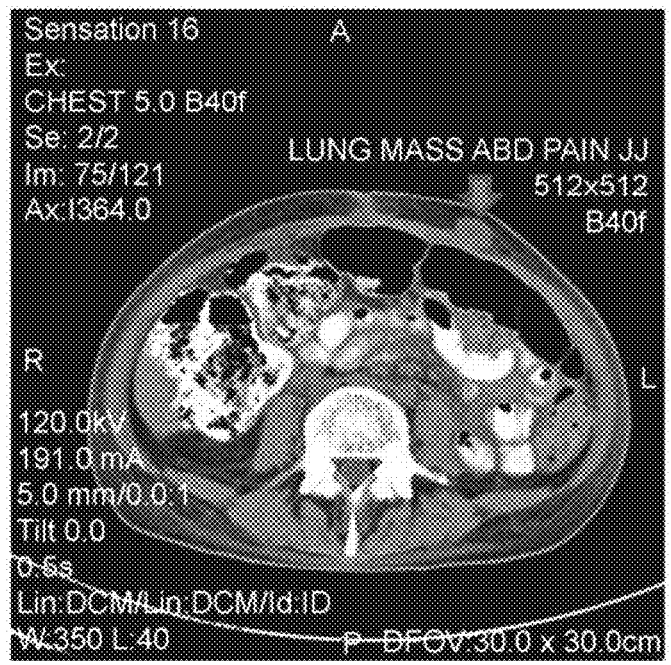
FIGS. 1A-1B illustrate a CT scan of tumor reduction after treatment with arginine butyrate (AB) and GCV.

Provided herein are methods and compositions for treating and/or preventing viral conditions, virally-induced conditions, or inflammatory conditions in a subject. The condition can be associated with latent viral infections. The methods can comprise the steps of administering a viral inducing agent and an antiviral agent to the subject. The method can comprise steps of administering a viral inducing agent, an antiviral agent, and one or more additional agents to a subject. The methods include the co-administration of an oral HDAC inhibitor and an antiviral agent, either in the same or separate formulations.

The methods and compositions provided can be used to treat and/or prevent infection by any of the viruses described herein. The methods and compositions can be used to treat and/or prevent any of the inflammatory conditions described herein. Any of the viral inducing agents and/or antiviral agents described herein can be used in the methods and compositions of the provided invention. The viral inducing agent can be an HDAC inhibitor. The HDAC inhibitor can be a pyrimidine hydroxamic acid derivative.

One or more additional agents described herein can be administered to a subject. An additional agent can be selected for administration based on the type of condition the subject has or is suspected of having.

Another aspect of the present invention relates to formulations, routes of administration and effective doses for pharmaceutical compositions comprising an agent or combination of agents, e.g., viral inducing agents, antiviral agents, or one or more additional agents. A viral inducing agent, antiviral agent, or one or more additional agents can be administered to a subject in separate pharmaceutical compositions or can be co-formulated in a single pharmaceutical composition.

Also provided are methods relating to dosing schedules for administering a viral inducing agent, antiviral agent, or one or more additional agents. One or more pharmaceutical compositions can be administered to a subject by "pulsed administration" over a period of time.

Overview

Like all other herpes viruses, EBV has two stages of replication, the lytic and the latent. Soon after primary infection, immunological surveillance by the host forces EBV to enter the latent state of infection, where only few selected genes are expressed. EBV maintains this latent state in all EBV-associated tumors. Conventional anti-herpes virus drugs, such as ganciclovir, acyclovir, etc., fail to act on these latently-infected cells because the viral enzyme thymidine kinase (TK) or protein kinase (PK), which is necessary for the conversion of the prodrugs to their toxic metabolites, is not expressed in latently-infected cells. Provided herein, in some embodiments, is a combination treatment wherein lytic replication is induced and antiviral drugs are administered concurrently.

Previous studies using patient-derived cells in vitro, and also from phase I/II clinical studies on a series of patients with EBV-associated lymphomas, have clearly shown the great promise of this combination therapy approach. Strong epidemiological association of Epstein-Barr Virus (EBV) with various human lymphoid malignancies and in vitro studies demonstrating tumorigenic activity of many EBV latent gene products suggest a causal relationship between EBV and these diseases. However, as EBV maintains a latent state of infection in these lymphomas, typical anti-herpes viral drugs, such as the nucleoside analogs ganciclovir (GCV) or acyclovir, are ineffective as these pro-drugs require expression of a lytic phase EBV protein, thymidine kinase (TK) or protein kinase (EBV-PK), for their activity. Therefore, selective induction of EBV lytic-phase gene expression in lymphoma cells that harbor latent EBV, coupled with simultaneous exposure to antiviral drugs, has been advanced as promising targeted therapy, because of resulting targeting of cytotoxicity to the EBV-infected tumor cells.

A variety of agents including short-chain fatty acids and chemotherapeutic drugs, have been used to induce EBV lytic-phase infection in cultured cells, but these in vitro studies have generally not resulted in clinical application. For instance, arginine butyrate and GCV has successfully been used to treat EBV-positive lymphoid malignancies in a recent Phase I/II clinical trial. In this study of 15 patients with relapsed or refractory EBV-positive lymphoid tumors, 4 patients achieved complete tumor remissions and 6 patients partial tumor remissions. However, the rapid metabolism of butyrate requires continuous IV administration of high doses. Butyrate has pan-HDAC inhibitory activity, and it has been established that this activity is responsible for the induction of the EBV-TK protein. HDAC inhibitors have been shown to induce both EBV-TK and EBV-PK in EBV infected tumors.

In recent years, several potent HDAC inhibitors (HDACi) have been tested in the clinic as anticancer agents. In certain instances, HDAC inhibitors, including some new, highly-potent compounds, induce EBV lytic phase gene expression and kill EBV-infected cells in combination with antiviral drugs. In some instances, HDAC inhibitors induce lytic phase gene expression in viruses and kill virus-infected cells in combination with antiviral drugs. HDAC inhibitors include, but are not limited to, short-chain fatty acids (sodium butyrate and valproic acid), hydroxamic acids (Oxamflatin, Scriptaid, CHR-3996, Suberoyl anilide hydroxamic acid (SAHA), Panobinostat (LBH589) and Belinostat (PXD101)), the benzamide MS275, cyclic tetrapeptide Apicidin, and newly-identified HDAC inhibitor Largazole, which was originally isolated from a marine cyanobacterium. In any of the embodiments herein, the HDAC inhibitor is preferably suitable for oral administration.

Methods and Compositions

In one aspect, provided herein are methods for treating and/or preventing a viral condition, a virally-induced condition, or an inflammatory condition. In some embodiments, the condition is associated with a latent viral infection. In certain embodiments, the methods comprise administering a viral inducing agent (e.g., an HDAC inhibitor) and an antiviral agent. In some embodiments, the methods comprise administering an HDAC inhibitor and an antiviral agent. In certain embodiments, the HDAC inhibitor and the antiviral agent are co-formulated. In some embodiments, the methods comprise further administering an additional viral inducing agent. In other embodiments, the methods comprise further administering an additional antiviral agent. In some embodiments, the methods comprise administering additional individual doses of the viral inducing agent and/or the antiviral agent.

Further provided herein are methods for treating and/or preventing a viral condition, a virally-induced condition, or an inflammatory condition comprising administering an HDAC inhibitor. In some embodiments, the HDAC inhibitor is a pyrimidine hydroxamic acid derivative. In certain embodiments, the HDAC inhibitor is a pyrimidine hydroxamic acid derivative not containing a piperidine, or a pyrimidine hydroxamic acid derivative comprising an azabicyclohexane. In certain embodiments, the methods further comprise administering an antiviral agent. In some embodiments, the HDAC inhibitor and the antiviral agent are co-formulated.

Also provided herein are methods for treating and/or preventing a viral or virally-induced condition, or an inflammatory condition comprising administering an HDAC inhibitor and an antiviral agent. In some embodiments, the viral or virally-induced condition is caused by a DNA virus. In certain embodiments, the HDAC inhibitor is administered at a dose of less than 2 mg/kg per dose. In some embodiments, the HDAC inhibitor is administered at a dose of less than 20 mg/kg, less than 19 mg/kg, less than 18 mg/kg, less than 17 mg/kg, less than 16 mg/kg, less than 15 mg/kg, less than 14 mg/kg, less than 13 mg/kg, less than 12 mg/kg, less than 11 mg/kg, less than 10 mg/kg, less than 9 mg/kg, less than 8 mg/kg, less than 7 mg/kg, less than 6 mg/kg, less than 5 mg/kg, less than 4 mg/kg, less than 3 mg/kg, less than 2 mg/kg, less than 1 mg/kg, less than 0.5 mg/kg, less than 0.2 mg/kg, or less than 0.1 mg/kg.

Further provided herein are methods for treating and/or preventing a viral condition, a virally-induced condition, or an inflammatory condition comprising administering an HDAC inhibitor and an antiviral agent wherein the HDAC inhibitor has a molecular weight of greater than 275 g/mol. In some embodiments, the HDAC inhibitor has a molecular weight of greater than 200 g/mol, greater than 225 g/mol, greater than 250 g/mol, greater than 275 g/mol, greater than 300 g/mol, greater than 325 g/mol, greater than 350 g/mol, greater than 375 g/mol, greater than 400 g/mol, greater than 425 g/mol, greater than 450 g/mol, greater than 475 g/mol, greater than 500 g/mol, greater than 525 g/mol, greater than 550 g/mol, greater than 575 g/mol, greater than 600 g/mol, greater than 625 g/mol, greater than 650 g/mol, greater than 675 g/mol, greater than 700 g/mol, greater than 725 g/mol, greater than 750 g/mol, greater than 775 g/mol, greater than 800 g/mol, greater than 850 g/mol, greater than 900 g/mol, greater than 950 g/mol, or greater than 1000 g/mol. In certain embodiments, the HDAC inhibitor has a molecular weight of less than 200 g/mol, less than 225 g/mol, less than 250 g/mol, less than 275 g/mol, less than 300 g/mol, less than 325 g/mol, less than 350 g/mol, less than 375 g/mol, less than 400 g/mol, less than 425 g/mol, less than 450 g/mol, less than 475 g/mol, less than 500 g/mol, less than 525 g/mol, less than 550 g/mol, less than 575 g/mol, less than 600 g/mol, less than 625 g/mol, less than 650 g/mol, less than 675 g/mol, less than 700 g/mol, less than 725 g/mol, less than 750 g/mol, less than 775 g/mol, less than 800 g/mol, less than 850 g/mol, less than 900 g/mol, less than 950 g/mol, or less than 1000 g/mol. In some embodiments, the HDAC inhibitor has a molecular weight of less than 500 g/mol and more than 250 g/mol. In other embodiments, the HDAC inhibitor has a molecular weight of less than 400 g/mol and more than 300 g/mol. In some instances, the HDAC inhibitor is not butyric acid or arginine butyrate.

Also provided herein are methods for treating and/or preventing Epstein-Barr virus (EBV) associated lymphoma. In some embodiments, the methods comprise administering an HDAC inhibitor and acyclovir and/or ganciclovir and/or valganciclovir.

Further provided here are methods for treating and/or preventing a virus-induced inflammatory condition. In some embodiments, the methods comprise administering a viral inducing agent and an antiviral agent. In certain embodiments the virus is a member of the herpes family (e.g., herpes simplex virus, herpes genitalis virus, varicella zoster virus, Epstein-Barr virus, human herpes virus 6, or cytomegalovirus), human immunodeficiency virus, parvovirus, or coxsackie virus.

In another aspect, provided herein are compositions comprising an HDAC inhibitor and an antiviral agent. In certain embodiments, the HDAC inhibitor is a pyrimidine hydroxamic acid derivative. In some embodiments, the HDAC inhibitor is JNJ-26481585, JNJ-16241199, or CHR-3996. In some embodiments, the antiviral agent is acyclovir, ganciclovir, or valganciclovir. In certain embodiments, the composition comprises an additional agent. In some embodiments, the additional agent is a antiviral agent, an HDAC inhibitor, or a chemotherapeutic agent. In certain embodiments, the compositions are formulated as a capsule, gel, tablet, solution, or suspension. In some embodiments, the compositions are formulated for oral administration. In other embodiments, the compositions are formulated for parenteral administration. In some embodiments, the compositions are formulated for intravenous, intraperitoneal, oral, subcutaneous, intrathecal, or intratumoral administration. In certain embodiments, the compositions are formulated for administration at the site of a viral infection. In some embodiments, the compositions are formulated for modified release of the HDAC inhibitor and the antiviral agent. In specific embodiments, the HDAC inhibitor is dissolved before the antiviral agent is dissolved. In other specific embodiments, the HDAC inhibitor is dissolved after the antiviral agent is dissolved. In some embodiments, the compositions are formulated for once daily administration. In other embodiments, the compositions are formulated for twice daily, thrice daily, four times daily, once every other day, once weekly, once bi-weekly, or monthly.

Definitions

The terms "viral," "virus-associated," and "virally-induced" with reference to disorders are used interchangeably throughout the instant specification.

The term "obtaining" as in "obtaining the composition" is intended to include purchasing, synthesizing, or otherwise acquiring the composition (or agent(s) of the composition).

The terms "comprises", "comprising", are intended to have the broad meaning ascribed to them and can mean "includes", "including" and the like.

The term "subject", "patient" or "individual" are used interchangeably herein and refer to mammals and non-mammals, e.g., suffering from a disorder described herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, inhibiting or reducing symptoms, reducing or inhibiting severity of, reducing incidence of, prophylactic treatment of, reducing or inhibiting recurrence of, delaying onset of, delaying recurrence of, abating or ameliorating a disease or condition symptoms, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. By therapeutic benefit is meant eradication or amelioration of the underlying disorder being treated, and/or the eradication or amelioration of one or more of the physiological symptoms associated with the underlying disorder such that an improvement is observed in the patient.

The terms "prevent," "preventing" or "prevention," and other grammatical equivalents as used herein, include preventing additional symptoms, preventing the underlying metabolic causes of symptoms, inhibiting the disease or condition, e.g., arresting the development of the disease or condition and are intended to include prophylaxis. The terms further include achieving a prophylactic benefit. For prophylactic benefit, the compositions are optionally administered to a patient at risk of developing a particular disease, to a patient reporting one or more of the physiological symptoms of a disease, or to a patient at risk of reoccurrence of the disease.

The terms "effective amount" or "therapeutically effective amount" as used herein, refer to a sufficient amount of at least one agent being administered which achieve a desired result, e.g., to relieve to some extent one or more symptoms of a disease or condition being treated. In certain instances, the result is a reduction and/or alleviation of the signs, symptoms, or causes of a disease, or any other desired alteration of a biological system. In certain instances, an "effective amount" for therapeutic uses is the amount of the composition comprising an agent as set forth herein required to provide a clinically significant decrease in a disease. An appropriate "effective" amount in any individual case is determined using any suitable technique, such as a dose escalation study.

The terms "administer," "administering", "administration," and the like, as used herein, refer to the methods that are used to enable delivery of agents or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Administration techniques that in some instances are employed with the agents and methods described herein include, e.g., as discussed in Goodman and Gilman, *The Pharmacological Basis of Therapeutics* (current edition), Pergamon; and Remington's, *Pharmaceutical Sciences* (current edition), Mack Publishing Co., Easton, Pa. In certain embodiments, the agents and compositions described herein are administered orally. In some embodiments, the compositions described herein are administered parenterally.

The term "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material is administered to an individual without causing significant undesirable biological effects or significantly interacting in a deleterious manner with any of the components of the composition in which it is contained.

The term "pharmaceutically acceptable excipient," as used herein, refers to carriers and vehicles that are compatible with the active ingredient (for example, a compound of the invention) of a pharmaceutical composition of the invention (and preferably capable of stabilizing it) and not deleterious to the subject to be treated. For example, solubilizing agents that form specific, more soluble complexes with the compounds of the invention can be utilized as pharmaceutical excipients for delivery of the compounds. Suitable carriers and vehicles are known to those of extraordinary skill in the art. The term "excipient" as used herein will encompass all such carriers, adjuvants, diluents, solvents, or other inactive additives. Suitable pharmaceutically acceptable excipients include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical compositions of the invention can also be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like, which do not deleteriously react with the active compounds of the invention.

The invention can be understood more fully by reference to the following detailed description and illustrative examples, which are intended to exemplify non-limiting embodiments of the invention.

Viral Inducing Agents

The methods of the provided invention comprise use of one or more pharmaceutical compositions provided herein comprising an inducing agent to induce expression of a gene product in a virus-infected cell. The gene product expressed can be a viral enzyme or a cellular enzyme or activity that is largely expressed in virus-infected cells. Expression products that can be targeted include enzymes involved with DNA replication, for example, for repair or replication of the genome, assembly of complete virus particles, generation of viral membrane or walls, RNA transcription or protein translation or combinations of these activities. Interference with these processes can be performed by inducing and then acting on an enzyme and, preferably, a critical enzyme in the process. Inducing agents that can be used in the methods and compositions of the provided invention are described, for example, in U.S. Pat. Nos. 6,197,743 and 6,677,302, which are herein incorporated by reference in their entireties.

Inducing agents according to the methods or compositions provided herein include, without limitation, short-chain fatty acid (SCFA) derivatives, histone deacetylase (HDAC) inhibitors, phorbol esters, anticancer agents, and cytokines. In some embodiments, the viral inducing agent is a chemotherapeutic drug, an HDAC inhibitor, or a DNA demethylating agent.

In some embodiments, the inducing agent is a SCFA derivative. Examples of SCFA inducing agents include propionic acid, butyric acid, succinic acid, fumaric acid monoethyl ester, dimethyl butyric acid, trifluorobutanol, chloropropionic acid, isopropionic acid, 2-oxypentanoic acid, 2,2- or 3,3-dimethyl butyric acid, 2,2- or 3,3-diethyl butyric acid, butyric acid ethyl ester, 2-methyl butanoic acid, fumaric acid, and amides and salts thereof. Other examples include methoxy acetic acid, methoxy propionic acid, N-acetylglycine, mercaptoacetic acid, 1- or 2-methyl cyclopropane carboxylic acid, squaric acid, 2- or 3-phenoxy propionic acid, methoxy butyric acid, phenoxy acetic acid, 2- or 3-phenoxy butyric acid, phenyl acetic acid, phenyl propionic acid, 3-phenyl butyric acid, ethyl-phenyl acetic acid, 4-chloro-2-phenoxy-2-propionic acid, n-dimethyl butyric acid glycine amide, o-benzoyl lactic acid, o-dimethyl butyric acid lactate, cinnamic acid, dihydrocinnamic acid ($C_6 H_5 CHCH_3 COOH$), alpha-methyl-dihydrocinnamic acid, thiophenoxy acetic acid, and amines, amides and salts of these chemicals. Useful amines and amides can include isobutylhydroxylamine, fumaric acid monoamide, fumaramide, succinamide, or isobutyramide.

In other embodiments, inducing agents include retinoic acid, retinol, cytosine arabinoside, phorbols such as the phorbol diester 12-0-tetradecanoylphorbol 13-acetate (TPA), teleocidine B, indole alkaloids, cytotoxin, plant lectins from *Streptomyces*, glucocorticoids such as estrogen and progesterone, phytohemagglutinin (PHA), bryostatin, growth factors (e.g. PDGF, VEGF, EGF, FGF, NGF, TGF, BCGF), anti-sense nucleic acids (e.g. DNA, RNA or PNA), aptamers (nucleic acid oligonucleotides with secondary or tertiary structures which bind with high affinity and selectivity to a target molecule), erythropoietin (EPO), the interleukins (IL-1, IL-2, IL-3, etc.), cAMP and cAMP analogs such as dibutyryl cAMP, activin, inhibin, steel factor, interferon, the bone morphogenic proteins (BMBs), hydroxyurea and dimethyl sulfoxide (DMSO). Other inducing agents include interferons (e.g. α-, β-, γ-interferon), cytokines such as tumor necrosis factor (TNF), cell receptors, and growth factor antagonists, which may be purified or recombinantly produced.

In some embodiments, the inducing agent is a anticancer agent. In certain embodiments, the anticancer agent is a chemotherapeutic anticancer agent. Examples of chemotherapeutic anticancer agents include Nitrogen Mustards like bendamustine, chlorambucil, chlormethine, cyclophosphamide, ifosfamide, melphalan, prednimustine, trofosfamide; Alkyl Sulfonates like busulfan, mannosulfan, treosulfan; Ethylene Imines like carboquone, thiotepa, triaziquone; Nitrosoureas like carmustine, fotemustine, lomustine, nimustine, ranimustine, semustine, streptozocin; Epoxides like etoglucid; Other Alkylating Agents like dacarbazine, mitobronitol, pipobroman, temozolomide; Folic Acid Analogues like methotrexate, permetrexed, pralatrexate, raltitrexed; Purine Analogs like cladribine, clofarabine, fludarabine, mercaptopurine, nelarabine, tioguanine; Pyrimidine Analogs like azacitidine, capecitabine, carmofur, cytarabine, decitabine, fluorouracil, gemcitabine, tegafur; Vinca Alkaloids like vinblastine, vincristine, vindesine, vinflunine, vinorelbine; Podophyllotoxin Derivatives like etoposide, teniposide; Colchicine derivatives like demecolcine; Taxanes like docetaxel, paclitaxel, paclitaxel poliglumex; Other Plant Alkaloids and Natural Products like trabectedin; Actinomycines like dactinomycin; Antracyclines like aclarubicin, daunorubicin, doxorubicin, epirubicin, idarubicin, mitoxantrone, pirarubicin, valrubicin, zorubincin; Other Cytotoxic Antibiotics like bleomycin, ixabepilone, mitomycin, plicamycin; Platinum Compounds like carboplatin, cisplatin, oxaliplatin, satraplatin; Methylhydrazines like procarbazine; Sensitizers like aminolevulinic acid, efaproxiral, methyl aminolevulinate, porfimer sodium, temoporfin; Protein Kinase Inhibitors like dasatinib, erlotinib, everolimus, zotarolimus, gefitinib, imatinib, lapatinib, nilotinib, pazonanib, sorafenib, sunitinib, temsirolimus; Other Antineoplastic Agents like alitretinoin, altretamine, amzacrine, anagrelide, arsenic trioxide, asparaginase, bexarotene, bortezomib, celecoxib, denileukin diftitox, estramustine, hydroxycarbamide, irinotecan, lonidamine, masoprocol, miltefosein, mitoguazone, mitotane, oblimersen, pegaspargase, pentostatin, romidepsin, sitimagene ceradenovec, tiazofurine, topotecan, tretinoin, vorinostat; Estrogens like diethylstilbenol, ethinylestradiol, fosfestrol, polyestradiol phosphate; Progestogens like gestonorone, medroxyprogesterone, megestrol; Gonadotropin Releasing Hormone Analogs like buserelin, goserelin, leuprorelin, triptorelin; Anti-Estrogens like fulvestrant, tamoxifen, toremifene; Anti-Androgens like bicalutamide, flutamide, nilutamide; Enzyme Inhibitors like aminoglutethimide, anastrozole, exemestane, formestane, letrozole, vorozole; Other Hormone Antagonists like abarelix, degarelix; Immunostimulants like histamine dihydrochloride, mifamurtide, pidotimod, plerixafor, roquinimex, thymopentin; Immunosuppressants like everolimus, zotarolimus, gusperimus, leflunomide, mycophenolic acid, sirolimus; Calcineurin Inhibitors like ciclosporin, tacrolimus; Other Immunosuppressants like azathioprine, lenalidomide, methotrexate, thalidomide; and Radiopharmaceuticals like iobenguane.

In certain embodiments, the viral inducing agent is a demethylating agent. For example, demethylating agents include decitabine and azacytidine. In other embodiments, the inducing agent is a chemotherapy drug, such as cyclophosphamide, cisplatin, melphalan, doxorubicin, daunorubicin, vincristine, methotrexate, cytarabine, ifosfamide, etoposide, or rituximab.

In further embodiments, inducing agents include histone deacetylase (HDAC) inhibitors (including those of the hydroxamic acid class and the benzamide class), DNA methyltransferase inhibitors, and proteasome inhibitors. HDAC inhibitors, a class of compounds that interfere with the function of histone deacetylase, include, without limitation, short-chain fatty acids (butyrate, phenylbutyrate, valproate, AN-9, etc., as described above), hydroxamic acids (for example m-carboxycinnamic acid, bishydroxamic acid, suberic bishydroxamic acid, Trichostatin A (7-[4-(dimethylamino)phenyl]-N-hydroxy-4,6-dimethyl-7-oxohepta-2,4-dienamide), SAHA (suberoyl anilide hydroxamic acid)/Vorinostat, oxamflatin, ABHA, SB-55629, pyroxamide, propenamides, aroyl pyrrolyl hydroxamides, Belinostat/PXD101, Papobinostat, LAQ824 (((E)-N-hydroxy-3-[4-[[2-hydroxyethyl-[2-(1H-indol-3-yl)ethyl]amino]methyl]phenyl]prop-2-enamide), LBH589, CHR-3996 (2-(6-{[(6-Fluoroquinolin-2-yl)methyl]amino}-3-azabicyclo[3.1.0]hex-3-yl)-N-hydroxypyrimidine-5-carboxamide, TSA), Pivanex, spiruchostatins, cyclic tetrapeptides (for example, trapoxin A (cyclo((S)-phenylalanyl-(S)-phenylalanyl-(R)-pipecolinyl-(2S,9S)-2-amino-8-oxo-9,10-epoxydecanoyl),), trapoxin B (cyclo((S)-phenylalanyl-phenylalanyl-(R)-prolyl-2-amino-8-oxo-9,10-epoxydecanoyl)), HC-toxin, chlamydocin, diheteropeptin, WF-3161, Cyl-1, Cyl-2, azumamide A), cyclic peptides (for example, FK-228, FR901228), depsipeptides (for example, romidepsin, FK228 ((E)-(1S, 4S,10S,21R)-7[(Z)-ethylideno]-4,21-diisopropyl-2-oxa-12, 13-dithia-5,8,20,23-tetraazabicyclo[8,7,6]-tricos-16-ene-3, 6,9,22-pentanone), FK228 analogs and derivatives, largazole, largazole analogs and derivatives), peptide antibiotics (apicidin), benzamides (MS275 (3-pyridinylmethyl [[4-[[(2-aminophenyl) amino]carbonyl]phenyl]methyl] carbamate, N-(2-Aminophenyl)-4-[N-(pyridine-3ylmethoxycarbonyl)aminomethyl]benzamide), CI994 (4-(Acetylamino)-N-(2-aminophenyl)benzamide), MGCD0103), electrophilic ketones (TPX, AOR, Depudecin), FR901375, nicotinamide, NAD derivatives, Sirtinol, splitomycin, dihydrocoumarin, naphthopyranone, 2-hydroxynaphthaldehydes, PCYC-0402, PCYC-0403, PCI-24781 (3-(dimethylaminomethyl)-N-[2-[4-(hydroxycarbamoyl)phenoxy]ethyl]-1-benzofuran-2-carboxamide), depudecin, tubacin, organosulfur compounds, and dimethyl sulfoxide (DMSO). Other compounds which may also be administered as inducing agents, which include CHAPs, Scriptaid, Tubacin, JNJ16241199, A-161906, 6-(3-Chlorophenylureido)caproic hydroxamic acid, SB939, ITF2357 ({6-[(diethylamino) methyl]-2-naphthyl}methyl {4-[(hydroxyamino)carbonyl] phenyl}carbamate), 4SC-201, AR-42, OPB-801, RG2833, CUDC-101, JNJ-26481585, MK0683 (suberoylanilide hydroxamic acid), M344 (4-(Diethylamino)-N-[7-(hydroxyamino)-7-oxoheptyl]benzamide), BML-210 (N-(2-aminophenyl)-N'-phenyl-octanediamide), dacinostat (NVP-LAQ824), PDX-101, BAY86-5274, SB939, droxinostat, and pivaloyloxymethyl butyrate.

In some embodiments, the viral inducing agent is an HDAC inhibitor. In some embodiments, the HDAC inhibitor is a hydroxamic acid, for example, Vorinostat/suberoyl anilide hydroxamic acid (SAHA), JNJ-26481585 (N-hydroxy-2-(4-((((1-methyl-1H-indol-3-yl)methyl)amino) methyl)piperidin-1-yl)pyrimidine-5-carboxamide), R306465/JNJ-16241199 (N-hydroxy-5-(4-(naphthalen-2-ylsulfonyl)piperazin-1-yl) pyrimidine-2-carboxamide), CHR-3996 (2-(6-{[(6-Fluoroquinolin-2-yl)methyl]amino}-3-azabicyclo[3.1.0]hex-3-yl)-N-hydroxypyrimidine-5-carboxamide), Belinostat/PXD101, Panobinostat/LBH-589, trichostatin A/TSA (7-[4-(dimethylamino)phenyl]-N-hydroxy-4,6-dimethyl-7-oxohepta-2,4-dienamide), ITF2357, CBHA, and Givinostat/ITF2357. In certain embodiments, the HDAC inhibitor is a pyrimidine hydroxamic acid, for example, JNJ-26481585, JNJ-16241199, or CHR-3996. In other embodiments, the HDAC inhibitor is a benzamide, for example, CI-994, Entinostat/MS-275, SNDX-275, and mocetinostat/MGCD0103 (N-(2-aminophenyl)-4-((4-pyridin-3-ylpyrimidin-2-ylamino)methyl)benzamide).

In some embodiments, the HDAC inhibitor is a hydroxamic acid derivative. In certain embodiments, the HDAC inhibitor is a pyrimidine hydroxamic acid. In some embodiments, the HDAC inhibitor is a non-piperidine-containing pyrimidine hydroxamic acid derivative. In certain embodiments, the HDAC inhibitor comprises an azabicyclo-hexane. In other embodiments, the HDAC inhibitor comprises fluorine. In certain embodiments, the HDAC inhibitor comprises a fluoroquinoline group.

In one embodiment the HDAC inhibitor is JNJ-26481585 (N-hydroxy-2-(4-((((1-methyl-1H-indol-3-yl)methyl) amino)methyl)piperidin-1-yl)pyrimidine-5-carboxamide). In a further embodiment, the HDAC inhibitor is R306465/ JNJ-16241199 (N-hydroxy-5-(4-(naphthalen-2-ylsulfonyl) piperazin-1-yl)pyrimidine-2-carboxamide). In a specific embodiment, the HDAC inhibitor is CHR-3996 [2-(6-{[(6-Fluoroquinolin-2-yl) methyl]amino}-3-azabicyclo[3.1.0] hex-3-yl)-N-hydroxypyrimidine-5-carboxamide, or N-hydroxy 2-(6-{[(6-Fluoroquinolin-2-yl)methyl]amino}-3-azabicyclo[3.1.0]hex-3-yl)-pyrimidine-5-carboxamide].

In another embodiment, the molecular weight of the HDAC inhibitor is greater than 275 g/mol. In some embodiments, the HDAC inhibitor has a molecular weight of greater than 200 g/mol, greater than 225 g/mol, greater than 250 g/mol, greater than 275 g/mol, greater than 300 g/mol, greater than 325 g/mol, greater than 350 g/mol, greater than 375 g/mol, greater than 400 g/mol, greater than 425 g/mol, greater than 450 g/mol, greater than 475 g/mol, greater than 500 g/mol, greater than 525 g/mol, greater than 550 g/mol, greater than 575 g/mol, greater than 600 g/mol, greater than 625 g/mol, greater than 650 g/mol, greater than 675 g/mol, greater than 700 g/mol, greater than 725 g/mol, greater than 750 g/mol, greater than 775 g/mol, greater than 800 g/mol, greater than 850 g/mol, greater than 900 g/mol, greater than 950 g/mol, or greater than 1000 g/mol. In certain embodiments, the HDAC inhibitor has a molecular weight of less than 200 g/mol, less than 225 g/mol, less than 250 g/mol, less than 275 g/mol, less than 300 g/mol, less than 325 g/mol, less than 350 g/mol, less than 375 g/mol, less than 400 g/mol, less than 425 g/mol, less than 450 g/mol, less than 475 g/mol, less than 500 g/mol, less than 525 g/mol, less than 550 g/mol, less than 575 g/mol, less than 600 g/mol, less than 625 g/mol, less than 650 g/mol, less than 675 g/mol, less than 700 g/mol, less than 725 g/mol, less than 750 g/mol, less than 775 g/mol, less than 800 g/mol, less than 850 g/mol, less than 900 g/mol, less than 950 g/mol, or less than 1000 g/mol. In some embodiments, the HDAC inhibitor has a molecular weight of less than 500 g/mol and more than 250 g/mol. In other embodiments, the HDAC inhibitor has a molecular weight of less than 400 g/mol and more than 300 g/mol.

In a particular embodiment, the HDAC inhibitor is not m-carboxycinnamic acid, bishydroxamic acid, suberic bishydroxamic acid, Trichostatin A (7-[4-(dimethylamino)phenyl]-N-hydroxy-4,6-dimethyl-7-oxohepta-2,4-dienamide), SAHA (suberoyl anilide hydroxamic acid)/Vorinostat, oxamflatin, ABHA, SB-55629, pyroxamide, propenamides, aroyl pyrrolyl hydroxamides, Belinostat/PXD101, Papobinostat, LAQ824 (((E)-N-hydroxy-3-[4-[[2-hydroxyethyl-[2-(1H-indol-3-yl)ethyl]amino]methyl]phenyl]prop-2-enamide), or LBH589.

In some embodiments, a viral inducing agent, for example an HDAC inhibitor, penetrates the blood brain barrier. In certain embodiments, a viral inducing agent that penetrates the blood brain barrier comprises arginine butyrate, SAHA, or CHR-3996.

In certain embodiments, the HDAC inhibitor is administered at a dose of less than 400 mg/day. In some embodiments, the HDAC inhibitor is administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, about 100 mg/day, about 120 mg/day, about 125 mg/day, about 140 mg/day, about 150 mg/day, about 160 mg/day, about 175 mg/day, about 180 mg/day, about 190 mg/day, about 200 mg/day, about 225 mg/day, about 250 mg/day, about 275 mg/day, about 300 mg/day, about 325 mg/day, about 350 mg/day, about 375 mg/day, about 400 mg/day, about 425 mg/day, about 450 mg/day, about 475 mg/day, or about 500 mg/day. In certain embodiments, the HDAC inhibitor is administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, less than 100 mg/day, less than 120 mg/day, less than 125 mg/day, less than 140 mg/day, less than 150 mg/day, less than 160 mg/day, less than 175 mg/day, less than 180 mg/day, less than 190 mg/day, less than 200 mg/day, less than 225 mg/day, less than 250 mg/day, less than 275 mg/day, less than 300 mg/day, less than 325 mg/day, less than 350 mg/day, less than 375 mg/day, less than 400 mg/day, less than 425 mg/day, less than 450 mg/day, less than 475 mg/day, or less than 500 mg/day. In some embodiments, the HDAC inhibitor is administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, more than 100 mg/day, more than 120 mg/day, more than 125 mg/day, more than 140 mg/day, more than 150 mg/day, more than 160 mg/day, more than 175 mg/day, more than 180 mg/day, more than 190 mg/day, more than 200 mg/day, more than 225 mg/day, more than 250 mg/day, more than 275 mg/day, more than 300 mg/day, more than 325 mg/day, more than 350 mg/day, more than 375 mg/day, more than 400 mg/day, more than 425 mg/day, more than 450 mg/day, more than 475 mg/day, or more than 500 mg/day. In certain embodiments, the HDAC inhibitor is administered at a dose of more than 1 mg/day and less than 500 mg/day. In some embodiments, the HDAC inhibitor is administered at a dose of more than 20 mg/day and less than 80 mg/day. In certain embodiments, the HDAC inhibitor is administered once a day (q.d.), twice a day (b.id.), or thrice a day (t.i.d.). In some embodiments, the HDAC inhibitor is administered daily, once a week, twice a week, three times a week, four times a week, or five times a week.

In some embodiments, the HDAC inhibitor is CHR-3996. In certain embodiments, CHR-3996 is administered at a dose of 40 mg/day. In some embodiments, CHR-3996 is administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, or about 100 mg/day. In certain embodiments, CHR-3996 is administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, or less than 100 mg/day. In some embodiments, CHR-3996 is administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, or more than 100 mg/day. In certain embodiments, CHR-3996 is administered at a dose of more than 30 mg/day and less than 50 mg/day. In some embodiments, CHR-3996 is administered at a dose of more than 20 mg/day and less than 80 mg/day. In certain embodiments, CHR-3996 is administered once a day (q.d.), twice a day (b.id.), or thrice a day (t.i.d.). In some embodiments, CHR-3996 is administered daily, once a week, twice a week, three times a week, four times a week, or five times a week.

In some embodiments, a unit dose of a co-formulated HDAC inhibitor and antiviral agent comprises less than 100 mg of the HDAC inhibitor and less than 1000 mg of the antiviral agent. In certain embodiments, the unit dose comprises less than 50 mg of the HDAC inhibitor and less than 500 mg of the antiviral agent. In other embodiments, the unit dose comprises less than 80 mg of the HDAC inhibitor and less than 1500 mg of the antiviral agent. In some embodiments, the unit dose comprises less than 50 mg of the HDAC inhibitor CHR-3996 and less than 1000 mg of valganciclovir. In some embodiments, the unit dose comprises about 20 mg of the HDAC inhibitor CHR-3996 and about 450 mg of valganciclovir. In certain embodiments, the unit dose comprises about 40 mg of the HDAC inhibitor CHR-3996 and about 900 mg of valganciclovir. In some embodiments, the antiviral agent is formulated as controlled release.

In some embodiments, the HDAC inhibitor is ITF-2357. In certain embodiments, ITF-2357 is administered at a dose of 100 mg/day. In some embodiments, ITF-2357 is administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, about 100 mg/day, about 120 mg/day, about 125 mg/day, about 140 mg/day, about 150 mg/day, about 160 mg/day, about 175 mg/day, about 180 mg/day, about 200 mg/day, about 225 mg/day, about 250 mg/day, about 275 mg/day, or about 300 mg/day. In certain embodiments, ITF-2357 is administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, less than 100 mg/day, less than 120 mg/day, less than 125 mg/day, less than 140 mg/day, less than 150 mg/day, less than 160 mg/day, less than 175 mg/day, less than 180 mg/day, less than 200 mg/day, less than 225 mg/day, less than 250 mg/day, less than 275 mg/day, or less than 300 mg/day. In some embodiments, ITF-2357 is administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, more than 100 mg/day, more than 120 mg/day, more than 125 mg/day, more than 140 mg/day, more than 150 mg/day, more than 160 mg/day, more than 175 mg/day, more than 180 mg/day, more than 200 mg/day, more than 225 mg/day, more than 250 mg/day, more than 275 mg/day, or more than 300 mg/day. In certain embodiments, ITF-2357 is administered at a dose of more than 80 mg/day and less than 120 mg/day. In some embodiments, ITF-2357 is administered at a dose of more than 40 mg/day and less than 120 mg/day. In certain embodiments, ITF-2357 is administered at a dose of more than 50 mg/day and less than 240 mg/day. In some embodiments, ITF-2357 is administered once a day (q.d.), twice a day (b.id.), or thrice a day (t.i.d.). In some embodiments, ITF-2357 is administered daily, once a week, twice a week, three times a week, four times a week, or five times a week.

In some embodiments, the HDAC inhibitor is JNJ-16241199/R306465. In certain embodiments, JNJ-16241199/R306465 is administered at a dose of 100 mg/day. In some embodiments, JNJ-16241199/R306465 is administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, about 100 mg/day, about 120 mg/day, about 125 mg/day, about 140 mg/day, about 150 mg/day, about 160 mg/day, about 175 mg/day, about 180 mg/day, about 200 mg/day, about 225 mg/day, about 250 mg/day, about 275 mg/day, or about 300 mg/day. In certain embodiments, JNJ-16241199/R306465 is administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, less than 100 mg/day, less than 120 mg/day, less than 125 mg/day, less than 140 mg/day, less than 150 mg/day, less than 160 mg/day, less than 175 mg/day, less than 180 mg/day, less than 200 mg/day, less than 225 mg/day, less than 250 mg/day, less than 275 mg/day, or less than 300 mg/day. In some embodiments, JNJ-16241199/R306465 is administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, more than 100 mg/day, more than 120 mg/day, more than 125 mg/day, more than 140 mg/day, more than 150 mg/day, more than 160 mg/day, more than 175 mg/day, more than 180 mg/day, more than 200 mg/day, more than 225 mg/day, more than 250 mg/day, more than 275 mg/day, or more than 300 mg/day. In certain embodiments, JNJ-16241199/R306465 is administered at a dose of more than 80 mg/day and less than 120 mg/day. In some embodiments, JNJ-16241199/R306465 is administered at a dose of more than 40 mg/day and less than 120 mg/day. In certain embodiments, JNJ-16241199/R306465 is administered at a dose of more than 50 mg/day and less than 240 mg/day. In some embodiments, JNJ-16241199/R306465 is administered once a day (q.d.), twice a day (b.id.), or thrice a day (t.i.d.). In some embodiments, JNJ-16241199/R306465 is administered daily, once a week, twice a week, three times a week, four times a week, or five times a week.

In some embodiments, the HDAC inhibitor is JNJ-26481585. In certain embodiments, JNJ-26481585 is administered at a dose of 10 mg/day. In some embodiments, JNJ-26481585 is administered at a dose of about 0.1 mg/day, about 0.2 mg/day, about 0.5 mg/day, about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, or about 100 mg/day. In certain embodiments, JNJ-26481585 is administered at a dose of less than 0.1 mg/day, less than 0.2 mg/day, less than 0.5 mg/day, less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, or less than 100 mg/day. In some embodiments, JNJ-26481585 is administered at a dose of more than 0.1 mg/day, more than 0.2 mg/day, more than 0.5 mg/day, more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, or more than 100 mg/day. In certain embodiments, JNJ-26481585 is administered at a dose of more than 2 mg/day and less than 20 mg/day. In some embodiments, JNJ-26481585 is administered at a dose of more than 5 mg/day and less than 30 mg/day. In certain embodiments, JNJ-26481585 is administered once a day (q.d.), twice a day (b.id.), or thrice a day (t.i.d.). In some embodiments, JNJ-26481585 is administered daily, once a week, twice a week, three times a week, four times a week, or five times a week.

In some embodiments, the HDAC inhibitor is MGCD103. In certain embodiments, MGCD103 is administered at a dose of 45 mg/m$^2$/day. In some embodiments, MGCD103 is administered at a dose of about 1 mg/m$^2$/day, about 2 mg/m$^2$/day, about 5 mg/m$^2$/day, about 10 mg/m$^2$/day, about 15 mg/m$^2$/day, about 20 mg/m$^2$/day, about 25 mg/m$^2$/day, about 30 mg/m$^2$/day, about 35 mg/m$^2$/day, about 40 mg/m2/day, about 45 mg/m$^2$/day, about 50 mg/m$^2$/day, about 60 mg/m$^2$/day, about 70 mg/m$^2$/day, about 80 mg/m$^2$/day, about 90 mg/m$^2$/day, or about 100 mg/m$^2$/day. In certain embodiments, MGCD103 is administered at a dose of less than 1 mg/m$^2$/day, less than 2 mg/m$^2$/day, less than 5 mg/m$^2$/day, less than 10 mg/m$^2$/day, less than 15 mg/m$^2$/day, less than 20 mg/m$^2$/day, less than 25 mg/m$^2$/day, less than 30 mg/m$^2$/day, less than 35 mg/m$^2$/day, less than 40 mg/m$^2$/day, less than 45 mg/m$^2$/day, less than 50 mg/m$^2$/day, less than 60 mg/m$^2$/day, less than 70 mg/m$^2$/day, less than 80 mg/m$^2$/day, less than 90 mg/m$^2$/day, or less than 100 mg/m$^2$/day. In some embodiments, MGCD103 is administered at a dose of more than 1 mg/m$^2$/day, more than 2 mg/m$^2$/day, more than 5 mg/m$^2$/day, more than 10 mg/m$^2$/day, more than 15 mg/m$^2$/day, more than 20 mg/m$^2$/day, more than 25 mg/m$^2$/day, more than 30 mg/m$^2$/day, more than 35 mg/m$^2$/day, more than 40 mg/m$^2$/day, more than 45 mg/m$^2$/day, more than 50 mg/m$^2$/day, more than 60 mg/m$^2$/day, more than 70 mg/m$^2$/day, more than 80 mg/m$^2$/day, more than 90 mg/m$^2$/day, or more than 100 mg/m$^2$/day. In certain embodiments, MGCD103 is administered at a dose of more than 30 mg/m$^2$/day and less than 80 mg/m$^2$/day. In some embodiments, MGCD103 is administered at a dose of more than 45 mg/m$^2$/day and less than 60 mg/m$^2$/day. In certain embodiments, MGCD103 is administered once a day (q.d.), twice a day (b.id.), or thrice a day (t.i.d.). In some embodiments, MGCD103 is administered daily, once a week, twice a week, three times a week, four times a week, or five times a week.

In some embodiments, the HDAC inhibitor is MS-275. In certain embodiments, MS-275 is administered at a dose of 4 mg/m$^2$/day. In some embodiments, MS-275 is administered at a dose of about 0.1 mg/m$^2$/day, of about 0.2 mg/m$^2$/day, of about 0.5 mg/m$^2$/day, of about 1 mg/m$^2$/day, of about 2 mg/m$^2$/day, of about 3 mg/m$^2$/day, of about 4 mg/m$^2$/day, about 5 mg/m$^2$/day, of about 6 mg/m$^2$/day, of about 7 mg/m$^2$/day, of about 8 mg/m$^2$/day, of about 9 mg/m$^2$/day, about 10 mg/m$^2$/day, about 15 mg/m$^2$/day, about 20 mg/m$^2$/day, about 25 mg/m$^2$/day, about 30 mg/m$^2$/day, about 35 mg/m$^2$/day, about 40 mg/m2/day, about 45 mg/m$^2$/day, about 50 mg/m$^2$/day, about 60 mg/m$^2$/day, about 70 mg/m$^2$/day, about 80 mg/m$^2$/day, about 90 mg/m$^2$/day, or about 100 mg/m$^2$/day. In certain embodiments, MS-275 is administered at a dose of less than 0.1 mg/m$^2$/day, of less than 0.2 mg/m$^2$/day, of less than 0.5 mg/m$^2$/day, of less than 1 mg/m$^2$/day, of less than 2 mg/m$^2$/day, of less than 3 mg/m$^2$/day, of less than 4 mg/m$^2$/day, less than 5 mg/m$^2$/day, of less than 6 mg/m$^2$/day, of less than 7 mg/m$^2$/day, of less than 8 mg/m$^2$/day, of less than 9 mg/m$^2$/day, less than 10 mg/m$^2$/day, less than 15 mg/m$^2$/day, less than 20 mg/m$^2$/day, less than 25 mg/m$^2$/day, less than 30 mg/m$^2$/day, less than 35 mg/m$^2$/day, less than 40 mg/m2/day, less than 45 mg/m$^2$/day, less than 50 mg/m$^2$/day, less than 60 mg/m$^2$/day, less than 70 mg/m$^2$/day, less than 80 mg/m$^2$/day, less than 90 mg/m$^2$/day, or less than 100 mg/m$^2$/day. In some embodiments, MS-275 is administered at a dose of more than 0.1 mg/m$^2$/day, of more than 0.2 mg/m$^2$/day, of more than 0.5 mg/m$^2$/day, of more than 1 mg/m$^2$/day, of more than 2 mg/m$^2$/day, of more than 3 mg/m$^2$/day, of more than 4 mg/m$^2$/day, more than 5 mg/m$^2$/day, of more than 6 mg/m$^2$/day, of more than 7 mg/m$^2$/day, of more than 8 mg/m$^2$/day, of more than 9 mg/m$^2$/day, more than 10 mg/m$^2$/day, more than 15 mg/m$^2$/day, more than 20 mg/m$^2$/day, more than 25 mg/m$^2$/day, more than 30 mg/m$^2$/day, more than 35 mg/m$^2$/day, more than 40 mg/m2/day, more than 45 mg/m$^2$/day, more than 50 mg/m$^2$/day, more than 60 mg/m$^2$/day, more than 70 mg/m$^2$/day, more than 80 mg/m$^2$/day, more than 90 mg/m$^2$/day, or more than 100 mg/m$^2$/day. In certain embodiments, MS-275 is administered at a dose of more than 2 mg/m$^2$/day and less than 10 mg/m$^2$/day. In some embodiments, MS-275 is administered at a dose of more than 2 mg/m$^2$/day and less than 40 mg/m$^2$/day. In certain embodiments, MS-275 is administered at a dose of more than 2 mg/m$^2$/day and less than 6 mg/m$^2$/day. In some embodiments, MS-275 is administered at a dose of more than 6 mg/m$^2$/day and less than 8 mg/m$^2$/day. In certain embodiments, MS-275 is administered once a day (q.d.), twice a day (b.id.), or thrice a day (t.i.d.). In some embodiments, MS-275 is administered daily, once a week, twice a week, three times a week, four times a week, or five times a week.

In some embodiments, the HDAC inhibitor is SB939. In certain embodiments, SB939 is administered at a dose of 60 mg/day. In some embodiments, SB939 is administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, about 100 mg/day, about 120 mg/day, about 125 mg/day, about 140 mg/day, about 150 mg/day, about 160 mg/day, about 175 mg/day, about 180 mg/day, or about 200 mg/day. In certain embodiments, SB939 is administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, less than 100 mg/day, less than 120 mg/day, less than 125 mg/day, less than 140 mg/day, less than 150 mg/day, less than 160 mg/day, less than 175 mg/day, less than 180 mg/day, or less than 200 mg/day. In some embodiments, SB939 is administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, more than 100 mg/day, more than 120 mg/day, more than 125 mg/day, more than 140 mg/day, more than 150 mg/day, more than 160 mg/day, more than 175 mg/day, more than 180 mg/day, or more than 200 mg/day. In certain embodiments, SB939 is administered at a dose of more than 30 mg/day and less than 70 mg/day. In some embodiments, SB939 is administered at a dose of more than 10 mg/day and less than 90 mg/day. In certain embodiments, SB939 is administered once a day (q.d.), twice a day (b.id.), or thrice a day (t.i.d.). In some embodiments, SB939 is administered daily, once a week, twice a week, three times a week, four times a week, or five times a week.

In some embodiments, the HDAC inhibitor is romidepsin. In certain embodiments, romidepsin is administered at a dose of 14 mg/m$^2$/day. In some embodiments, romidepsin is administered at a dose of about 0.1 mg/m$^2$/day, of about 0.2 mg/m$^2$/day, of about 0.5 mg/m$^2$/day, of about 1 mg/m$^2$/day, of about 2 mg/m$^2$/day, of about 3 mg/m$^2$/day, of about 4 mg/m$^2$/day, about 5 mg/m$^2$/day, of about 6 mg/m$^2$/day, of about 7 mg/m$^2$/day, of about 8 mg/m$^2$/day, of about 9 mg/m$^2$/day, about 10 mg/m$^2$/day, about 11 mg/m$^2$/day, about 12 mg/m$^2$/day, about 13 mg/m$^2$/day, about 14 mg/m$^2$/day, about 15 mg/m$^2$/day, about 16 mg/m$^2$/day, about 17 mg/m$^2$/day, about 18 mg/m$^2$/day, about 19 mg/m$^2$/day, about 20 mg/m$^2$/day, about 25 mg/m$^2$/day, about 30 mg/m$^2$/day, about 35 mg/m$^2$/day, about 40 mg/m2/day, about 45 mg/m$^2$/day, about 50 mg/m$^2$/day, about 60 mg/m$^2$/day, about 70 mg/m$^2$/day, about 80 mg/m$^2$/day, about 90 mg/m$^2$/day, or about 100 mg/m$^2$/day. In certain embodiments, romidepsin is administered at a dose of less than 0.1 mg/m$^2$/day, of less than 0.2 mg/m$^2$/day, of less than 0.5 mg/m$^2$/day, of less than 1 mg/m$^2$/day, of less than 2 mg/m$^2$/day, of less than 3 mg/m$^2$/day, of less than 4 mg/m$^2$/day, less than 5 mg/m$^2$/day, of less than 6 mg/m$^2$/day, of less than 7 mg/m$^2$/day, of less than 8 mg/m$^2$/day, of less than 9 mg/m$^2$/day, less than 10 mg/m$^2$/day, less than 11 mg/m$^2$/day, less than 12 mg/m$^2$/day, less than 13 mg/m$^2$/day, less than 14 mg/m$^2$/day, less than 15 mg/m$^2$/day, less than 16 mg/m$^2$/day, less than 17 mg/m$^2$/day, less than 18 mg/m$^2$/day, less than 19 mg/m$^2$/day, less than 20 mg/m$^2$/day, less than 25 mg/m$^2$/day, less than 30 mg/m$^2$/day, less than 35 mg/m$^2$/day, less than 40 mg/m2/day, less than 45 mg/m$^2$/day, less than 50 mg/m$^2$/day, less than 60 mg/m$^2$/day, less than 70 mg/m$^2$/day, less than 80 mg/m$^2$/day, less than 90 mg/m$^2$/day, or less than 100 mg/m$^2$/day. In some embodiments, romidepsin is administered at a dose of more than 0.1 mg/m$^2$/day, of more than 0.2 mg/m$^2$/day, of more than 0.5 mg/m$^2$/day, of more than 1 mg/m$^2$/day, of more than 2 mg/m$^2$/day, of more than 3 mg/m$^2$/day, of more than 4 mg/m$^2$/day, more than 5 mg/m$^2$/day, of more than 6 mg/m$^2$/day, of more than 7 mg/m$^2$/day, of more than 8 mg/m$^2$/day, of more than 9 mg/m$^2$/day, more than 10 mg/m$^2$/day, more than 11 mg/m$^2$/day, more than 12 mg/m$^2$/day, more than 13 mg/m$^2$/day, more than 14 mg/m$^2$/day, more than 15 mg/m$^2$/day, more than 16 mg/m$^2$/day, more than 17 mg/m$^2$/day, more than 18 mg/m$^2$/day, more than 19 mg/m$^2$/day, more than 20 mg/m$^2$/day, more than 25 mg/m$^2$/day, more than 30 mg/m$^2$/day, more than 35 mg/m$^2$/day, more than 40 mg/m2/day, more than 45 mg/m$^2$/day, more than 50 mg/m$^2$/day, more than 60 mg/m$^2$/day, more than 70 mg/m$^2$/day, more than 80 mg/m$^2$/day, more than 90 mg/m$^2$/day, or more than 100 mg/m$^2$/day. In certain embodiments, romidepsin is administered at a dose of more than 13 mg/m$^2$/day and less than 18 mg/m$^2$/day. In some embodiments, romidepsin is administered at a dose of more than 10 mg/m$^2$/day and less than 20 mg/m$^2$/day. In certain embodiments, romidepsin is administered once a day (q.d.), twice a day (b.id.), or thrice a day (t.i.d.). In some embodiments, romidepsin is administered daily, once a week, twice a week, three times a week, four times a week, or five times a week.

In some embodiments, the HDAC inhibitor is LBH589. In certain embodiments, LBH589 is administered at a dose of 20 mg/day. In some embodiments, LBH589 is administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, or about 100 mg/day. In certain embodiments, LBH589 is administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, or less than 100 mg/day. In some embodiments, LBH589 is administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, or more than 100 mg/day. In certain embodiments, LBH589 is administered at a dose of more than 10 mg/day and less than 20 mg/day. In some embodiments, LBH589 is administered at a dose of more than 5 mg/day and less than 30 mg/day. In certain embodiments, LBH589 is administered once a day (q.d.), twice a day (b.id.), or thrice a day (t.i.d.). In some embodiments, LBH589 is administered daily, once a week, twice a week, three times a week, four times a week, or five times a week.

In some embodiments, the HDAC inhibitor is PXD101. In certain embodiments, PXD101 is administered at a dose of 1000 mg/m$^2$/day. In some embodiments, PXD101 is administered at a dose of about 10 mg/m$^2$/day, about 15 mg/m$^2$/day, about 20 mg/m$^2$/day, about 50 mg/m$^2$/day, about 75 mg/m$^2$/day, about 100 mg/m$^2$/day, about 150 mg/m$^2$/day, about 200 mg/m$^2$/day, about 300 mg/m$^2$/day, about 400 mg/m$^2$/day, about 500 mg/m$^2$/day, about 600 mg/m$^2$/day, about 700 mg/m$^2$/day, about 800 mg/m$^2$/day, about 900 mg/m²/day, about 1000 mg/m²/day, about 1100 mg/m²/day, about 1200 mg/m²/day, about 1300 mg/m²/day, about 1400 mg/m²/day, about 1500 mg/m²/day, about 1750 mg/m²/day, or about 2000 mg/m²/day. In certain embodiments, PXD101 is administered at a dose of less than 10 mg/m²/day, less than 15 mg/m²/day, less than 20 mg/m²/day, less than 50 mg/m²/day, less than 75 mg/m²/day, less than 100 mg/m²/day, less than 150 mg/m²/day, less than 200 mg/m²/day, less than 300 mg/m²/day, less than 400 mg/m²/day, less than 500 mg/m²/day, less than 600 mg/m²/day, less than 700 mg/m²/day, less than 800 mg/m²/day, less than 900 mg/m²/day, less than 1000 mg/m²/day, less than 1100 mg/m²/day, less than 1200 mg/m²/day, less than 1300 mg/m²/day, less than 1400 mg/m²/day, less than 1500 mg/m²/day, less than 1750 mg/m²/day, or less than 2000 mg/m²/day. In some embodiments, PXD101 is administered at a dose of more than 10 mg/m²/day, more than 15 mg/m²/day, more than 20 mg/m²/day, more than 50 mg/m²/day, more than 75 mg/m²/day, more than 100 mg/m²/day, more than 150 mg/m²/day, more than 200 mg/m²/day, more than 300 mg/m²/day, more than 400 mg/m²/day, more than 500 mg/m²/day, more than 600 mg/m²/day, more than 700 mg/m²/day, more than 800 mg/m²/day, more than 900 mg/m²/day, more than 1000 mg/m²/day, more than 1100 mg/m²/day, more than 1200 mg/m²/day, more than 1300 mg/m²/day, more than 1400 mg/m²/day, more than 1500 mg/m²/day, more than 1750 mg/m²/day, or more than 2000 mg/m²/day. In certain embodiments, PXD101 is administered at a dose of more than 600 mg/m²/day and less than 1000 mg/m²/day. In some embodiments, PXD101 is administered at a dose of more than 15 mg/m²/day and less than 1000 mg/m²/day. In certain embodiments, PXD101 is administered once a day (q.d.), twice a day (b.id.), or thrice a day (t.i.d.). In some embodiments, PXD101 is administered daily, once a week, twice a week, three time a week, four times a week, or five times a week.

In some embodiments, the HDAC inhibitor is vorinostat. In certain embodiments, vorinostat is administered at a dose of 400 mg/day. In some embodiments, vorinostat is administered at a dose of about 10 mg/day, about 20 mg/day, about 30 mg/day, about 40 mg/day, about 50 mg/day, about 60 mg/day, about 70 mg/day, about 80 mg/day, about 90 mg/day, about 100 mg/day, about 125 mg/day, about 150 mg/day, about 175 mg/day, about 200 mg/day, about 225 mg/day, about 250 mg/day, about 275 mg/day, about 300 mg/day, about 325 mg/day, about 350 mg/day, about 375 mg/day, about 400 mg/day, about 450 mg/day, about 500 mg/day, about 550 mg/day, about 600 mg/day, about 650 mg/day, about 700 mg/day, about 750 mg/day, about 800 mg/day, about 900 mg/day, or about 1000 mg/day. In certain embodiments, vorinostat is administered at a dose of less than 10 mg/day, less than 20 mg/day, less than 30 mg/day, less than 40 mg/day, less than 50 mg/day, less than 60 mg/day, less than 70 mg/day, less than 80 mg/day, less than 90 mg/day, less than 100 mg/day, less than 125 mg/day, less than 150 mg/day, less than 175 mg/day, less than 200 mg/day, less than 225 mg/day, less than 250 mg/day, less than 275 mg/day, less than 300 mg/day, less than 325 mg/day, less than 350 mg/day, less than 375 mg/day, less than 400 mg/day, less than 450 mg/day, less than 500 mg/day, less than 550 mg/day, less than 600 mg/day, less than 650 mg/day, less than 700 mg/day, less than 750 mg/day, less than 800 mg/day, less than 900 mg/day, or less than 1000 mg/day. In some embodiments, vorinostat is administered at a dose of more than 10 mg/day, more than 20 mg/day, more than 30 mg/day, more than 40 mg/day, more than 50 mg/day, more than 60 mg/day, more than 70 mg/day, more than 80 mg/day, more than 90 mg/day, more than 100 mg/day, more than 125 mg/day, more than 150 mg/day, more than 175 mg/day, more than 200 mg/day, more than 225 mg/day, more than 250 mg/day, more than 275 mg/day, more than 300 mg/day, more than 325 mg/day, more than 350 mg/day, more than 375 mg/day, more than 400 mg/day, more than 450 mg/day, more than 500 mg/day, more than 550 mg/day, more than 600 mg/day, more than 650 mg/day, more than 700 mg/day, more than 750 mg/day, more than 800 mg/day, more than 900 mg/day, or more than 1000 mg/day. In certain embodiments, vorinostat is administered at a dose of more than 100 mg/day and less than 400 mg/day. In some embodiments, vorinostat is administered at a dose of more than 100 mg/day and less than 500 mg/day. In certain embodiments, vorinostat is administered once a day (q.d.), twice a day (b.id.), or thrice a day (t.i.d.). In some embodiments, vorinostat is administered daily, once a week, twice a week, three times a week, four times a week, or five times a week.

In some embodiments, an HDAC inhibitor inhibits the growth of virus-positive cells. In certain embodiments, the HDAC inhibitor inhibits the growths of EBV-positive lymphoma cells. In some embodiments, the HDAC inhibitor has growth inhibitory activity at a concentration of about 100 µM, about 90 µM, about 80 µM, about 75 µM, about 70 µM, about 60 µM, about 50 µM, about 40 µM, about 30 µM, about 25 µM, about 20 µM, about 10 µM, about 5 µM, about 2 µM, about 1 µM, about 900 nM, about 800 nM, about 700 nM, about 600 nM, about 500 nM, about 400 nM, about 300 nM, about 200 nM, about 100 nM, about 75 nM, about 50 nM, about 20 nM, or about 10 nM. In certain embodiments, the HDAC inhibitor has growth inhibitory activity at a concentration of less than 100 µM, less than 90 µM, less than 80 µM, less than 75 µM, less than 70 µM, less than 60 µM, less than 50 µM, less than 40 µM, less than 30 µM, less than 25 µM, less than 20 µM, less than 10 µM, less than 5 µM, less than 2 µM, less than 1 µM, less than 900 nM, less than 800 nM, less than 700 nM, less than 600 nM, less than 500 nM, less than 400 nM, less than 300 nM, less than 200 nM, less than 100 nM, less than 75 nM, less than 50 nM, less than 20 nM, or less than 10 nM. In some embodiments, the HDAC inhibitor has growth inhibitory activity at a concentration of more than 100 µM, more than 90 µM, more than 80 µM, more than 75 µM, more than 70 µM, more than 60 µM, more than 50 µM, more than 40 µM, more than 30 µM, more than 25 µM, more than 20 µM, more than 10 µM, more than 5 µM, more than 2 µM, more than 1 µM, more than 900 nM, more than 800 nM, more than 700 nM, more than 600 nM, more than 500 nM, more than 400 nM, more than 300 nM, more than 200 nM, more than 100 nM, more than 75 nM, more than 50 nM, more than 20 nM, or more than 10 nM. In certain embodiments, the HDAC inhibitor has growth inhibitory activity at more than 50 nM and less than 100 nM. In some embodiments, the HDAC inhibitor has growth inhibitory activity at more than 200 nM and less than 500 nM. In certain embodiments, the HDAC inhibitor has growth inhibitory activity at more than 100 nM and less than 200 nM.

Induced Genes Including Viral-Associated Genes

Inducing agents (agents that induce expression) may act directly on the viral genome or indirectly through a cellular factor required for viral expression. For example, viral gene expression can be regulated through the regulation of the expression of viral transcription factors such as ZTA, RTA, tat, and tax, cellular transcription factors such as AP-1, AP-2, Sp 1, NF-icB, and other transcriptional activators and/or repressors (factors), co-activators and co-repressors, histone acetylators and deacetylators, DNA methylases and demethylases, oncogenes or proto-oncogenes, or protein kinase C. These proteins act to regulate and thereby control expression of specific viral and/or other cellular genetic elements. According to the methods of the invention, control over their expression can lead to control over the infection. Other gene products, both viral and cellular in origin, whose expression can be regulated with inducing agents include proteases, polymerases, reverse transcriptases, cell-surface receptors, major histocompatibility antigens, growth factors, and combination of these products.

Additional genes whose expression or transcriptional regulation are altered in the presence of butyric acid include the oncogenes myc, ras, myb, abl and src. The activities of these gene products, as well as the activities of other oncogenes, are described in Slamon, J. D., et al. 1984 Science 224:256-62. Anti-proliferative activity also includes the ability to repress tumor angiogenesis through the blockade of angiogenesis factor activity, production or release, transcriptional regulation, or the ability to modulate transcription of genes under angiogenesis or growth factor or holinonal control. Either would be an effective therapy, particularly against both prostatic neoplasia and breast carcinomas. Further activities that effect transcription and/or cellular differentiation include increased intracellular cAMP levels, inhibition of histone acetylation, and inhibition of genomic methylation. Each of these activities is directly related to gene expression, and increased expression can sensitize infected cells to a specific anti-viral agent.

In some embodiments, inducing agents include arginine butyrate and/or other histone deacetylase inhibitors. Arginine butyrate induces EBV-TK activity in EBV-immortalized B-cells and patient-derived tumor cells. As latently-infected B-cells do not express TK, exposure of these cells to agents like arginine butyrate and/or other HDAC inhibitors results in a induction of lytic replication and TK expression. This expression of a viral gene can be used as a point for attack by anti-viral agents, allowing for treatment of latent infections.

In other embodiments, inducing agents include HDAC inhibitors that induce EBV-PK activity (also known BGLF4) in EBV infected tumors. Expression of EBV-PK/BGLF4 sensitizes a cell to an antiviral agent. In certain instances, HDAC inhibitors induce EBV-PK. In some instances, HDAC inhibitors induce EBV-TK and/or EBV-PK.

Preliminary in vitro studies according to the invention demonstrate that induction of EBV-TK activity in EBV-immortalized B-cells and patient-derived tumor cells using these drugs is possible, and that these previously resistant cells are rendered susceptible to ganciclovir therapy. Treatment of patients with viral-associated tumors such as EBV with inducing agents such as arginine butyrate, to induce the expression of EBV-TK/EBV-PK, and GCV, to eliminate EBV-TK/EBV-PK expressing tumor cells, is an effective, non-toxic therapy. This therapeutic regimen does not depend on the associated viral genome being the cause of the tumor. Without wishing to be bound by theory, it is believed that just the presence of the EBV genome in latent form would make the tumor susceptible to this combination protocol.

Butyrate-associated induction of genes has been characterized for various cell types, and the genes are consistently in the class of differentiation markers of a cell. For example, in colon cancer cell lines, morphologic changes observed in the presence of butyrate correlate with increased expression of alkaline phosphatase, plasminogen activator, and CEA, all markers of differentiation. Hepatoma cell lines increase expression of alpha fetoprotein. Breast cancer cell lines express milk-related glycoproteins, epithelial membrane antigens, and increased lipid deposition. Sodium butyrate can also induce expression of cellular proteins associated with converting basal keratinacytes into committed epithelial cells.

Alteration of expression of certain transcription factors may affect regulation of gene expression and regulation of the cell cycle. In the breast cancer cell line MCF-7, butyrate induces a block in cellular proliferation that is associated with decreased expression of estrogen and prolactin hormone receptor mRNA expression, thus blocking the potential growth stimulation by estrogen and prolactin. These effects are associated with increased expression of the EGF receptor. Butyrate also has been shown to induce down-regulation of c-myc and p53 mRNA and to up-regulate expression of the c-fos transcription factor. In mouse fibroblasts, butyrate will block the cell cycle in the $G_1$ phase. When these cells are stimulated to proliferate with serum, TPA, or insulin, the immediate-early response transcription factors c-myc and c-jun are unregulated. However, the late $G_1$ phase downstream gene marker cdc-2 mRNA is not expressed, and cells are prevented from entering S phase.

The particular combination of inducing agent with anti-viral agent that is most effective against a specific disorder can be determined by one of ordinary skill in the art from empirical testing and, preferably, from a knowledge of each agent's mechanism of action. Three such examples are as follows. First, many of the RNA viruses such as HIV and other retroviruses require a reverse transcriptase to transcribe their genome into DNA. A few of the agents that induce expression or activity of retroviruses and their encoded genes, such as, for example, reverse transcriptase, are known to those of ordinary skill in the art. Anti-viral agents such as nucleoside analogs can be administered to the patient. Those substrate analogs will be specifically recognized by the reverse transcriptase that, when incorporated into the infected-cell genome, prevent viral replication and may also result in cell death. Second, many viruses require an active protease to assemble virus capsids to be packaged with viral genome. Protease inhibitors or proteases that alter cleavage patterns so that packaging cannot occur can be specifically targeted with an anti-viral agent that comprises an amino acid analog or toxic conjugate. Third, arginine butyrate and isobutyramide enhance expression of viral thymidine kinase and other viral protein kinases in EBV-infected lymphocytes. Ganciclovir or famcyclovir, in the presence of the viral thymidine kinase or other viral kinases, destroys the infected cell. Treatment of infected cells with both agents, according to the invention, will selectively destroy EBV virus-infected cells. In another aspect, of infected cells with both agents, according to the invention, will selectively disable or disrupt the viral activity within the cells in vivo.

In some embodiments, an inducing agent induces viral gene expression by more than 4 fold after 24 h of treatment. In certain embodiments, an HDAC inhibitor induces TK or EBV-PK expression by more than 4 fold after 24 h of treatment. In some embodiments, an HDAC inhibitor induces viral gene expression after about 48 h, about 36 h, about 24 h, about 18 h, about 12 h, about 8 h, about 6 h, about 4 h, about 3 h, about 2 h, about 1 h, or about 30 minutes. In certain embodiments, an HDAC inhibitor induces viral gene expression in less than 48 h, less than 36 h, less than 24 h, less than 18 h, less than 12 h, less than 8 h, less than 6 h, less than 4 h, less than 3 h, less than 2 h, less than 1 h, or less than 30 minutes. In some embodiments, an HDAC inhibitor induces viral gene expression in more than 48 h, more than 36 h, more than 24 h, more than 18 h, more than 12 h, more than 8 h, more than 6 h, more than 4 h, more than 3 h, more than 2 h, more than 1 h, or more than 30 minutes. In certain embodiments, an HDAC inhibitor induces viral gene expression after more than 30 minutes and less than 24 h.

In certain embodiments, an inducing agent is capable of inducing gene expression at a concentration of less than 500 nM. In some embodiments, the inducing agent is an HDAC inhibitor. In certain embodiments, the inducing agent is capable of inducing TK or EBV-PK expression. In certain embodiments, an inducing agent is capable of inducing gene expression at a concentration of about 100 µM, about 90 µM, about 80 µM, about 75 µM, about 70 µM, about 60 µM, about 50 µM, about 40 µM, about 30 µM, about 25 µM, about 20 µM, about 10 µM, about 5 µM, about 2 µM, about 1 µM, about 900 nM, about 800 nM, about 700 nM, about 600 nM, about 500 nM, about 400 nM, about 300 nM, about 200 nM, about 100 nM, about 75 nM, about 50 nM, about 20 nM, or about 10 nM. In some embodiments, an inducing agent is capable of inducing gene expression at a concentration of less than 100 µM, less than 90 µM, less than 80 µM, less than 75 µM, less than 70 µM, less than 60 µM, less than 50 µM, less than 40 µM, less than 30 µM, less than 25 µM, less than 20 µM, less than 10 µM, less than 5 µM, less than 2 µM, less than 1 µM, less than 900 nM, less than 800 nM, less than 700 nM, less than 600 nM, less than 500 nM, less than 400 nM, less than 300 nM, less than 200 nM, less than 100 nM, less than 75 nM, less than 50 nM, less than 20 nM, or less than 10 nM. In certain embodiments, an inducing agent is capable of inducing gene expression at a concentration of more than 100 µM, more than 90 µM, more than 80 µM, more than 75 µM, more than 70 µM, more than 60 µM, more than 50 µM, more than 40 µM, more than 30 µM, more than 25 µM, more than 20 µM, more than 10 µM, more than 5 µM, more than 2 µM, more than 1 µM, more than 900 nM, more than 800 nM, more than 700 nM, more than 600 nM, more than 500 nM, more than 400 nM, more than 300 nM, more than 200 nM, more than 100 nM, more than 75 nM, more than 50 nM, more than 20 nM, or more than 10 nM. In some embodiments, an inducing agent is capable of inducing gene expression at a concentration more than 50 nM and less than 100 nM. In certain embodiments, an inducing agent is capable of inducing gene expression at a concentration of more than 200 nM and less than 500 nM. In some embodiments, an inducing agent is capable of inducing gene expression at more than 100 nM and less than 200 nM In some embodiments, an HDAC inhibitor induces viral gene expression after more than 1 h and less than 6 h. In certain embodiments, an HDAC inhibitor induces viral gene expression about 2 fold, about 3 fold, about 4 fold, about 5 fold, about 6 fold, about 7 fold, about 8 fold, about 9 fold, about 10 fold, about 12 fold, about 15 fold, about 20 fold, about 25 fold, about 30 fold, about 35 fold, about 40 fold, about 45 fold, or about 50 fold. In some embodiments, an HDAC inhibitor induces viral gene expression less than 2 fold, less than 3 fold, less than 4 fold, less than 5 fold, less than 6 fold, less than 7 fold, less than 8 fold, less than 9 fold, less than 10 fold, less than 12 fold, less than 15 fold, less than 20 fold, less than 25 fold, less than 30 fold, less than 35 fold, less than 40 fold, less than 45 fold, or less than 50 fold. In certain embodiments, an HDAC inhibitor induces viral gene expression more than 2 fold, more than 3 fold, more than 4 fold, more than 5 fold, more than 6 fold, more than 7 fold, more than 8 fold, more than 9 fold, more than 10 fold, more than 12 fold, more than 15 fold, more than 20 fold, more than 25 fold, more than 30 fold, more than 35 fold, more than 40 fold, more than 45 fold, or more than 50 fold. In some embodiments, an HDAC inhibitor induces viral gene expression more than 2 fold and less than 50 fold. In certain embodiments, an HDAC inhibitor induces viral gene expression more than 5 fold and less than 40 fold.

Antiviral Agents

Anti-viral agents that can be used in the compositions and methods of the provided invention can include, for example, substrates and substrate analogs, inhibitors and other agents that severely impair, debilitate or otherwise destroy virus-infected cells. Substrate analogs include amino acid and nucleoside analogs. Substrates can be conjugated with toxins or other viricidal substances. Inhibitors include integrase inhibitors, protease inhibitors, polymerase inhibitors and transcriptase inhibitors such as reverse transcriptase inhibitors.

Antiviral agents that can be used in the compositions and methods of the provided invention can include, for example, ganciclovir, valganciclovir, oseltamivir (Tamiflu™), zanamivir (Relenza™), abacavir, aciclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, fusion inhibitors (e.g., enfuvirtide), ibacitabine, imunovir, idoxuridine, imiquimod, indinavir, inosine, integrase inhibitor, interferon type III, interferon type II, interferon type I, interferon, lamivudine, lopinavir, loviride, maraviroc, moroxydine, nelfinavir, nevirapine, nexavir, nucleoside analogues, peginterferon alfa-2a, penciclovir, peramivir, pleconaril, podophyllotoxin, protease inhibitor, raltegravir, reverse transcriptase inhibitor, ribavirin, rimantadine, ritonavir, pyrimidine antiviral, saquinavir, stavudine, synergistic enhancer (antiretroviral), tenofovir, tenofovir disoproxil, tipranavir, trifluridine, trizivir, tromantadine, truvada, valaciclovir (Valtrex™), vicriviroc, vidarabine, viramidine, zalcitabine, and zidovudine.

In a specific embodiment, the antiviral agent is acyclovir, ganciclovir, or valganciclovir.

In some embodiments, the antiviral agent is a nucleoside. Examples of nucleoside analogs include acyclovir (ACV), ganciclovir (GCV), valganciclovir, famciclovir, foscarnet, ribavirin, zalcitabine (ddC), zidovudine (AZT), stavudine (D4T), larnivudine (3TC), didanosine (ddI), cytarabine, dideoxyadenosine, edoxudine, floxuridine, idozuridine, inosine pranobex, 2'-deoxy-5-(methylamino)uridine, trifluridine and vidarabine. Examples of a few protease inhibitors that show particular promise in human therapy include saquinivir, ritonavir and indinavir. Other anti-viral agents include interferons (e.g. α-, β-, γ-interferon), cytokines such as tumor necrosis factor (TNF) or interleukins, cell receptors and growth factor antagonists, which can be purified or recombinantly produced.

In some embodiments, the antiviral agent is administered at a dose of less than 3000 mg/day. In some embodiments, the antiviral agent is administered at a dose of about 10 mg/day, about 20 mg/day, about 50 mg/day, about 100 mg/day, about 150 mg/day, about 200 mg/day, about 250 mg/day, about 300 mg/day, about 350 mg/day, about 400 mg/day, about 450 mg/day, about 500 mg/day, about 600 mg/day, about 700 mg/day, about 800 mg/day, about 900 mg/day, about 1000 mg/day, about 1200 mg/day, about 1250 mg/day, about 1400 mg/day, about 1500 mg/day, about 1600 mg/day, about 1750 mg/day, about 1800 mg/day, about 1900 mg/day, about 2000 mg/day, about 2250 mg/day, about 2500 mg/day, about 2750 mg/day, about 3000 mg/day, about 3250 mg/day, about 3500 mg/day, about 3750 mg/day, about 4000 mg/day, about 4250 mg/day, about 4500 mg/day, about 4750 mg/day, or about 5000 mg/day. In certain embodiments, the antiviral agent is administered at a dose of less than 10 mg/day, less than 20 mg/day, less than 50 mg/day, less than 100 mg/day, less than 150 mg/day, less than 200 mg/day, less than 250 mg/day, less than 300 mg/day, less than 350 mg/day, less than 400 mg/day, less than 450 mg/day, less than 500 mg/day, less than 600 mg/day, less than 700 mg/day, less than 800 mg/day, less than 900 mg/day, less than 1000 mg/day, less than 1200 mg/day, less than 1250 mg/day, less than 1400 mg/day, less than 1500 mg/day, less than 1600 mg/day, less than 1750 mg/day, less than 1800 mg/day, less than 1900 mg/day, less than 2000 mg/day, less than 2250 mg/day, less than 2500 mg/day, less than 2750 mg/day, less than 3000 mg/day, less than 3250 mg/day, less than 3500 mg/day, less than 3750 mg/day, less than 4000 mg/day, less than 4250 mg/day, less than 4500 mg/day, less than 4750 mg/day, or less than 5000 mg/day. In some embodiments, the antiviral agent is administered at a dose of more than 10 mg/day, more than 20 mg/day, more than 50 mg/day, more than 100 mg/day, more than 150 mg/day, more than 200 mg/day, more than 250 mg/day, more than 300 mg/day, more than 350 mg/day, more than 400 mg/day, more than 450 mg/day, more than 500 mg/day, more than 600 mg/day, more than 700 mg/day, more than 800 mg/day, more than 900 mg/day, more than 1000 mg/day, more than 1200 mg/day, more than 1250 mg/day, more than 1400 mg/day, more than 1500 mg/day, more than 1600 mg/day, more than 1750 mg/day, more than 1800 mg/day, more than 1900 mg/day, more than 2000 mg/day, more than 2250 mg/day, more than 2500 mg/day, more than 2750 mg/day, more than 3000 mg/day, more than 3250 mg/day, more than 3500 mg/day, more than 3750 mg/day, more than 4000 mg/day, more than 4250 mg/day, more than 4500 mg/day, more than 4750 mg/day, or more than 5000 mg/day. In certain embodiments, the antiviral agent is administered at a dose of more than 10 mg/day and less than 5000 mg/day. In some embodiments, the antiviral agent is administered at a dose of more than 200 mg/day and less than 1000 mg/day. In certain embodiments, the antiviral agent is administered once a day (q.d.), twice a day (b.id.), or thrice a day (t.i.d.). In some embodiments, the antiviral agent is administered daily, once a week, twice a week, three times a week, four times a week, or five times a week.

In certain embodiments, the antiviral agent is ganciclovir. In some embodiments, ganciclovir is administered at a total daily dose of 3000 mg/day. In certain embodiments, ganciclovir is administered at a dose of 1000 mg three times a day. In some embodiments, ganciclovir is administered at a dose of about 100 mg/day, about 250 mg/day, about 500 mg/day, about 750 mg/day, about 1000 mg/day, about 1500 mg/day, about 2000 mg/day, about 2500 mg/day, about 3000 mg/day, about 3500 mg/day, or about 4000 mg/day. In certain embodiments, ganciclovir is administered at a dose of less than 100 mg/day, less than 250 mg/day, less than 500 mg/day, less than 750 mg/day, less than 1000 mg/day, less than 1500 mg/day, less than 2000 mg/day, less than 2500 mg/day, less than 3000 mg/day, less than 3500 mg/day, or less than 4000 mg/day. In some embodiments, ganciclovir is administered at a dose of more than 100 mg/day, more than 250 mg/day, more than 500 mg/day, more than 750 mg/day, more than 1000 mg/day, more than 1500 mg/day, more than 2000 mg/day, more than 2500 mg/day, more than 3000 mg/day, more than 3500 mg/day, or more than 4000 mg/day. In certain embodiments, ganciclovir is administered at a dose of more than 500 mg/day and less 4000 mg/day. In some embodiments, ganciclovir is administered at a dose of more than 1000 mg/day and less than 3000 mg/day. In some embodiments, ganciclovir is administered once a day, twice a day, or three times a day. In certain embodiments, ganciclovir is administered once a week, twice a week, three times a week, four times a week, five times a week, or daily.

In some embodiments, the antiviral agent is valganciclovir. In certain embodiments, valganciclovir is administered at a total daily dose of 900 mg/day. In some embodiments, valganciclovir is administered at a dose of 900 mg once a day. In certain embodiments, valganciclovir is administered at a total daily dose of 1800 mg/day. In some embodiments, valganciclovir is administered at a dose of 900 mg twice a day.

In some embodiments, valganciclovir is administered at a dose of about 100 mg/day, about 200 mg/day, about 300 mg/day, about 400 mg/day, about 500 mg/day, about 600 mg/day, about 700 mg/day, about 800 mg/day, about 900 mg/day, about 1000 mg/day, about 1100 mg/day, about 1200 mg/day, about 1300 mg/day, about 1400 mg/day, about 1500 mg/day, about 1600 mg/day, about 1700 mg/day, about 1800 mg/day, about 1900 mg/day, or about 2000 mg/day. In certain embodiments, valganciclovir is administered at a dose of less than 100 mg/day, less than 200 mg/day, less than 300 mg/day, less than 400 mg/day, less than 500 mg/day, less than 600 mg/day, less than 700 mg/day, less than 800 mg/day, less than 900 mg/day, less than 1000 mg/day, less than 1100 mg/day, less than 1200 mg/day, less than 1300 mg/day, less than 1400 mg/day, less than 1500 mg/day, less than 1600 mg/day, less than 1700 mg/day, less than 1800 mg/day, less than 1900 mg/day, or less than 2000 mg/day. In some embodiments, valganciclovir is administered at a dose of more than 100 mg/day, more than 200 mg/day, more than 300 mg/day, more than 400 mg/day, more than 500 mg/day, more than 600 mg/day, more than 700 mg/day, more than 800 mg/day, more than 900 mg/day, more than 1000 mg/day, more than 1100 mg/day, more than 1200 mg/day, more than 1300 mg/day, more than 1400 mg/day, more than 1500 mg/day, more than 1600 mg/day, more than 1700 mg/day, more than 1800 mg/day, more than 1900 mg/day, or more than 2000 mg/day. In certain embodiments, valganciclovir is administered at a dose of more than 100 mg/day and less 2000 mg/day. In some embodiments, valganciclovir is administered at a dose of more than 500 mg/day and less than 1500 mg/day. In some embodiments, valganciclovir is administered once a day, twice a day, or three times a day. In certain embodiments, valganciclovir is administered once a week, twice a week, three time a week, four times a week, five times a week, or daily.

In a specific embodiment, the antiviral agent is not a heat shock protein inhibitor, an immunosuppressant, an antibiotic, a glucocorticoid, a non-steroidal anti-inflammatory drug, a Cox-2-specific inhibitor or a TNF-α binding protein. In a related embodiment, the antiviral agent is not a Hsp90 inhibitor, tacrolimus, cyclosporin, rapamycin (sirolimus), methotrexate, cyclophosphamide, azathioprine, mercaptopurine, mycophenolate, FTY720, levofloxacin, amoxycillin, prednisone, cortisone acetate, prednisolone, methylprednisolone, dexamethasone, betamethasone, triamcinolone, beclometasone, fludrocortisone acetate, deoxycorticosterone acetate, aldosterone, salicylates, arylalkanoic acids, a 2-arylpropionic acid, a N-arylanthranilic acid, an oxicam, a coxib, a sulphonanilide, valdecoxib, celecoxib, rofecoxib, leflunomide, gold thioglucose, gold thiomalate, aurofin, sulfasalazine, hydroxychloroquinine, minocycline, infliximab, etanercept, adalimumab, abatacept, anakinra, interferon-β, interferon-γ, interleukin-2, an allergy vaccine, an antihistamine, an antileukotriene, a beta-agonist, theophylline, or an anticholinergic.

Additional Agents

The methods of the provided invention can comprise administering to a subject a viral inducing agent, and antiviral agent, and one or more additional active agents. The additional agent can be selected based on the type of viral, virally-induced, or inflammatory condition the subject has or is suspected of having. The additional agent can comprise, for example, another antiviral agent, another viral inducing agent, a vaccine, or an anticancer agent. For example, a subject with multiple sclerosis can be administered a viral inducing agent, an antiviral agent, and a vaccine, for example, a vaccine comprising myelin basic protein. In another example, a subject with diabetes can be administered a viral inducing agent, an antiviral agent, and a vaccine, for example, a vaccine comprising an antigen.

In some embodiments, an additional agent is a anticancer agent. In certain embodiments, the anticancer agent is a chemotherapeutic anticancer agent. Examples of chemotherapeutic anticancer agents include, but are not limited to, nitrogen mustards; alkyl sulfonates; ethylene imines; nitrosoureas; epoxides; other alkylating agents; folic acid analogues; purine analogs; pyrimidine analogs; vinca alkaloids; podophyllotoxin derivatives; colchicine derivatives; taxanes; other plant alkaloids and natural products; actinomycines; antracyclines; other cytotoxic antibiotics; platinum compounds; methylhydrazines; sensitizers; protein kinase inhibitors; other antineoplastic agents; estrogens; progestogens; gonadotropin releasing hormone analogs; anti-estrogens; anti-androgens; enzyme inhibitors; other hormone antagonists; immunostimulants; immunosuppressants; calcineurin inhibitors; and radiopharmaceuticals. In some embodiments, the anticancer agent is a toxin, e.g. diphtheria toxin.

In certain embodiments, an additional agent is a non-steroidal anti-inflammatory agent (NSAID). NSAID include, for example, Aspirin (Anacin™, Ascriptin™, Bayer™, Bufferin™, Ecotrin™, Excedrin™), Choline and magnesium salicylates (CMT™, Tricosal™, Trilisate™), choline salicylate (Arthropan™), celecoxib (Celebrex™), diclofenac potassium (Cataflam™), diclofenac sodium (Voltaren™, Voltaren XR™), diclofenac sodium with misoprostol (Arthrotec™), diflunisal (Dolobid™), etodolac (Lodine™, Lodine XL™), fenoprofen calcium (Nalfon™), flurbiprofen (Ansaid™), ibuprofen (Advil™, Motrin™, Motrin IB™ Nuprin™), indomethacin (Indocin™, Indocin SR™), ketoprofen (Actron™, Orudis™, Orudis KT™, Oruvail™), magnesium salicylate (Arthritab™, Bayer Select™, Doan's Pills™, Magan™, Mobidin™ Mobogesic™), meclofenamate sodium (Meclomen™), mefenamic acid (Ponstel™), meloxicam (Mobic™), nabumetone (Relafen™), naproxen (Naprosyn™, Naprelan™), naproxen sodium (Aleve™, Anaprox™), oxaprozin (Daypro™), piroxicam (Feldene™), rofecoxib (Vioxx™), salsalate (Amigesic™, Anaflex 750™, Disalcid™, Marthritic™, Mono-Gesic™, Salflex™, Salsitab™), sodium salicylate (various generics), sulindac (Clinoril™), tolmetin sodium (Tolectin™), valdecoxib (Bextra™).

In some embodiments, an additional agent is a lipid lowering agent. In certain embodiments, the lipid lowering agent is a statin. Examples of statins include, but are not limited to, Advicor® (niacin extended-release/lovastatin), Altoprev® (lovastatin extended-release), Caduet® (amlodipine and atorvastatin), Crestor® (rosuvastatin), Lescol® (fluvastatin), Lescol XL (fluvastatin extended-release), Lipitor® (atorvastatin), Mevacor® (lovastatin), Pravachol® (pravastatin), Simcor® (niacin extended-release/simvastatin), Vytorin® (ezetimibe/simvastatin), and Zocor® (simvastatin). A lipid lowering agent can be administered to a subject that has or is suspected of having atherosclerosis. For example, a subject with cytomegalovirus induced atherosclerosis can be administered an additional agent that can comprise atorvastatin, rosuvastatin, lovastatin, simvastatin, or pravastatin.

In certain embodiments, an additional agent is an immunosuppressive drug. Immunosuppressive drug, for example, include glucocorticoids, antibodies, cytostatic agents, and drugs that act on immunophilins. Glucocorticoids can include, for example, prednisolone, prednisone, or methyl-prednisolone. A cytostatic agent can include, for example, an agent that interferes with nucleic acid synthesis, for example, folic acid, pyrimidine analogs, and purine analogs. A folic acid analog that can be used as an immunosuppressive drug is methotrexate, which can bind dihydrofolate reductase and prevent the synthesis of tetrahydrofolate. Another cytostatic agent is azathioprine, which can be cleaved nonezymatically to form mercaptopurine, which can act as a purine analogue. A cytostatic agent can include, for example, an alkylating agent, including, for example, cyclophosphamide, and a nitrosourea. A cytostatic agent can be a platinum compound. Other cytostatic agents include, for example, cytotoxic antibiotics, including dactinomycin, anthracylines, mitomycin C, bleomycin, and mithramycin. Examples of antibodies that can be immunosuppressive agents include, for example, heterologous polyclonal antibodies, for example, from rabbit or horse. Other antibodies include monoclonal antibodies directed to specific antigens e.g., T-cell receptor directed antibodies (e.g., OKT3, muromonab, which targets CD3), and IL-2 receptor directed antibodies (e.g., targeting CD25). Drugs that can act on immunophilins include, for example, cyclosporin, tacrolimus (Prograf), Sirolimus (rapamycin, Rapamune). Other drugs that can act as immunosuppressive drugs include, for example, mycophenolate (mycophenolic acid), interferons, opioids, TNF binding proteins, Fingolimod, myriocin, and ciclosporin.

The additional agent can be, for example, FK506, a monoclonal antibody, an anti-T cell monoclonal antibody, an anti-B cell monoclonal antibody, or a TNF inhibitor. The monoclonal antibody can be an anti-B cell antibody. The anti-B cell antibody can be anti-CD20. The TNF inhibitor can be infliximab (Remicade™), etanercept (Enbrel™), adalimumab (Humira™), or an anti-IL-6 antibody.

A subject with an autoimmune condition can be administered a viral inducing agent, an antiviral agent, and an additional agent, where the additional agent comprises cyclosporine, azathiorprine, methotrexate, cyclophosphamide, FK506, tacrolimus, a monoclonal antibody, an anti-T cell monoclonal antibody, an anti-B cell monoclonal antibody, an IL-2 receptor antibody, or a TNF inhibitor.

The additional agent can be glatiramer (Copaxone™), Natalizumab (Tysabri™), mitoxantrone (Novantrone™), cladribine, or Campath antibody. For example, a subject with multiple sclerosis can be administered an additional agent that can comprise glatiramer, mitoxantrone, natalizumab, cladribine, or Campath antibody.

Types of Viruses and Virally-Induced Conditions

The methods and compositions provided herein can be used to treat and/or prevent viral infections. The virus causing the infection can be a member of the herpes virus family, a human immunodeficiency virus, parvovirus, or coxsackie virus. A member of the herpes virus family can be herpes simplex virus, herpes genitalis virus, varicella zoster virus, Epstein-Barr virus, human herpes virus 6, human herpes virus 8, or cytomegalovirus. The subject can have coronary artery condition associated with a cytomegalovirus or herpes simplex virus infection. The subject can have autoimmune condition associated with Epstein-Barr virus infection. The subject can have a lymphoma or other cancer associated with Epstein-Barr virus infection.

In some embodiments, the viral or virally-induced condition is caused by a retrovirus, such as HIV, HTLV1 and 2. In certain embodiments, the viral or virally-induced condition is caused by a DNA virus, such as a herpesvirus. In some embodiments, the herpesvirus is an Epstein-Barr virus, cytomegalovirus, Herpes type 1 (oral herpes), herpes type 2, Kaposi's sarcoma virus (human herpes virus 8), BK viruses, or hepatitis virus. In certain embodiments, the virally-induced or virus-associated disease is a cancer. In some embodiments, the virally-induced or virus-associated cancer is a lymphoma, chronic lyphocytic leukemia, nasopharyngeal carcinoma, gastric cancer, or Kaposi's sarcoma. In other embodiments, the virally-induced or virus-associated disease is an autoimmune disease. In certain embodiments, the autoimmune disease is rheumatoid arthritis, systemic lupus erythematosus, or multiple sclerosis.

The methods and compositions described herein can be used to treat and/or prevent infections caused by any virus, including, for example, Abelson leukemia virus, Abelson murine leukemia virus, Abelson's virus, Acute laryngotracheobronchitis virus, Adelaide River virus, Adeno associated virus group, Adenovirus, African horse sickness virus, African swine fever virus, AIDS virus, Aleutian mink condition parvovirus, Alpharetrovirus, Alphavirus, ALV related virus, Amapari virus, Aphthovirus, Aquareovirus, Arbovirus, Arbovirus C, arbovirus group A, arbovirus group B, Arenavirus group, Argentine hemorrhagic fever virus, Argentine hemorrhagic fever virus, Arterivirus, Astrovirus, Ateline herpesvirus group, Aujezky's condition virus, Aura virus, Ausduk condition virus, Australian bat lyssavirus, Aviadenovirus, avian erythroblastosis virus, avian infectious bronchitis virus, avian leukemia virus, avian leukosis virus, avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus, B19 virus, Babanki virus, baboon herpesvirus, baculovirus, Barmah Forest virus, Bebaru virus, Berrimah virus, Betaretrovirus, Birnavirus, Bittner virus, BK virus, Black Creek Canal virus, bluetongue virus, Bolivian hemorrhagic fever virus, Boma condition virus, border condition of sheep virus, borna virus, bovine alphaherpesvirus 1, bovine alphaherpesvirus 2, bovine coronavirus, bovine ephemeral fever virus, bovine immunodeficiency virus, bovine leukemia virus, bovine leukosis virus, bovine mammillitis virus, bovine papillomavirus, bovine papular stomatitis virus, bovine parvovirus, bovine syncytial virus, bovine type C oncovirus, bovine viral diarrhea virus, Buggy Creek virus, bullet shaped virus group, Bunyamwera virus supergroup, Bunyavirus, Burkitt's lymphoma virus, Bwamba Fever, CA virus, Calicivirus, California encephalitis virus, camelpox virus, canarypox virus, canid herpesvirus, canine coronavirus, canine distemper virus, canine herpesvirus, canine minute virus, canine parvovirus, Cano Delgadito virus, caprine arthritis virus, caprine encephalitis virus, Caprine Herpes Virus, Capripox virus, Cardiovirus, caviid herpesvirus 1, Cercopithecid herpesvirus 1, cercopithecine herpesvirus 1, Cercopithecine herpesvirus 2, Chandipura virus, Changuinola virus, channel catfish virus, Charleville virus, chickenpox virus, Chikungunya virus, chimpanzee herpesvirus, chub reovirus, chum salmon virus, Cocal virus, Coho salmon reovirus, coital exanthema virus, Colorado tick fever virus, Coltivirus, Columbia SK virus, common cold virus, contagious ecthyma virus, contagious pustular dermatitis virus, Coronavirus, Corriparta virus, coryza virus, cowpox virus, coxsackie virus, CPV (cytoplasmic polyhedrosis virus), cricket paralysis virus, Crimean-Congo hemorrhagic fever virus, croup associated virus, Cryptovirus, Cypovirus, Cytomegalovirus, cytomegalovirus group, cytoplasmic polyhedrosis virus, deer papillomavirus, deltaretrovirus, dengue virus, Densovirus, Dependovirus, Dhori virus, diploma virus, *Drosophila* C virus, duck hepatitis B virus, duck hepatitis virus 1, duck hepatitis virus 2, duovirus, Duvenhage virus, Deformed wing virus DWV, eastern equine encephalitis virus, eastern equine encephalomyelitis virus, EB virus, Ebola virus, Ebola-like virus, echo virus, echovirus, echovirus 10, echovirus 28, echovirus 9, ectromelia virus, EEE virus, EIA virus, EIA virus, encephalitis virus, encephalomyocarditis group virus, encephalomyocarditis virus, Enterovirus, enzyme elevating virus, enzyme elevating virus (LDH), epidemic hemorrhagic fever virus, epizootic hemorrhagic condition virus, Epstein-Barr virus, equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillomavirus, European swine fever virus, Everglades virus, Eyach virus, felid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus, feline syncytial virus, Filovirus, Flanders virus, Flavivirus, foot and mouth condition virus, Fort Morgan virus, Four Corners hantavirus, fowl adenovirus 1, fowlpox virus, Friend virus, Gammaretrovirus, GB hepatitis virus, GB virus, German measles virus, Getah virus, gibbon ape leukemia virus, glandular fever virus, goatpox virus, golden shinner virus, Gonometa virus, goose parvovirus, granulosis virus, Gross' virus, ground squirrel hepatitis B virus, group A arbovirus, Guanarito virus, guinea pig cytomegalovirus, guinea pig type C virus, Hantaan virus, Hantavirus, hard clam reovirus, hare fibroma virus, HCMV (human cytomegalovirus), hemadsorption virus 2, hemagglutinating virus of Japan, hemorrhagic fever virus, hendra virus, Henipaviruses, Hepadnavirus, hepatitis A virus, hepatitis B virus group, hepatitis C virus, hepatitis D virus, hepatitis delta virus, hepatitis E virus, hepatitis F virus, hepatitis G virus, hepatitis nonA nonB virus, hepatitis virus, hepatitis virus (nonhuman), hepatoencephalomyelitis reovirus 3, Hepatovirus, heron hepatitis B virus, herpes B virus, herpes simplex virus, herpes simplex virus 1, herpes simplex virus 2, herpesvirus, herpesvirus 7, Herpesvirus ateles, Herpesvirus hominis, Herpesvirus infection, Herpesvirus saimiri, Herpesvirus suis, Herpesvirus varicellae, Highlands J virus, Hirame rhabdovirus, hog cholera virus, human adenovirus 2, human alphaherpesvirus 1, human alphaherpesvirus 2, human alphaherpesvirus 3, human B lymphotropic virus, human betaherpesvirus 5, human coronavirus, human cytomegalovirus group, human foamy virus, human gammaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immunodeficiency virus, human immunodeficiency virus 1, human immunodeficiency virus 2, human papillomavirus, human T cell leukemia virus, human T cell leukemia virus I, human T cell leukemia virus II, human T cell leukemia virus III, human T cell lymphoma virus I, human T cell lymphoma virus II, human T cell lymphotropic virus type 1, human T cell lymphotropic virus type 2, human T lymphotropic virus I, human T lymphotropic virus II, human T lymphotropic virus III, Ichnovirus, infantile gastroenteritis virus, infectious bovine rhinotracheitis virus, infectious haematopoietic necrosis virus, infectious pancreatic necrosis virus, influenza virus A, influenza virus B, influenza virus C, influenza virus D, influenza virus pr8, insect iridescent virus, insect virus, iridovirus, Japanese B virus, Japanese encephalitis virus, JC virus, Junin virus, Kaposi's sarcoma-associated herpesvirus, Kemerovo virus, Kilham's rat virus, Klamath virus, Kolongo virus, Korean hemorrhagic fever virus, kumba virus, Kysanur forest condition virus, Kyzylagach virus, La Crosse virus, lactic dehydrogenase elevating virus, lactic dehydrogenase virus, Lagos bat virus, Langur virus, lapine parvovirus, Lassa fever virus, Lassa virus, latent rat virus, LCM virus, Leaky virus, Lentivirus, Leporipoxvirus, leukemia virus, leukovirus, lumpy skin condition virus, lymphadenopathy associated virus, Lymphocryptovirus, lymphocytic choriomeningitis virus, lymphoproliferative virus group, Machupo virus, mad itch virus, mammalian type B oncovirus group, mammalian type B retroviruses, mammalian type C retrovirus group, mammalian type D retroviruses, mammary tumor virus, Mapuera virus, Marburg virus, Marburg-like virus, Mason Pfizer monkey virus, Mastadenovirus, Mayaro virus, ME virus, measles virus, Menangle virus, Mengo virus, Mengovirus, Middelburg virus, milkers nodule virus, mink enteritis virus, minute virus of mice, MLV related virus, MM virus, Mokola virus, Molluscipoxvirus, Molluscum contagiosum virus, monkey B virus, monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyomavirus, mouse sarcoma virus, mousepox virus, Mozambique virus, Mucambo virus, mucosal condition virus, mumps virus, murid betaherpesvirus 1, murid cytomegalovirus 2, murine cytomegalovirus group, murine encephalomyelitis virus, murine hepatitis virus, murine leukemia virus, murine nodule inducing virus, murine polyomavirus, murine sarcoma virus, Muromegalovirus, Murray Valley encephalitis virus, myxoma virus, Myxovirus, Myxovirus multiforme, Myxovirus parotitidis, Nairobi sheep condition virus, Nairovirus, Nanirnavirus, Nariva virus, Ndumo virus, Neethling virus, Nelson Bay virus, neurotropic virus, New World Arenavirus, newborn pneumonitis virus, Newcastle condition virus, Nipah virus, noncytopathogenic virus, Norwalk virus, nuclear polyhedrosis virus (NPV), nipple neck virus, O'nyong'nyong virus, Ockelbo virus, oncogenic virus, oncogenic viruslike particle, oncornavirus, Orbivirus, Orf virus, Oropouche virus, Orthohepadnavirus, Orthomyxovirus, Orthopoxvirus, Orthoreovirus, Orungo, ovine papillomavirus, ovine catarrhal fever virus, owl monkey herpesvirus, Palyam virus, Papillomavirus, Papillomavirus sylvilagi, Papovavirus, parainfluenza virus, parainfluenza virus type 1, parainfluenza virus type 2, parainfluenza virus type 3, parainfluenza virus type 4, Paramyxovirus, Parapoxvirus, paravaccinia virus, Parvovirus, Parvovirus B19, parvovirus group, Pestivirus, Phlebovirus, phocine distemper virus, Picodnavirus, Picornavirus, pig cytomegalovirus—pigeonpox virus, Piry virus, Pixuna virus, pneumonia virus of mice, Pneumovirus, poliomyelitis virus, poliovirus, Polydnavirus, polyhedral virus, polyoma virus, Polyomavirus, Polyomavirus bovis, Polyomavirus cercopitheci, Polyomavirus hominis 2, Polyomavirus maccacae 1, Polyomavirus muris 1, Polyomavirus muris 2, Polyomavirus papionis 1, Polyomavirus papionis 2, Polyomavirus sylvilagi, Pongine herpesvirus 1, porcine epidemic diarrhea virus, porcine hemagglutinating encephalomyelitis virus, porcine parvovirus, porcine transmissible gastroenteritis virus, porcine type C virus, pox virus, poxvirus, poxvirus variolae, Prospect Hill virus, Provirus, pseudocowpox virus, pseudorabies virus, psittacinepox virus, quailpox virus, rabbit fibroma virus, rabbit kidney vaculolating virus, rabbit papillomavirus, rabies virus, raccoon parvovirus, raccoonpox virus, Ranikhet virus, rat cytomegalovirus, rat parvovirus, rat virus, Rauscher's virus, recombinant vaccinia virus, recombinant virus, reovirus, reovirus 1, reovirus 2, reovirus 3, reptilian type C virus, respiratory infection virus, respiratory syncytial virus, respiratory virus, reticuloendotheliosis virus, Rhabdovirus, Rhabdovirus carpia, Rhadinovirus, Rhinovirus, Rhizidiovirus, Rift Valley fever virus, Riley's virus, rinderpest virus, RNA tumor virus, Ross River virus, Rotavirus, rougeole virus, Rous sarcoma virus, rubella virus, rubeola virus, Rubivirus, Russian autumn encephalitis virus, SA 11 simian virus, SA2 virus, Sabia virus, Sagiyama virus, Saimirine herpesvirus 1, salivary gland virus, sandfly fever virus group, Sandjimba virus, SARS virus, SDAV (sialodacryoadenitis virus), sealpox virus, Semliki Forest Virus, Seoul virus, sheeppox virus, Shope fibroma virus, Shope papilloma virus, simian foamy virus, simian hepatitis A virus, simian human immunodeficiency virus, simian immunodeficiency virus, simian parainfluenza virus, simian T cell lymphotrophic virus, simian virus, simian virus 40, Simplexvirus, Sin Nombre virus, Sindbis virus, smallpox virus, South American hemorrhagic fever viruses, sparrowpox virus, Spumavirus, squirrel fibroma virus, squirrel monkey retrovirus, SSV 1 virus group, STLV (simian T lymphotropic virus) type I, STLV (simian T lymphotropic virus) type II, STLV (simian T lymphotropic virus) type III, stomatitis papulosa virus, submaxillary virus, suid alphaherpesvirus 1, suid herpesvirus 2, Suipoxvirus, swamp fever virus, swinepox virus, Swiss mouse leukemia virus, TAC virus, Tacaribe complex virus, Tacaribe virus, Tanapox virus, Taterapox virus, Tench reovirus, Theiler's encephalomyelitis virus, Theiler's virus, Thogoto virus, Thottapalayam virus, Tick borne encephalitis virus, Tioman virus, Togavirus, Torovirus, tumor virus, Tupaia virus, turkey rhinotracheitis virus, turkeypox virus, type C retroviruses, type D oncovirus, type D retrovirus group, ulcerative condition rhabdovirus, Una virus, Uukuniemi virus group, vaccinia virus, vacuolating virus, varicella zoster virus, Varicellovirus, Varicola virus, variola major virus, variola virus, Vasin Gishu condition virus, VEE virus, Venezuelan equine encephalitis virus, Venezuelan equine encephalomyelitis virus, Venezuelan hemorrhagic fever virus, vesicular stomatitis virus, Vesiculovirus, Vilyuisk virus, viper retrovirus, viral haemorrhagic septicemia virus, Visna Maedi virus, Visna virus, volepox virus, VSV (vesicular stomatitis virus), Wallal virus, Warrego virus, wart virus, WEE virus, West Nile virus, western equine encephalitis virus, western equine encephalomyelitis virus, Whataroa virus, Winter Vomiting Virus, woodchuck hepatitis B virus, woolly monkey sarcoma virus, wound tumor virus, WRSV virus, Yaba monkey tumor virus, Yaba virus, Yatapoxvirus, yellow fever virus, and the Yug Bogdanovac virus.

Inflammatory Conditions

Inflammatory conditions that can be treated and/or prevented using the methods and compositions provided herein include, for example, autoimmune condition. Autoimmune conditions include, for example, rheumatoid arthritis, multiple sclerosis, Sjogren's syndrome, systemic lupus erythematosus, autoimmune hepatitis, autoimmune thyroiditis, hemophagocytic syndrome (hemophagocytic lymphohistiocytosis), diabetes mellitus type 1, Crohn's condition, ulcerative colitis, psoriasis, psoriatic arthritis, idiopathic thrombocytonpenic pupura, polymyositis, dermatomyositis, myasthenia gravis, autoimmune thryroiditis, Evan's syndrome, autoimmune hemolytic anemia, aplastic anemia, autoimmune neutropenia, scleroderma, Reiter's syndrome, ankylosing spondylitis, pemphnigus, pemphigoid or autoimmune hepatitis, Behçet's condition, Celiac condition, Chagas condition, acute disseminated encephalomyelitis, Addison's condition, antiphospholipid antibody syndrome, autoimmune inner ear condition, bullous pemphigoid, Chronic obstructive pulmonary condition, Goodpasture's syndrome, Graves' condition, Guillain-Barré syndrome, Hashimoto's thyroditis, Hidradenitis suppurativa, Interstitial cystitis, neuromyotonia, pemphigus vulgaris, pernicious anemia, primary biliary cirrhosis, and vasculitis syndromes.

Other inflammatory conditions that can be treated and/or prevented using the methods and compositions of the provided invention include, for example, an allergic condition (e.g., allergic rhinitis, asthma, atopic eczema), a skin condition, coronary artery condition, peripheral artery condition, atherosclerosis, retinitis, pancreatitis, cardiomyopathy, pericarditis, colitis, glomerulonephritis, lung inflammation, esophagitis, gastritis, duodenitis, ileitis, meningitis, encephalitis, encephalomyelitis, transverse myelitis, cystitis, urethritis, mucositis, lymphadenitis, dermatitis, hepatitis, osteomyelitis, or herpes zoster.

Formulations, Routes of Administration, and Effective Doses

Another aspect of the present invention relates to formulations, routes of administration and effective doses for pharmaceutical compositions comprising an agent or combination of agents. Such pharmaceutical compositions can be used to treat a virus-induced inflammatory condition as described above. A pharmaceutical composition can comprise a viral inducing agent. A pharmaceutical composition can comprise a viral inducing agent and one or more additional agents. A pharmaceutical composition can comprise an antiviral agent. A pharmaceutical composition can comprise an antiviral agent and one or more additional agents. A pharmaceutical composition can comprise a viral inducing agent and an antiviral agent. A pharmaceutical composition can comprise a viral inducing agent, an antiviral agent, and one or more additional agents.

The agents or their pharmaceutically acceptable salts can be provided alone or in combination with one or more other agents or with one or more other forms. For example, a formulation can comprise one or more agents in particular proportions, depending on the relative potencies of each agent and the intended indication. For example, in compositions for targeting two different targets and where potencies are similar, about a 1:1 ratio of agents can be used. The two forms can be formulated together, in the same dosage unit e.g. in one cream, suppository, tablet, capsule, enteric coated tablet or capsule, aerosol spray, or packet of powder to be dissolved in a beverage; or each form may be formulated in a separate unit, e.g., two creams, two suppositories, two tablets, two capsules, a tablet and a liquid for dissolving the tablet, two aerosol sprays, or a packet of powder and a liquid for dissolving the powder, etc.

A "pharmaceutically acceptable salt" can be a salt that retains the biological effectiveness and properties of one or more agents, and which are not biologically or otherwise undesirable. For example, a pharmaceutically acceptable salt does not interfere with the beneficial effect of a viral inducing agent or an antiviral agent.

Salts can include those of the inorganic ions, for example, sodium, potassium, calcium, magnesium ions, and the like. Salts can include salts with inorganic or organic acids, for example, hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. If one or more agents contain a carboxy group or other acidic group, it can be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

A pharmaceutically acceptable ester or amide can be an ester or amide that retains biological effectiveness and properties of one or more agents, and which are not biologically or otherwise undesirable. For example, the ester or amide does not interfere with the beneficial effect of a viral inducing agent, an antiviral agent, or an additional agent. Esters can include, for example, ethyl, methyl, isobutyl, ethylene glycol, and the like. Amides include can include, for example, unsubstituted amides, alkyl amides, dialkyl amides, and the like.

A viral inducing agent, for example a HDAC inhibitor, can be administered in combination with an antiviral agent. Pharmaceutical compositions comprising a combination of a viral inducing agent and an antiviral agent can be formulated to comprise certain molar ratios. For example, molar ratios of about 99:1 to about 1:99 of a viral inducing agent to the antiviral agent can be used. The range of molar ratios of viral inducing agent:the antiviral agent can be selected from about 80:20 to about 20:80; about 75:25 to about 25:75, about 70:30 to about 30:70, about 66:33 to about 33:66, about 60:40 to about 40:60; about 50:50; and about 90:10 to about 10:90. The viral inducing agent and the antiviral agent can be co-formulated, in the same dosage unit, e.g., in one cream, suppository, tablet, capsule, enteric coated capsule or tablet, or packet of powder to be dissolved in a beverage; or each agent, form, and/or compound can be formulated in separate units, e.g., two creams, suppositories, tablets, two capsules, enteric coated capsules or tablets, a tablet and a liquid for dissolving the tablet, an aerosol spray a packet of powder and a liquid for dissolving the powder, etc.

An agent can be administered in combination with one or more other compounds, forms, and/or agents, e.g., as described above. Pharmaceutical compositions comprising combinations of a viral inducing agent and/or antiviral agent with one or more other active agents can be formulated to comprise certain molar ratios. For example, molar ratios of about 99:1 to about 1:99 of a viral inducing agent to the other active agent can be used; molar ratios of about 99:1 to about 1:99 of an antiviral agent to the other active agent can be used; molar ratios of about 99:1 to about 1:99 of a viral inducing agent and antiviral agent can be used. The range of molar ratios of viral inducing agent:other active agent can be selected from about 80:20 to about 20:80; about 75:25 to about 25:75, about 70:30 to about 30:70, about 66:33 to about 33:66, about 60:40 to about 40:60; about 50:50; and about 90:10 to about 10:90. The range of molar ratios of an antiviral agent:other active agent can be selected from about 80:20 to about 20:80; about 75:25 to about 25:75, about 70:30 to about 30:70, about 66:33 to about 33:66, about 60:40 to about 40:60; about 50:50; and about 90:10 to about 10:90. The molar ratio may of a viral inducing agent:other active agent can be about 1:9 or about 1:1. The molar ratio may of an antiviral agent:other active agent can be about 1:9 or about 1:1. Two or more agents, forms and/or compounds can be formulated together, in the same dosage unit, e.g., in one cream, suppository, tablet, capsule, enteric coated capsule or tablet, or packet of powder to be dissolved in a beverage; or each agent, form, and/or compound can be formulated in separate units, e.g., two creams, suppositories, tablets, two capsules, enteric coated capsules or tablets, a tablet and a liquid for dissolving the tablet, an aerosol spray a packet of powder and a liquid for dissolving the powder, etc.

A viral inducing agent, for example a HDAC inhibitor, can be administered in combination with an antiviral agent. Pharmaceutical compositions comprising a combination of a viral inducing agent and an antiviral agent can be formulated to comprise certain mg per dose. For example, a viral inducing agent can be administered at 0.01, 0.05, 0.1, 0.5, 1, 2, 5, 10, 20, 25, 50, 100, 250, 500, 1000 mg/kg per dose. A HDAC inhibitor can be administered at 0.01-0.1, 0.05-0.5, 1-2, 1-5, 5-10, 10-20, 10-25, 10-50, 100-500, or 500-1000 mg/kg per dose. A single dose of an oral formulation of a viral inducing agent can contain 0.01, 0.05, 0.1, 0.5, 1, 2, 5, 10, 20, 25, 50, 100, 250, 500, 1000 mg. In one embodiment, the HDAC inhibitor is administered at 0.01, 0.05, 0.1, 0.5, 1, 2, 5, 10, 20, 25, 50, 100, 250, 500, 1000 mg/kg per dose. In a related embodiment, the HDAC inhibitor is administered orally. In a specific embodiment, the total daily oral dose of a HDAC inhibitor is no more than 1, 2, 5, 10, 20, 25, 40, 50, 100, 250, or 500 mg. In another related embodiment, the HDAC inhibitor is administered 1, 2, 3, 4, or 5 times a day orally. In other embodiments, a single daily dose of a HDAC inhibitor is provided whereas oral valganciclovir is provided at 900 mgs/dose, two times a day.

An oral formulation of an HDAC inhibitor can be co-formulated with an antiviral agent, such as valganciclovir. In a specific embodiment when an HDAC inhibitor and valganciclovir are co-formulated for a single daily dose, the valganciclovir is present in a slow release or timed release form. In certain embodiments, the HDAC inhibitor and valganciclovir or other antiviral agent are co-formulated such that the HDAC inhibitor is present at no more than 100 mg per dose, and the antiviral agent is present at no more than 1000 mg per dose. In some embodiments, the HDAC inhibitor and valganciclovir or other antiviral agent are co-formulated such that the HDAC inhibitor is present at no more than 80 mg per dose, and the antiviral agent is present at no more than 500 mg per dose. In certain embodiments, the HDAC inhibitor and valganciclovir or other antiviral agent are co-formulated such that the HDAC inhibitor is present at not greater than 80 mg per dose, and the antiviral agent is present at not greater than 1500 mg per dose.

In some embodiments, a co-formulation comprising an HDAC inhibitor and an antiviral agent comprises less than 500 mg, less than 400 mg, less than 300 mg, less than 200 mg, less than 100 mg, less than 90 mg, less than 80 mg, less than 70 mg, less than 60 mg, less than 50 mg, less than 40 mg, less than 30 mg, less than 20 mg, less than 10 mg, less than 5 mg, less than 2 mg, or less than 1 mg of the HDAC inhibitor. In other embodiments, a co-formulation comprising an HDAC inhibitor and an antiviral agent comprises less than 1500 mg, less than 1400 mg, less than 1300 mg, less than 1200 mg, less than 1100 mg, less than 1000 mg, less than 900 mg, less than 800 mg, less than 700 mg, less than 600 mg, less than 500 mg, less than 400 mg, less than 300 mg, less than 200 mg, less than 100 mg, less than 90 mg, less than 80 mg, less than 70 mg, less than 60 mg, less than 50 mg, less than 40 mg, less than 30 mg, less than 20 mg, less than 10 mg, less than 5 mg, less than 2 mg, or less than 1 mg of the antiviral agent.

In certain embodiments, a unit dose of a co-formulated HDAC inhibitor and antiviral agent comprises between about 1 mg and about 500 mg of the HDAC inhibitor and between 1 mg and 1500 mg of the antiviral agent. In some embodiments, the unit dose comprises about 500 mg, about 400 mg, about 300 mg, about 200 mg, about 100 mg, about 90 mg, about 80 mg, about 70 mg, about 60 mg, about 50 mg, about 40 mg, about 30 mg, about 20 mg, about 10 mg, about 5 mg, about 2 mg, or about 1 mg of the HDAC inhibitor. In certain embodiments, the unit dose comprises less than 500 mg, less than 400 mg, less than 300 mg, less than 200 mg, less than 100 mg, less than 90 mg, less than 80 mg, less than 70 mg, less than 60 mg, less than 50 mg, less than 40 mg, less than 30 mg, less than 20 mg, less than 10 mg, less than 5 mg, less than 2 mg, or less than 1 mg of an HDAC inhibitor. In some embodiments, the unit dose comprises more than 500 mg, more than 400 mg, more than 300 mg, more than 200 mg, more than 100 mg, more than 90 mg, more than 80 mg, more than 70 mg, more than 60 mg, more than 50 mg, more than 40 mg, more than 30 mg, more than 20 mg, more than 10 mg, more than 5 mg, more than 2 mg, or more than 1 mg of an HDAC inhibitor. In certain embodiments, the unit dose comprises more than 2 mg and less than 500 mg of an HDAC inhibitor. In some embodiments, the unit dose comprises more than 10 mg and less than 50 mg of an HDAC inhibitor.

In some embodiments, the unit dose comprises about 2000 mg, about 1900 mg, about 1800 mg, about 1700 mg, about 1600 mg, comprises about 1500 mg, about 1400 mg, about 1300 mg, about 1200 mg, about 1100 mg, about 1000 mg, about 900 mg, about 800 mg, about 750 mg, about 700 mg, about 650 mg, about 600 mg, about 550 mg, about 500 mg, about 450 mg, about 400 mg, about 350 mg, about 300 mg, about 250 mg, about 200 mg, about 150 mg, about 140 mg, about 130 mg, about 120 mg, about 110 mg, about 100 mg, about 90 mg, about 80 mg, about 70 mg, about 60 mg, about 50 mg, about 40 mg, about 30 mg, about 20 mg, about 10 mg, about 5 mg, about 2 mg, or about 1 mg of the antiviral agent. In certain embodiments, the unit dose comprises less than 2000 mg, less than 1900 mg, less than 1800 mg, less than 1700 mg, less than 1600 mg, comprises less than 1500 mg, less than 1400 mg, less than 1300 mg, less than 1200 mg, less than 1100 mg, less than 1000 mg, less than 900 mg, less than 800 mg, less than 750 mg, less than 700 mg, less than 650 mg, less than 600 mg, less than 550 mg, less than 500 mg, less than 450 mg, less than 400 mg, less than 350 mg, less than 300 mg, less than 250 mg, less than 200 mg, less than 150 mg, less than 140 mg, less than 130 mg, less than 120 mg, less than 110 mg, less than 100 mg, less than 90 mg, less than 80 mg, less than 70 mg, less than 60 mg, less than 50 mg, less than 40 mg, less than 30 mg, less than 20 mg, less than 10 mg, less than 5 mg, less than 2 mg, or less than 1 mg of the antiviral agent. In some embodiments, the unit dose comprises more than 2000 mg, more than 1900 mg, more than 1800 mg, more than 1700 mg, more than 1600 mg, comprises more than 1500 mg, more than 1400 mg, more than 1300 mg, more than 1200 mg, more than 1100 mg, more than 1000 mg, more than 900 mg, more than 800 mg, more than 750 mg, more than 700 mg, more than 650 mg, more than 600 mg, more than 550 mg, more than 500 mg, more than 450 mg, more than 400 mg, more than 350 mg, more than 300 mg, more than 250 mg, more than 200 mg, more than 150 mg, more than 140 mg, more than 130 mg, more than 120 mg, more than 110 mg, more than 100 mg, more than 90 mg, more than 80 mg, more than 70 mg, more than 60 mg, more than 50 mg, more than 40 mg, more than 30 mg, more than 20 mg, more than 10 mg, more than 5 mg, more than 2 mg, or more than 1 mg of the antiviral agent. In certain embodiments, the unit dose comprises more than 50 mg and less than 1500 mg of the antiviral agent. In some embodiments, the unit dose comprises more than 100 mg and less than 500 mg of the antiviral agent. In certain embodiments, the antiviral agent is formulated as slow release.

In some embodiments, the co-formulated HDAC inhibitor and antiviral agent are administered once a day. In certain embodiments, the co-formulated HDAC inhibitor and antiviral agent are administered twice a day. In other embodiments, the co-formulated HDAC inhibitor and antiviral agent are administered thrice a day. In some embodiments, the co-formulated HDAC inhibitor and antiviral agent are administered once a day, twice a day, or thrice a day, and a further dose of the HDAC inhibitor is administered once, twice, or thrice a day. In certain embodiments, the co-formulated HDAC inhibitor and antiviral agent are administered once a day, twice a day, or thrice a day, and a further dose of the antiviral agent is administered once, twice, or thrice a day.

In certain embodiments, one unit dose of the co-formulated HDAC inhibitor and antiviral agent are administered per day. In some embodiments, two unit doses of the co-formulated HDAC inhibitor and antiviral agent are administered per day. In certain embodiments, three unit doses of the co-formulated HDAC inhibitor and antiviral agent are administered per day. In some embodiments, four unit doses of the co-formulated HDAC inhibitor and antiviral agent are administered per day. In certain embodiments, the one, two, three, or four unit doses are administered daily, once a week, twice a week, three times a week, four times a week, or five times a week.

In some embodiments, one or more unit doses of the co-formulated HDAC inhibitor and antiviral agent are administered in combination with other treatments, such as antibodies, chemotherapy drugs, and radiation therapy.

One or more agents and/or combinations of agents can be administered with still other agents. The choice of agents that can be co-administered with the agents and/or combinations of agents can depend, at least in part, on the condition being treated. Agents of particular use in the formulations of the present invention include, for example, any agent having a therapeutic effect for a virus-induced inflammatory condition, including, e.g., drugs used to treat inflammatory conditions. For example, formulations of the instant invention can additionally contain one or more conventional anti-inflammatory drugs, such as an NSAID, e.g. ibuprofen, naproxen, acetominophen, ketoprofen, or aspirin. In some alternative embodiments for the treatment of a virus-induced inflammatory condition can additionally contain one or more conventional influenza antiviral agents, such as amantadine, rimantadine, zanamivir, and oseltamivir. In treatments for retroviral infections, such as HIV, formulations of the instant invention may additionally contain one or more conventional antiviral drug, such as protease inhibitors (lopinavir/ritonavir {Kaletra™}, indinavir {Crixivan™}, ritonavir {Norvir™}, nelfinavir {Viracept™}, saquinavir hard gel capsules {Invirase™}, atazanavir {Reyataz™}, amprenavir {Agenerase™}, fosamprenavir {Telzir™}, tipranavir{Aptivus™}), reverse transcriptase inhibitors, includingnon-Nucleoside and Nucleoside/nucleotide inhibitors (AZT {zidovudine, Retrovir™}, ddI {didanosine, Videx™}, 3TC {lamivudine, Epivir™}, d4T {stavudine, Zerit™}, abacavir {Ziagen™}, FTC {emtricitabine, Emtriva™}, tenofovir {Viread™}, efavirenz {Sustiva™} and nevirapine {Viramune™}), fusion inhibitors T20 {enfuvirtide, Fuzeon™}, integrase inhibitors (MK-0518 and GS-9137), and maturation inhibitors (PA-457 {Bevirimat™}). As another example, formulations can additionally contain one or more supplements, such as vitamin C, E or other anti-oxidants.

One or more agents (or pharmaceutically acceptable salts, esters or amides thereof) can be administered per se or in the form of a pharmaceutical composition wherein the one or more active agent(s) is in an admixture or mixture with one or more pharmaceutically acceptable carriers. A pharmaceutical composition, as used herein, can be any composition prepared for administration to a subject. Pharmaceutical compositions can be formulated in conventional manner using one or more physiologically acceptable carriers, comprising excipients, diluents, and/or auxiliaries, e.g., that facilitate processing of the active agents into preparations that can be administered. Proper formulation can depend at least in part upon the route of administration chosen. One or more agents, or pharmaceutically acceptable salts, esters, or amides thereof, can be delivered to a patient using a number of routes or modes of administration, including oral, buccal, topical, rectal, transdermal, transmucosal, subcutaneous, intravenous, and intramuscular applications, as well as by inhalation.

For oral administration, one or more agents can be formulated readily by combining the one or more active agents with pharmaceutically acceptable carriers well known in the art. Such carriers can enable the one or more agents to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including solid diluents or fillers, sterile aqueous media and various non-toxic organic solvents. Generally, the agents of the invention can be included at concentration levels ranging from about 0.5%, about 5%, about 10%, about 20%, or about 30% to about 50%, about 60%, about 70%, about 80% or about 90% by weight of the total composition of oral dosage forms, in an amount sufficient to provide a desired unit of dosage.

Aqueous suspensions for oral use can contain one or more agents with pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like.

Oils or non-aqueous solvents can be required to bring one or more agents into solution, due to, for example, the presence of large lipophilic moieties. Alternatively, emulsions, suspensions, or other preparations, for example, liposomal preparations, can be used. With respect to liposomal preparations, any known methods for preparing liposomes for treatment of a condition can be used. See, for example, Bangham et al., J. Mol. Biol. 23: 238-252 (1965) and Szoka et al., Proc. Natl Acad. Sci. USA 75: 4194-4198 (1978), incorporated herein by reference. Ligands can also be attached to the liposomes to direct these compositions to particular sites of action. One or more agents can also be integrated into foodstuffs, e.g, cream cheese, butter, salad dressing, or ice cream to facilitate solubilization, administration, and/or compliance in certain patient populations.

Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). Disintegrating agents can be added, for example, the cross-linked polyvinyl pyrrolidone, agar, or alginic acid or a salt thereof such as sodium alginate. One or more agents can also be formulated as a sustained release preparation.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of one or more active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active agents can be dissolved or suspended in suitable liquids, such as fatty oils, liquid paraffin, or liquid polyethylene glycols. In addition, stabilizers can be added. All formulations for oral administration can be in dosages suitable for administration.

For injection, one or more agents can be formulated in aqueous solutions, including but not limited to physiologically compatible buffers such as Hank's solution, Ringer's solution, or physiological saline buffer. Such compositions can also include one or more excipients, for example, preservatives, solubilizers, fillers, lubricants, stabilizers, albumin, and the like. Methods of formulation are known in the art, for example, as disclosed in Remington's Pharmaceutical Sciences, latest edition, Mack Publishing Co., Easton P.

One or more agents can also be formulated as a depot preparation. Such long acting formulations can be administered by implantation or transcutaneous delivery (for example subcutaneously or intramuscularly), intramuscular injection or use of a transdermal patch. Thus, for example, one or more agents can be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising one or more agents can exert local and regional effects when administered topically or injected at or near particular sites of infection. Direct topical application, e.g., of a viscous liquid, gel, jelly, cream, lotion, ointment, suppository, foam, or aerosol spray, can be used for local administration, to produce, for example local and/or regional effects. Pharmaceutically appropriate vehicles for such formulation include, for example, lower aliphatic alcohols, polyglycols (e.g., glycerol or polyethylene glycol), esters of fatty acids, oils, fats, silicones, and the like. Such preparations may also include preservatives (e.g., p-hydroxybenzoic acid esters) and/or antioxidants (e.g., ascorbic acid and tocopherol). See also Dermatological Formulations: Percutaneous absorption, Barry (Ed.), Marcel Dekker Incl, 1983. In some embodiments, local/topical formulations comprising a viral inducing agent and or antiviral agent are used to treat epidermal or mucosal viral-induced inflammatory condition.

Pharmaceutical compositions can contain a cosmetically or dermatologically acceptable carrier. Such carriers can be compatible with skin, nails, mucous membranes, tissues and/or hair, and can include any conventionally used cosmetic or dermatological carrier meeting these requirements. Such carriers can be readily selected by one of ordinary skill in the art. In formulating skin ointments, an agent or combination of agents can be formulated in an oleaginous hydrocarbon base, an anhydrous absorption base, a water-in-oil absorption base, an oil-in-water water-removable base and/or a water-soluble base.

The compositions according to the present invention can be in any form suitable for topical application, including aqueous, aqueous-alcoholic or oily solutions, lotion or serum dispersions, aqueous, anhydrous or oily gels, emulsions obtained by dispersion of a fatty phase in an aqueous phase (O/W or oil in water) or, conversely, (W/O or water in oil), microemulsions or alternatively microcapsules, microparticles or lipid vesicle dispersions of ionic and/or nonionic type. These compositions can be prepared according to conventional methods. The amounts of the various constituents of the compositions according to the invention can be those conventionally used in the art. These compositions constitute protection, treatment or care creams, milks, lotions, gels or foams for the face, for the hands, for the body and/or for the mucous membranes, or for cleansing the skin. The compositions can also consist of solid preparations constituting soaps or cleansing bars.

A pharmaceutical composition can also contain adjuvants common to the cosmetic and dermatological fields, for example, hydrophilic or lipophilic gelling agents, hydrophilic or lipophilic active agents, preserving agents, antioxidants, solvents, fragrances, fillers, sunscreens, odor-absorbers and dyestuffs. The amounts of these various adjuvants can be those conventionally used in the fields considered and, for example, are from about 0.01% to about 20% of the total weight of the composition. Depending on their nature, these adjuvants can be introduced into the fatty phase, into the aqueous phase and/or into the lipid vesicles.

Ocular viral infections can be effectively treated with ophthalmic solutions, suspensions, ointments or inserts comprising an agent or combination of agents of the present invention.

In some embodiments, viral infections of the ear can be effectively treated with otic solutions, suspensions, ointments or inserts comprising an agent or combination of agents of the present invention.

One or more agents can be delivered in soluble rather than suspension form, which can allow for more rapid and quantitative absorption to the sites of action. In general, formulations such as jellies, creams, lotions, suppositories and ointments can provide an area with more extended exposure to the agents of the present invention, while formulations in solution, e.g., sprays, provide more immediate, short-term exposure.

Relating to topical/local application, a pharmaceutical composition can include one or more penetration enhancers. For example, the formulations can comprise suitable solid or gel phase carriers or excipients that increase penetration or help delivery of agents or combinations of agents of the invention across a permeability barrier, e.g., the skin. Many of these penetration-enhancing compounds are known in the art of topical formulation, and include, e.g., water, alcohols (e.g., terpenes like methanol, ethanol, 2-propanol), sulfoxides (e.g., dimethyl sulfoxide, decylmethyl sulfoxide, tetradecylmethyl sulfoxide), pyrrolidones (e.g., 2-pyrrolidone, N-methyl-2-pyrrolidone, N-(2-hydroxyethyl)pyrrolidone), laurocapram, acetone, dimethylacetamide, dimethylformamide, tetrahydrofurfuryl alcohol, L-α-amino acids, anionic, cationic, amphoteric or nonionic surfactants (e.g., isopropyl myristate and sodium lauryl sulfate), fatty acids, fatty alcohols (e.g., oleic acid), amines, amides, clofibric acid amides, hexamethylene lauramide, proteolytic enzymes, α-bisabolol, d-limonene, urea and N,N-diethyl-m-toluamide, and the like. Additional examples include humectants (e.g., urea), glycols (e.g., propylene glycol and polyethylene glycol), glycerol monolaurate, alkanes, alkanols, ORGELASE, calcium carbonate, calcium phosphate, various sugars, starches, cellulose derivatives, gelatin, and/or other polymers. A pharmaceutical composition can include one or more such penetration enhancers.

A pharmaceutical composition for local/topical application can include one or more antimicrobial preservatives, for example, quaternary ammonium compounds, organic mercurials, p-hydroxy benzoates, aromatic alcohols, chlorobutanol, and the like.

Gastrointestinal viral infections can be effectively treated with orally- or rectally delivered solutions, suspensions, ointments, enemas and/or suppositories comprising an agent or combination of agents of the present invention.

Respiratory viral infections can be effectively treated with aerosol solutions, suspensions or dry powders comprising an agent or combination of agents of the present invention. Administration by inhalation is particularly useful in treating viral infections of the lung, such as influenza. The aerosol can be administered through the respiratory system or nasal passages. For example, one skilled in the art will recognize that a composition of the present invention can be suspended or dissolved in an appropriate carrier, e.g., a pharmaceutically acceptable propellant, and administered directly into the lungs using a nasal spray or inhalant. For example, an aerosol formulation comprising a viral inducing agent and/or antiviral agent can be dissolved, suspended or emulsified in a propellant or a mixture of solvent and propellant, e.g., for administration as a nasal spray or inhalant. Aerosol formulations may contain any acceptable propellant under pressure, such as a cosmetically or dermatologically or pharmaceutically acceptable propellant, as conventionally used in the art.

An aerosol formulation for nasal administration is generally an aqueous solution designed to be administered to the nasal passages in drops or sprays. Nasal solutions can be similar to nasal secretions in that they are generally isotonic and slightly buffered to maintain a pH of about 5.5 to about 6.5, although pH values outside of this range can additionally be used. Antimicrobial agents or preservatives can also be included in the formulation.

An aerosol formulation for inhalations and inhalants can be designed so that an agent or combination of agents can be carried into the respiratory tree of the subject when administered by the nasal or oral respiratory route. Inhalation solutions can be administered, for example, by a nebulizer. Inhalations or insufflations, comprising finely powdered or liquid drugs, can be delivered to the respiratory system as a pharmaceutical aerosol of a solution or suspension of the agent or combination of agents in a propellant, e.g., to aid in disbursement. Propellants can be liquefied gases, including halocarbons, for example, fluorocarbons such as fluorinated chlorinated hydrocarbons, hydrochlorofluorocarbons, and hydrochlorocarbons, as well as hydrocarbons and hydrocarbon ethers.

Halocarbon propellants can include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Halocarbon propellants are described in Johnson, U.S. Pat. No. 5,376,359, issued Dec. 27, 1994; Byron et al., U.S. Pat. No. 5,190,029, issued Mar. 2, 1993; and Purewal et al., U.S. Pat. No. 5,776,434, issued Jul. 7, 1998. Hydrocarbon propellants useful in the invention include, for example, propane, isobutane, n-butane, pentane, isopentane and neopentane. A blend of hydrocarbons can also be used as a propellant. Ether propellants include, for example, dimethyl ether as well as the ethers. An aerosol formulation of the invention can also comprise more than one propellant. For example, an aerosol formulation can comprise more than one propellant from the same class, such as two or more fluorocarbons; or more than one, more than two, more than three propellants from different classes, such as a fluorohydrocarbon and a hydrocarbon. Pharmaceutical compositions of the present invention can also be dispensed with a compressed gas, e.g., an inert gas such as carbon dioxide, nitrous oxide or nitrogen.

Aerosol formulations can also include other components, for example, ethanol, isopropanol, propylene glycol, as well as surfactants or other components such as oils and detergents. These components can serve to stabilize the formulation and/or lubricate valve components.

The aerosol formulation can be packaged under pressure and can be formulated as an aerosol using solutions, suspensions, emulsions, powders and semisolid preparations. For example, a solution aerosol formulation can comprise a solution of an agent, such as a viral inducing agent and/or antiviral agent in (substantially) pure propellant or as a mixture of propellant and solvent. The solvent can be used to dissolve the agent and/or retard the evaporation of the propellant. Solvents useful in the invention include, for example, water, ethanol and glycols. Any combination of suitable solvents can be used, optionally combined with preservatives, antioxidants, and/or other aerosol components.

An aerosol formulation can also be a dispersion or suspension. A suspension aerosol formulation may comprise a suspension of an agent or combination of agents of the instant invention, e.g., a viral inducing agent and/or antiviral agent, and a dispersing agent. Dispersing agents useful in the invention include, for example, sorbitan trioleate, oleyl alcohol, oleic acid, lecithin and corn oil. A suspension aerosol formulation can also include lubricants, preservatives, antioxidant, and/or other aerosol components.

An aerosol formulation can be formulated as an emulsion. An emulsion aerosol formulation can include, for example, an alcohol such as ethanol, a surfactant, water and a propellant, as well as an agent or combination of agents, e.g., a viral inducing agent and/or an antiviral agent. The surfactant used can be nonionic, anionic or cationic. One example of an emulsion aerosol formulation comprises, for example, ethanol, surfactant, water and propellant. Another example of an emulsion aerosol formulation comprises, for example, vegetable oil, glyceryl monostearate and propane.

Pharmaceutical compositions suitable for use in the present invention can include compositions wherein the active ingredients are present in an effective amount, i.e., in an amount effective to achieve therapeutic and/or prophylactic benefit in a host with at least one virus-induced inflammatory condition. The actual amount effective for a particular application will depend on the condition or conditions being treated, the condition of the subject, the formulation, and the route of administration, as well as other factors known to those of skill in the art. Determination of an effective amount of a viral inducing agent and/or antiviral agent is well within the capabilities of those skilled in the art, in light of the disclosure herein, and can be determined using routine optimization techniques.

An effective amount for use in humans can be determined from animal models. For example, a dose for humans can be formulated to achieve circulating, liver, topical and/or gastrointestinal concentrations that have been found to be effective in animals. One skilled in the art can determine the effective amount for human use, especially in light of the animal model experimental data described herein. Based on animal data, and other types of similar data, those skilled in the art can determine an effective amount of a composition appropriate for humans.

An effective amount when referring to an agent or combination of agents of the invention can generally mean the dose ranges, modes of administration, formulations, etc., that have been recommended or approved by any of the various regulatory or advisory organizations in the medical or pharmaceutical arts (e.g., FDA, AMA) or by the manufacturer or supplier.

Further, appropriate doses for a viral inducing agent and/or antiviral agent can be determined based on in vitro experimental results.

A person of skill in the art would be able to monitor in a patient the effect of administration of a particular agent. For example, HIV or EBV viral load levels can be determined by techniques standard in the art, such as measuring CD4 cell counts, and/or viral levels as detected by PCR. Other techniques would be apparent to one of skill in the art.

Administration Schedule

Administration of one or more agents (e.g, a viral inducing agent and/or an antiviral) can be intermittent; for example, administration can be once every two days, every three days, every five days, once a week, once or twice a month, and the like. The amount, forms, and/or amounts of the different forms can be varied at different times of administration.

Pulsed administration of one or more pharmaceutical compositions can be used for the treatment or prevention of a viral-induced inflammatory condition. Pulsed administration can be more effective than continuous treatment as pulsed doses can be lower than would be expected from continuous administration of the same composition. Each pulse dose can be reduced and the total amount of drug administered over the course of treatment to the patient can be minimized.

With pulse therapy, in vivo levels of an agent can drop below that level required for effective continuous treatment. Pulsed administration can reduce the amount of the composition administered to the patient per dose or per total treatment regimen with an increased effectiveness. Pulsed administration can provide a saving in time, effort and expense and a lower effective dose can lessen the number and severity of complications that can be experienced by a subject. As such, pulsing can be more effective than continuous administration of the same composition.

Individual pulses can be delivered to a subject continuously over a period of several hours, such as about 2, 4, 6, 8, 10, 12, 14 or 16 hours, or several days, such as 2, 3, 4, 5, 6, or 7 days, or from about 1 hour to about 24 hours or from about 3 hours to about 9 hours. Alternatively, periodic doses can be administered in a single bolus or a small number of injections of the composition over a short period of time, for example, less than 1 or 2 hours. For example, arginine butyrate can be administered over a period of 4 days with infusions for about 8 hours per day or overnight, followed by a period of 7 days of no treatment.

The interval between pulses or the interval of no delivery can be greater than 24 hours or can be greater than 48 hours, and can be for even longer such as for 3, 4, 5, 6, 7, 8, 9 or 10 days, two, three or four weeks or even longer. The interval between pulses can be determined by one of ordinary skill in the art. The interval between pulses can be calculated by administering another dose of the composition when the composition or the active component of the composition is no longer detectable in the patient prior to delivery of the next pulse. Intervals can also be calculated from the in vivo half-life of the composition. Intervals can be calculated as greater than the in vivo half-life, or 2, 3, 4, 5 and even 10 times greater than the composition half-life. Intervals can be 25, 50, 100, 150, 200, 250 300 and even 500 times the half life of the chemical composition.

The number of pulses in a single therapeutic regimen can be as little as two, but can be from about 5 to 10, 10 to 20, 15 to 30 or more. Subjects (e.g., patients) can receive one or more agents (e.g., drugs) for life according to the methods of this invention. Compositions can be administered by most any means, and can be delivered to the patient as an injection (e.g. intravenous, subcutaneous, intraarterial), infusion or instillation, and more preferably by oral ingestion. Various methods and apparatus for pulsing compositions by infusion or other forms of delivery to the patient are disclosed in U.S. Pat. Nos. 4,747,825; 4,723,958; 4,948,592; 4,965,251 and 5,403,590.

In certain embodiments, the co-formulated unit dose comprising an HDAC inhibitor and an antiviral agent is administered daily. In further embodiments, administration is continuous. In some embodiments, the administration of the co-formulated unit dose is by pulsed administration. In certain embodiments, pulsed administration comprises administering pulses of the co-formulated unit dose for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In some embodiments, pulsed administration comprises intervals of not administering the co-formulated unit dose of about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months.

In some embodiments, the administration of the co-formulated unit dose is by pulsed administration. In certain embodiments, the pulsed administration comprises administering the co-formulated unit dose for about 8 weeks, followed by not administering the co-formulated unit dose for about 4 weeks. In some embodiments, the pulsed administration comprises administering the co-formulated unit dose for about 6 weeks, followed by not administering the co-formulated unit dose for about 2 weeks. In certain embodiments, the pulsed administration comprises administering the co-formulated unit dose for about 4 weeks, followed by not administering the co-formulated unit dose for about 2 weeks. In some embodiments, the pulsed administration comprises administering the co-formulated unit dose for about 2 weeks, followed by not administering the co-formulated unit dose for about 2 weeks. In some embodiments, pulsed administration comprises pulses of administering the co-formulated unit dose for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In certain embodiments, pulsed administration comprises intervals of not administering the co-formulated unit dose of about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In some embodiments, administration is continuous. In certain embodiments, administration is for the lifetime of the subject. In other embodiments, administration is for about 1 week, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, or about 12 months. In some embodiments, an antiviral agent is administered during intervals of not administering the co-formulated unit dose. In certain embodiments, an antiviral agent is administered in addition to the co-formulated unit dose. In some embodiments, an antiviral agent is administered simultaneously with the co-formulated unit dose. In other embodiments, an antiviral agent is administered separate from the co-formulated unit dose.

A pharmaceutical composition comprising a viral inducing agent can be administered to a subject before a pharmaceutical composition comprising an antiviral agent is administered to the subject. A pharmaceutical composition comprising a viral inducing agent can be co-administered to a subject with a pharmaceutical composition comprising an antiviral agent. A pharmaceutical composition comprising a viral inducing agent can be co-administered with a pharmaceutical composition comprising an antiviral agent and a pharmaceutical composition comprising one or more addition agents. The pharmaceutical compositions can be provided by pulsed administration. For example, a pharmaceutical composition comprising a viral inducing agent can be administered to a subject, followed by administration of a pharmaceutical composition comprising an antiviral agent to the subject after an interval of time has passed, and this order of administration the same or similar time interval can be repeated, for example, at least 1, 2, 3, 4, 5, 6, 7, 8, 9, or 10 or more times.

EXAMPLES

Example 1. Phase 1 Study of AB Plus Ganciclovir in Patients with EBV Associated Lymphoid Malignancies Fifteen patients with EBV-associated lymphoid malignancies, who had histologically confirmed lymphoid neoplasms that were EBV+, were treated with AB and GCV. Prior therapies (varying in different subjects) included rituximab, chemotherapy, chemoradiotherapy and bone marrow transplant. GCV was administered at a rate of 5 mg/kg intravenously (IV) over 1 hour twice per day, and continued throughout the cycle. AB was continuously infused at a starting dose of 500 mg/kg/day. Dose escalation was continued as follows until MTD was established:
Level 1: 500 mg/kg/day IV for 2 days
Level 2: 1000 mg/kg/day IV for 2 days
Level 3: 1500 mg/kg/day IV for 2 days
Level 4: 2000 mg/kg/day IV until day 21

A total of 15 patients were evaluated for anti-tumor response (Table 1). A complete response (CR) was defined as disappearance of detectable malignant disease on imaging or physical examination (e.g., for skin lesions or tonsillar masses). A partial response (PR) was defined as a 50% decrease in tumor size (the sum of the product of the largest perpendicular diameters) or measurable lesions chosen for analysis prior to beginning of treatment. For lesions which could only be measured in 1 dimension, such as skin (cutaneous T cell lymphoma), a greater than 50% decrease in the largest dimension qualified as a PR. For the 3 patients who died from co-morbidities, anti-tumor responses were confirmed pathologically at autopsy.

TABLE 1

Treatment Courses in Patients with EBV Associated Lymphoid Malignancies Treated with AB and GCV

| Patient Number | No. Cycles | HD/HTD[1] (mg/kg/day) | Outcome, 1 cycle | Adverse Events |
|---|---|---|---|---|
| 1 | <1, 15 d | 500 | CR | confusion; diarrhea; emesis; rejection of lung transplant* |
| 2 | <1, 16 d | 1800 | CR | confusion; mucositis; headache; nausea; vomiting; abdominal pain |
| 3 | <1, 19 d | 2000 | PR | confusion; mucositis; headache; nausea/vomiting; tumor regression preceding bowel perforation* |
| 4 | 1 | 2000 | PR | confusion: nausea/vomiting; anorexia |
| 5 | 1 | 2000 | NR | confusion; restlessness; somnolence; nausea; vomiting; abdominal pain; vision change; orthostasis |
| 6 | 1 | 1000/1000 | NR | Headache; nausea/vomiting; abdominal pain; thrombocytopenia |
| 7 | 1 | 2000/1500 | CR | Lethargy/stupor/confusion; hypotonia/hypoesthesia; fungal infection/mucositis; tumor lysis leading to hemorrhage* |
| 8 | 1 | 1500/1000 | PR | Acoustic hallucinations; somnolence; hypokalemia; sepsis; Deep Vein Thrombosis |
| 9 | 1 | 2000/2000 | CR | Confusion; fatigue; elevated BUN; tumor lysis leading to pancreatitis/hepatitis* |

TABLE 1-continued

Treatment Courses in Patients with EBV Associated
Lymphoid Malignancies Treated with AB and GCV

| Patient Number | No. Cycles | HD/HTD[1] (mg/kg/day) | Outcome, 1 cycle | Adverse Events |
|---|---|---|---|---|
| 10 | 1 | 1000/800 | NR | Elevated BUN, encephalopathy |
| 11 | <1, 8 d | 1500/1500 | PR | Diarrhea; hepatomegaly |
| 12 | 1 | 2000/2000 | NR | Nausea; pneumonia; port infection |
| 13 | 3 | 938/938 | PR | Nausea; anorexia; weight loss; anemia; thrombocytopenia; lethargy; insomnia; hypokalemia |
| 14 | <1, 19 d | 1250/1250 | NR | Sinus, throat, back pain; thrombocytopenia; hypokalemia; lethargy |
| 15 | <1, 5 d | 1000/1000 | PR | Lethargy; increased dyspnea; polymicrobial pneumonia/acute respiratory distress syndrome |

*fatal AE;
[1]HD/HTD—highest dose/highest tolerated dose.

Four patients were classified as achieving CRs, including 2 with PTLD, 1 with extranodal NK/T cell lymphoma and 1 with peripheral T-cell lymphoma. Three of these patients died after completing therapy as a result of co-morbid conditions and complications presumed related to tumor regression. Autopsy examination of 2 subjects revealed apparent complete disappearance of tumor, while the third patient demonstrated significant necrosis of residual lymphoma at autopsy.

Six patients were classified as partial responses (PRs), including 3 with PTLD, 1 with diffuse large-cell B-cell lymphoma, 1 with extranodal NK/T-cell lymphoma and 1 with subcutaneous panniculitis-like T-cell lymphoma.

The remaining 5 patients were classified as non-responders (NR).

In summary 10 out of 15 patients showed a degree of response to treatment of AB in combination with the anti-viral ganciclovir.

Example 2. Phase II Trial of Low-Dose Arginine Butyrate and Ganciclovir/Valganciclovir in EBV(+) Lymphoid Malignancies It has previously been found that continuous infusion of inducing agent, for example, arginine butyrate, may not be necessary to maintain viral thymidine kinase expression and sensitization to anti-viral agents in EBV-associated tumors, but that, in fact, cells that survived initial exposure to the inducing agent plus the anti-viral agent remained susceptible to further cycles of combination treatment (Ghosh, S. K., et al. 2007 Blood *Cells, Molecules, and Diseases* 38:57-65, incorporated herein in its entirety). However, it was neither anticipated nor expected that after some first period of treatment with inducing agent and anti-viral agent, one could continue the anti-viral treatment effectively within a cycle of therapy without continued administration of the inducing agent (continued administration including continued periods of pulsing throughout).

A clinical trial was instituted utilizing a 5-day infusion of arginine butyrate and 21 days of ganciclovir/valganciclovir for EBV+ lymphomas and Post-transplant Lymphoproliferative Disorder (PTLD). The first patient enrolled in the protocol (with Rituximab-refractory PTLD following a cord stem cell transplantation for Hodgkin Disease) tolerated the treatment regimen well, with resolution of cough within three days and a decrease in LDH levels.

Figure 1B:
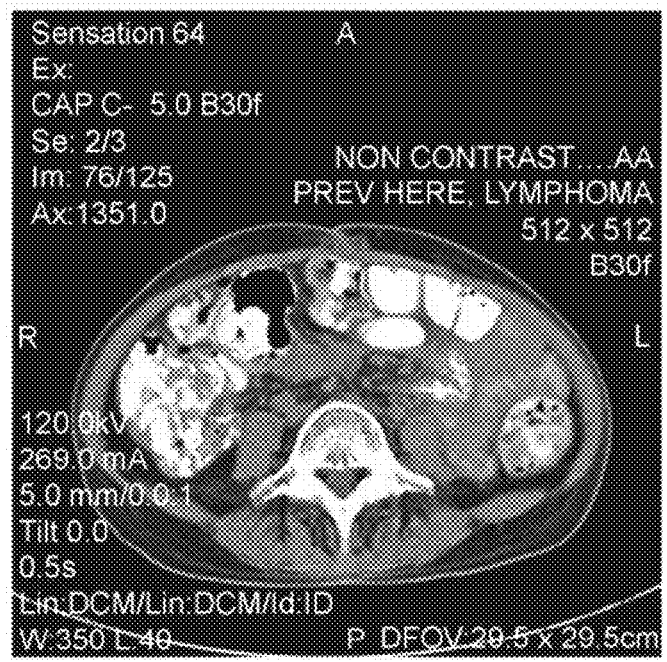

Treatment with arginine butyrate (AB) was administered in a hospital/inpatient basis. The subject was a 32 year old with EBV-related post-transplant lymphoma who had failed multiple therapies (chemotherapy, Rituxan). The subject received AB 1,000 mg/kg/dose intravenously for 5 days (day 1-5). The dose was given continuously over 24 hours. AB was given through a long IV line or port due to hypertonicity. Ganciclovir at 5 mg/kg IV over 1 hour was given twice a day for five days (day 1-5). Valganciclovir 900 mg was given orally twice per day for 16 days (day 6-21). At the end of the 21-day cycle, imaging studies were done to determine response and revealed elimination of nearly all tumor masses (FIG. 1). Four of six target lesions resolved completely, and two additional lesions decreased in size. (Table 2) The subject's symptoms of fever and cough resolved for first time in 9 weeks. Measure of the tumor marker serum LDH was reduced from 899 to 328 (normal). Additionally, EBV, CMV, and HH6 viral load became undetectable. These findings indicate that a shorter, more patient-accessible regimen of the virus-target therapeutic strategy is more efficacious. Also, there remains a continuous need for an oral as opposed to an intravenous HDAC inhibitor. Therefore, the present invention contemplated oral HDAC inhibitors having increased potency as compared to AB.

TABLE 2

Quantification of tumor response evaluated by CT Scan. Tumor dimensions in cm.

| Location | Pre-Treatment | | Post-Treatment | |
|---|---|---|---|---|
|  | Dimension 1 | Dimension 2 | Dimension 1 | Dimension 2 |
| R. Upper lobe | 0.7 | 0.7 | None | None |
| R. Mid Lobe | 1.1 | 1.1 | None | None |
| R. Lower Lobe | 1.4 | 0.8 | 0.8 | 0.6 |
| L. Upper Lobe | 0.9 | 0.8 | None | None |
| L. Lower Lobe | 0.9 | 0.6 | 0.6 | 0.5 |
| Lingular | 0.9 | 0.7 | None | None |
| Hepatic Seg. 6 | 1.1 | 1.1 | None | None |
| Hepatic Seg. 8 | 1.0 | 0.7 | None | None |
| L. Ant. Abd. Wall | 1.1 | 1.9 | None | None |
| R. Ant. Abd. Wall | 0.9 | 0.5 | 0.9 | 0.5 |

Example 3: Analysis of Efficacy of the Herpes Anti-Virals

There are 12 mammalian HDACs, and any one of which might be required for repression of the TK or EBV-PK gene during latency in tumors. HDAC isozyme-specific siRNAs were used to knockdown individual HDACs in tumor lines expressing latent EBV to determine which one of them induces reactivation of TK from latency, rendering it susceptible to anti-virals.

The EBV-positive B lymphoma cell line P3HR1 was used throughout these assays. The P3HR1 cell line was originally derived from Burkitt's lymphoma patient. EBV maintains a latent state of replication in this cell line. Cells were maintained in RPMI 1640 with 10% fetal bovine serum containing 100 U penicillin per ml and 100 µg streptomycin per ml. The HDAC inhibitors used were from five different classes: a) short chain fatty acids, b) hydroxamic acids, c) benzamides, d) cyclic tetrapeptides, and e) largazoles.

To measure the relative level of TK mRNA in various total RNA preparations, reverse transcription and quantitative PCR using real time PCR technology was used. Five micrograms of total RNA was reverse-transcribed using random hexamer primers and Superscript III cDNA synthesis kit (Invitrogen). The cDNA was diluted to a final volume of 60 µl with sterile water, 8 µl of which was then used in each real time PCR reaction in an ABI 7500 Sequencher using SYBR-Green technology. Primers used for the amplification of TK were EBV-TK1-F: 5'-AGATGACGACGGCCTCTACCA-3' (SEQ ID NO: 1); EBV-TK1-R: 5'-CCTCCTTCTGTGCACGAAGT-3' (SEQ ID NO: 2). The ß-actin mRNA levels in those samples were determined similarly using ß-actin-specific primers Actin/hu-F: 5'-GCTCGTCGTCGACAACGGCTC-3' (SEQ ID NO: 3); Actin/hu-R: 5'-CAAACATGATCTGGGTCATCTTCTC-3' (SEQ ID NO: 4). The relative level of TK expression in a sample was calculated following normalization of ß-actin expression level.

Figure 2A:
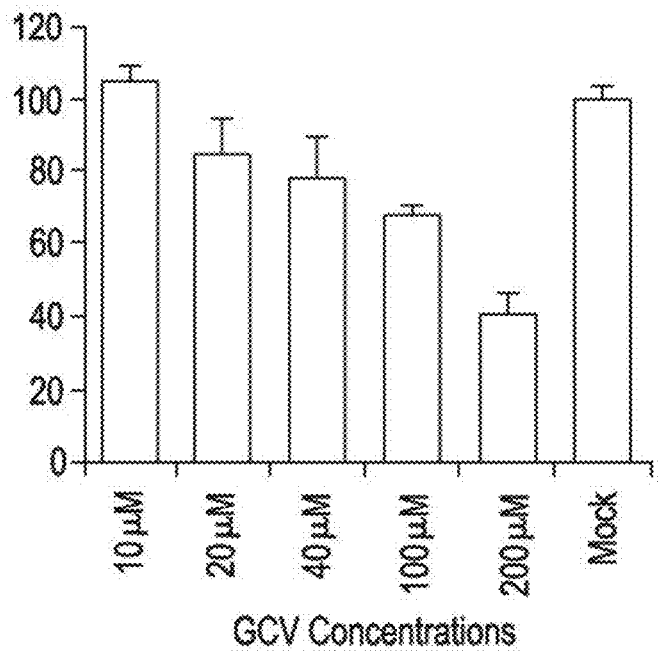
Figure 2B:
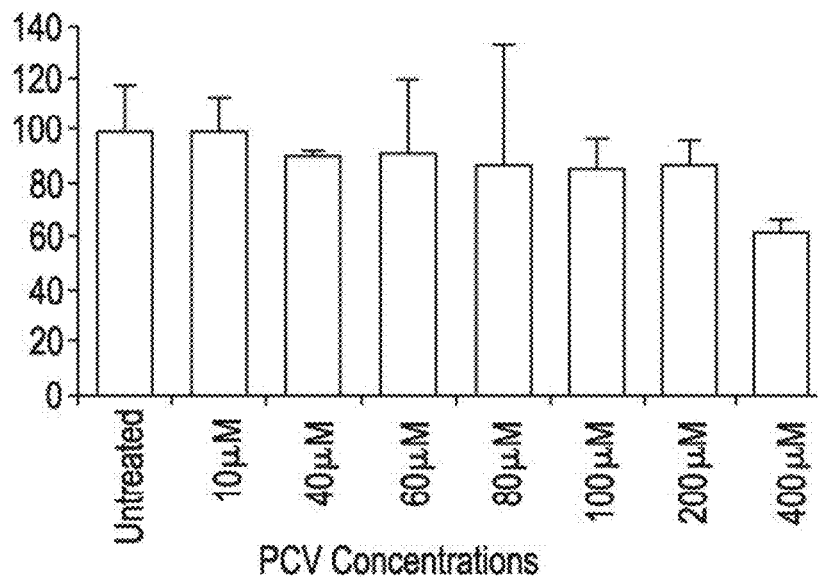

Toxicity assays with two anti-herpesvirus drugs, Gancicovir (GCV) and Penciclovir (PCV), treated to P3HR1 cells alone was conducted as a control. A total of 3×10$^5$ P3HR1 cells were incubated with various concentrations of GCV or PCV and incubated for 6 days. Viable cell counts were measured and toxicity was expressed as percentage of cell growth compared to untreated cells. As shown in FIG. 2A and FIG. 2B, PCV was less toxic to the cells compared to GCV. The effect of 40 µM GCV and PCV in combination treatment approach with 1.0 mM Na-butyrate in P3HR1 cells was compared (FIG. 2C). Inhibition of cell growth with 40 µM PCV (76%) was much less than with 40 µM GCV (38%). This lower level of inhibition of cell growth with PCV did not change significantly when the drug was used at higher concentrations (FIG. 2D).

Example 4: Analysis of Efficacy of HDAC Inhibitors

The induction of lytic phase was assayed in EBV-positive lymphoma cell lines exposed to different HDAC inhibitors (HDACi) for 24-48 hrs, then the expression of EBV TK and other EBV transcripts by RT-PCR analysis was quantified. To determine tumor cytotoxic activity of the combination of HDACi and GCV, EBV+ lymphoma cells were exposed to a range of concentrations of HDAC inhibitors and ganciclovir (GCV) for 3 days and then to GCV alone for another 3 days. Efficacy of a particular HDAC inhibitor in the combination treatment approach was then determined by enumerating living cells. A general experimental protocol is described below.

Cells

The EBV-positive B lymphoma cell line P3HR1 was used in the study. The P3HR1 cell line was originally derived from Burkitt's lymphoma patient. EBV maintains a latent state of replication in this cell line. These cells were maintained in RPMI 1640 with 10% fetal bovine serum containing 100 U penicillin per ml and 100 µg streptomycin per ml.

Study Agent

Various HDAC inhibitors were evaluated in this study. As a positive control, the Short Chain Fatty Acid butyrate, an established inducer of EBV-TK was used. Ganciclovir (GCV) was used as the anti-viral drug.

Titration of HDAC Inhibitors on P3HR1 Cells:

Concentrations of HDAC inhibitors, which do not significantly affect the viability or proliferation of P3HR1 cells in culture were established.

Drug Sensitivity Assay

To test the sensitivity of EBV-positive lymphoma cells towards HDAC inhibitors, P3HR1 cells were treated with HDAC inhibitors in the presence of one anti-viral drug. At the end of the assay, the efficacy of the HDAC inhibitors was assessed by measuring the inhibition of cell growth compared to untreated cells.

Healthy, actively-growing P3HR1 cells were harvested and resuspended in fresh growth media. Cells were seeded in wells. Appropriate dilutions of HDAC inhibitors were added to certain wells, some of which received an anti-viral drug (such as GCV at 50 µM concentration). At 72 hrs, 800 µl of culture fluid was removed from each well. Wells were then refed with 1.0 ml fresh growth media without HDAC inhibitors. Fresh GCV solution was added to the wells that originally received GCV at the same initial concentration. On day 6, cell morphology was observed under microscope and viable cell counts in each individual wells were determined by trypan blue dye exclusion method using an automated cell counter (Countess, Invitrogen).

Thymidine Kinase Expression Assay

A Thymidine Kinase (TK) was used to determine if HDAC inhibitors induced TK expression in EBV-infected lymphoma cells.

P3HR1 cells were seeded in 60 mm plates containing 3×106 cells in 3 ml of fresh growth media. Appropriate concentrations of HDAC inhibitors were added to the plate and cells were incubated in the presence of HDAC inhibitors for 6 h, 24 h, 48 h, or as needed. Cells were harvested by centrifugation and washed once in cold PBS. Total cellular RNA was then extracted. To measure the relative level of TK mRNA in various total RNA preparations, reverse transcription and quantitative PCR using real time PCR analysis were used. See, Ghosh, S. K., Forman, L. W., Akinsheye, I., Perrine, S. P., Faller, D. V.: *Short discontinuous sodium butyrate exposure efficiently sensitizes latently EBV infected cells towards nucleoside analogue-mediated growth inhibition*, Blood Cells Mol. Diseases (2007), 38:57-65. The relative level of TK expression in a sample was calculated following normalization of ß-actin expression level.

Results

The HDAC inhibitors had varying levels of synergistic activity with anti-viral agents in killing EBV+ lymphoma cells. The hydroxamic acid LBH589, the benzamide MS275, and synthetic largazole derivatives were $10^4$ to $10^5$-times more potent in killing EBV+ lymphoma cells in the presence of GCV, compared to sodium butyrate. The effective concentration of LBH589 was in the range of 50-100 nM, MS275 at 200-500 nM, and Largazole derivatives at 100-200 nM. At these concentrations, the drugs as single agents produced no significant growth inhibitory activity in the tumor cells. LBH589, MS275 and Largazole derivatives also strongly induced EBV-TK expression in the tumor cells. In certain instances, the effectiveness of these HDACi compounds at such low concentrations makes them potentially applicable as sensitizers to anti-viral therapeutics for the treatment of EBV-associated lymphomas and other viral or virally-induced conditions. In some embodiments of the invention, these HDAC inhibitors are used as an alternative therapeutic option, in combination with antivirals, for the treatment of EBV-associated tumors and other viral or virally-induced conditions.

A. Short Chain Fatty Acids

Two SCFA HDAC inhibitors, Na-butyrate (NaB) and valproic acid (VA) were tested.

Figure 3A:
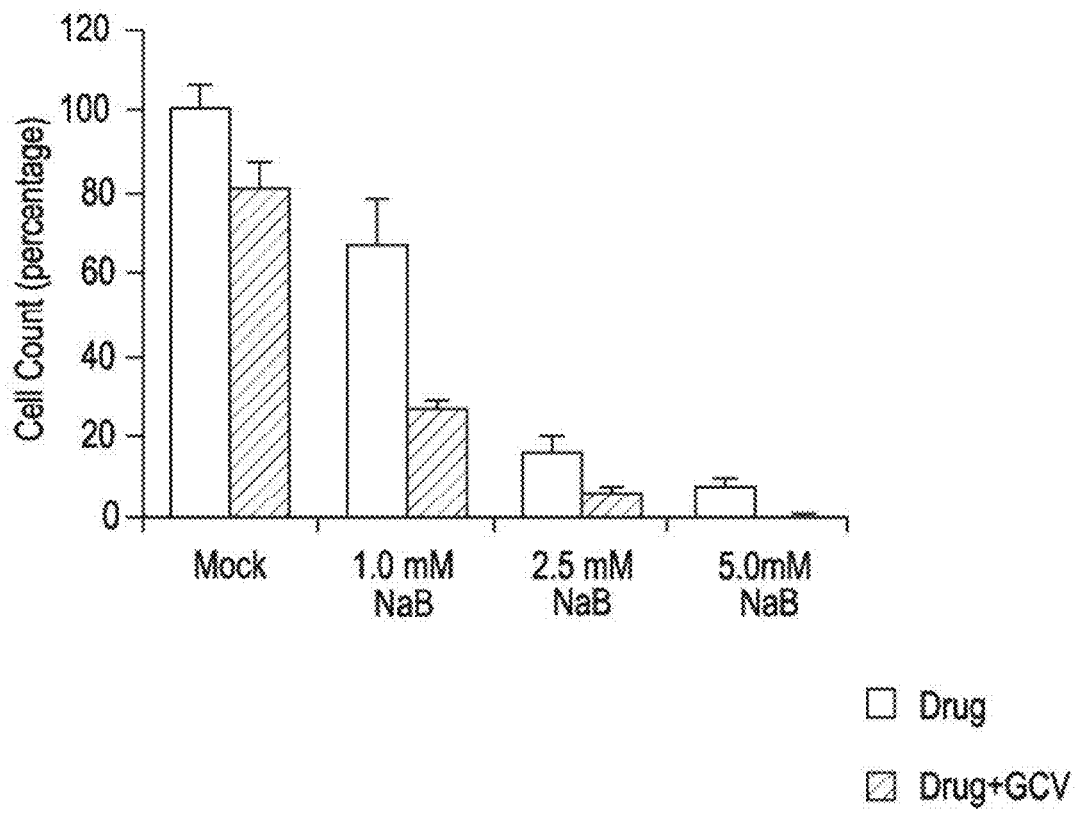
FIGS. 3A-3C illustrate results from analysis of efficacy of anti-virals using short chain fatty acids as inducing agents.

Sodium Butyrate (NaB):

In a combination treatment approach, NaB+GCV reduced growth of EBV-positive P3HR1 cells significantly (up to 50% more) compared to cells treated with NaB or GCV alone (FIG. 3A). The optimal concentration of NaB for this purpose was found to be 1.0 mM. Responses from 1.0 mM NaB was used as a control for interpreting results in this experiment. At a higher concentration, NaB alone reduces cell growth to a significant degree, and the synergistic effects of GCV are lost at those concentrations of NaB.

Figure 3B:
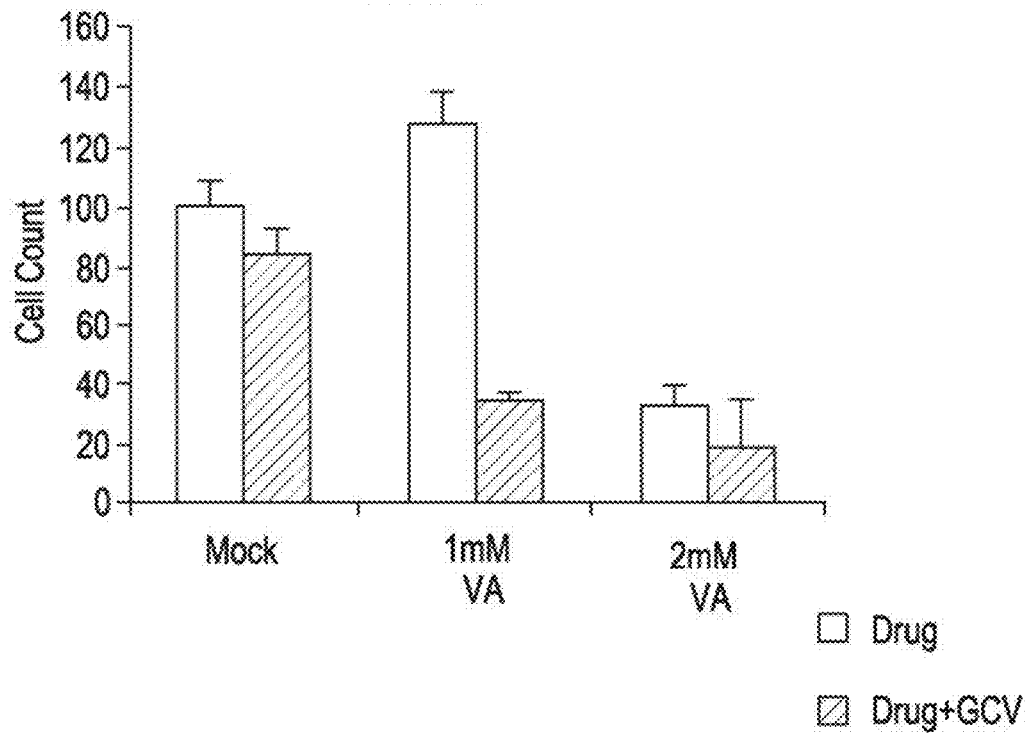
Figure 3C:
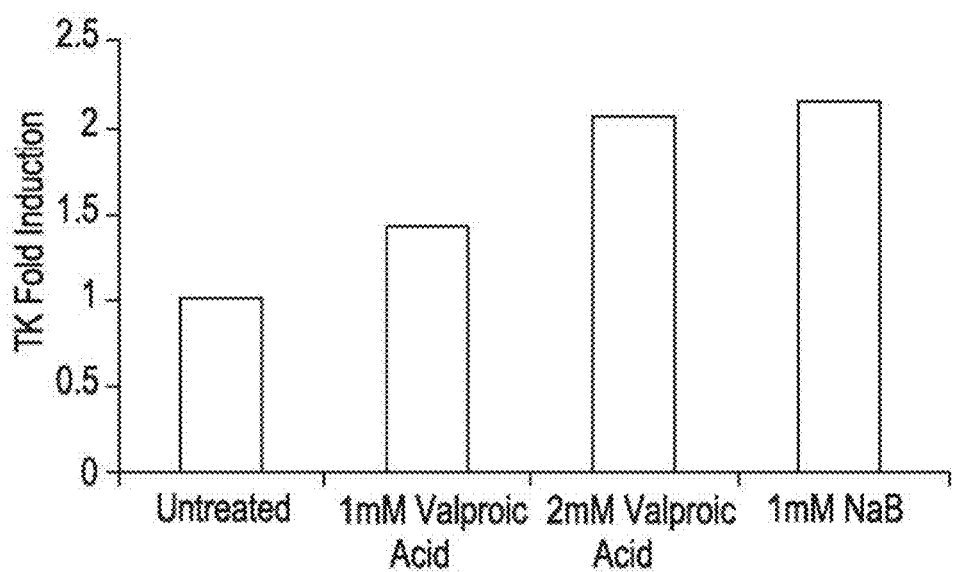

Valproic Acid (VA):

The other HDACi used in this experiment, VA, also had very similar activity (FIG. 3B). Analysis of TK mRNA level by RT and real-time PCR however showed that VA was less efficient than NaB in inducing TK expression (FIG. 3C).

B. Hydroxamic Acids

A total of five different HDAC inhibitors from the hydroxamic acid group were examined as combination therapies. These inhibitors include scriptaid, SAHA, panobinostat-LHB589, belinostat-PXD101, and oxamflatin. All of these HDAC inhibitors can be administered orally via an oral formulation.

Figure 4A:
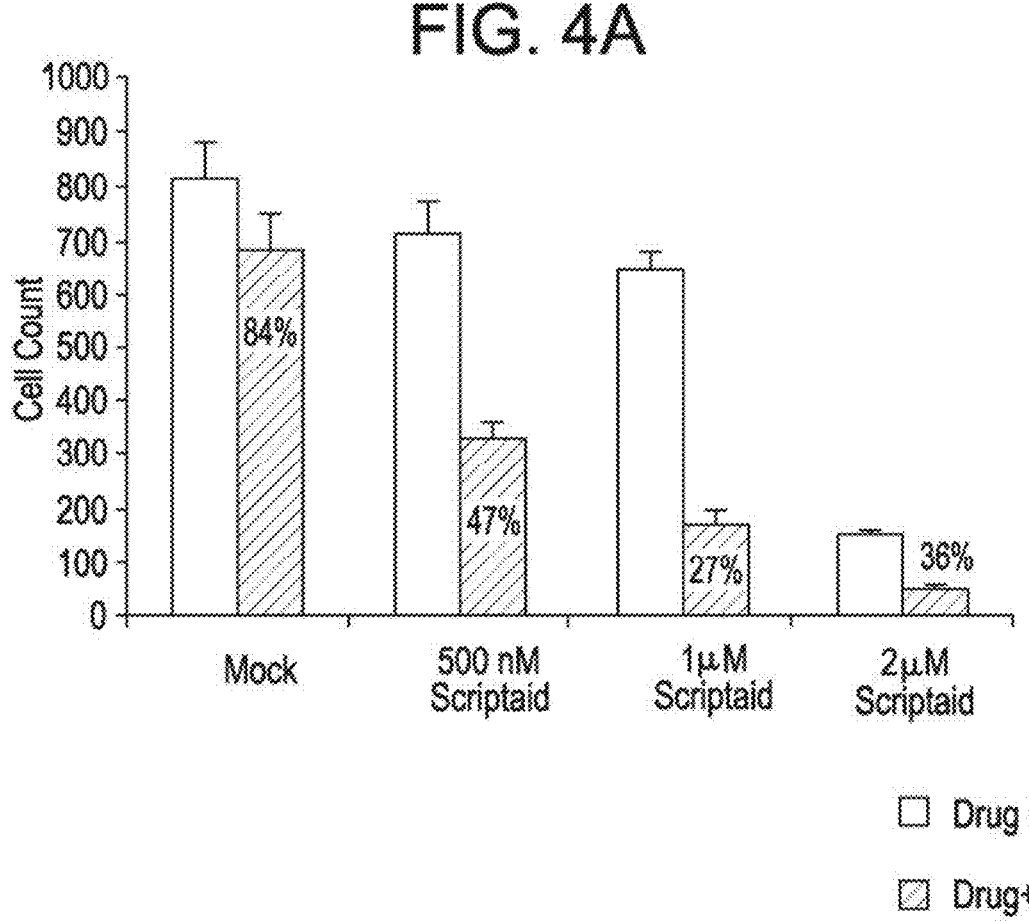
FIGS. 4A-4B illustrate results from analysis of efficacy of anti-virals using hydroxamic acids as inducing agents.
Figure 4B:
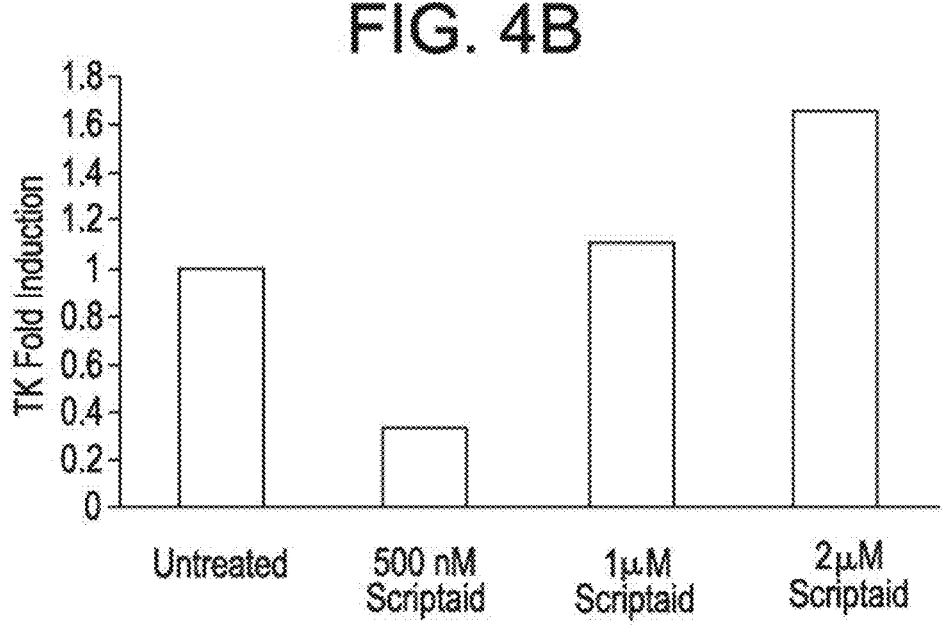

Scriptaid:

Scriptaid showed strong synergistic effect with GCV in reducing cell growth of P3HR1 cells, especially at 500 nM and 1 µM concentrations (FIG. 4A). As shown in the data, in preferred embodiments, an HDAC inhibitor of the invention combined with an antiviral agent can reduce the cell count of EBV infected cells to less than 70%, 60%, 50%, 40%, 30%, 20%, or 10% of cells treated without the HDAC inhibitor or antiviral treatment, or by at least 60%, 50%, 40%, 30%, or 20% from cells treated with an antiviral agent alone.

Figure 5A:
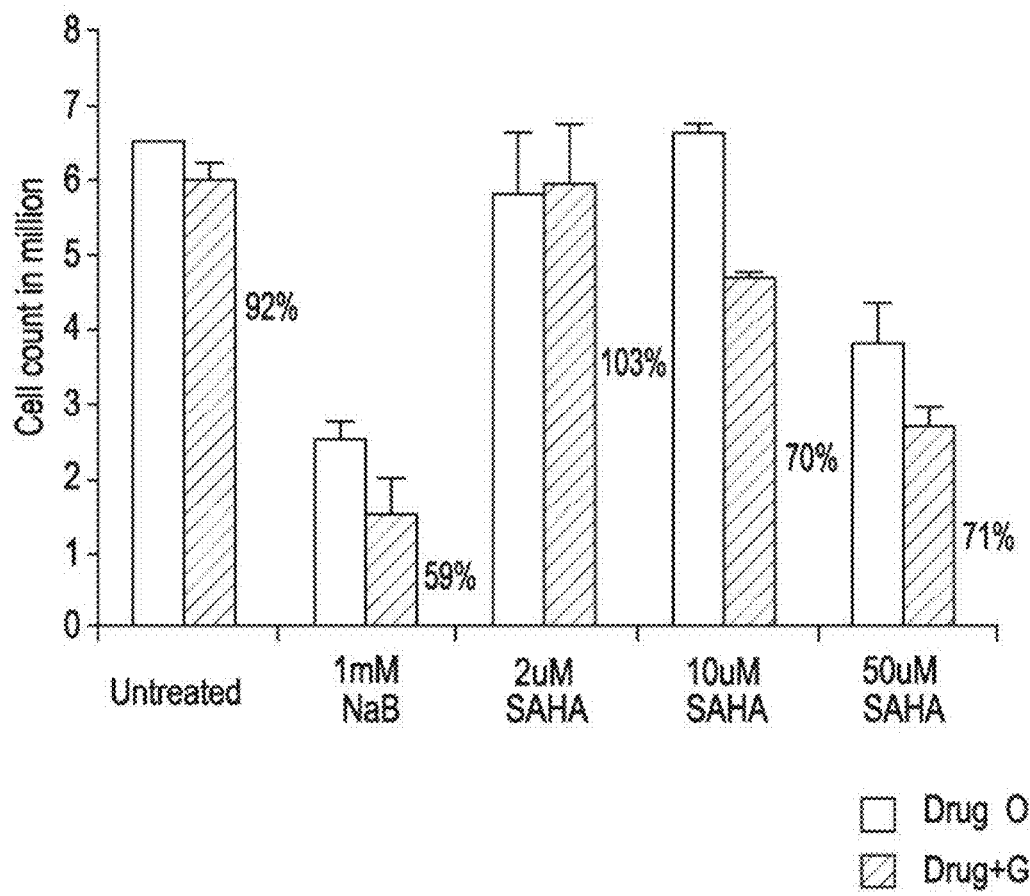
FIGS. 5A-5B illustrate results from analysis of efficacy of anti-virals using SAHA (Vorinostat) as an inducing agent.
Figure 5B:
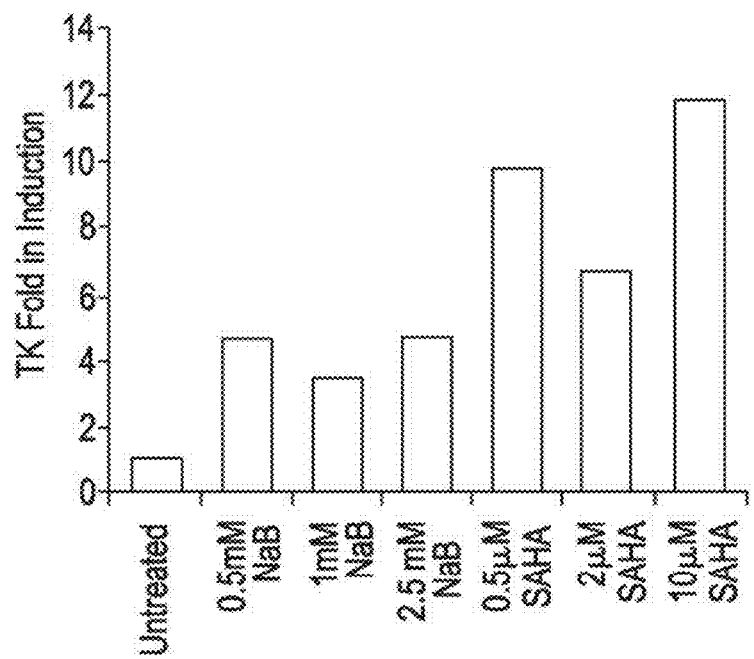

SAHA-Vorinostat:

The combination treatment experiment with SAHA showed that it could induce TK expression at a higher level than that seen with efficient concentrations of butyrate (1.0 mM) (FIG. 5B). As such, the present invention contemplates using an HDAC inhibitor (preferably an oral HDAC inhibitor) to induce EBV kinase expression by at least 2-, 4-, 6-, 8-, or 10-fold, wherein the HDAC inhibitor is administered at a concentration of less than 0.5 mg/kg, 1 mg/kg, 2 mg/kg, 4 mg/kg, 6 mg/kg, 8 mg/kg, or 10 mg/kg.

Figure 6A:
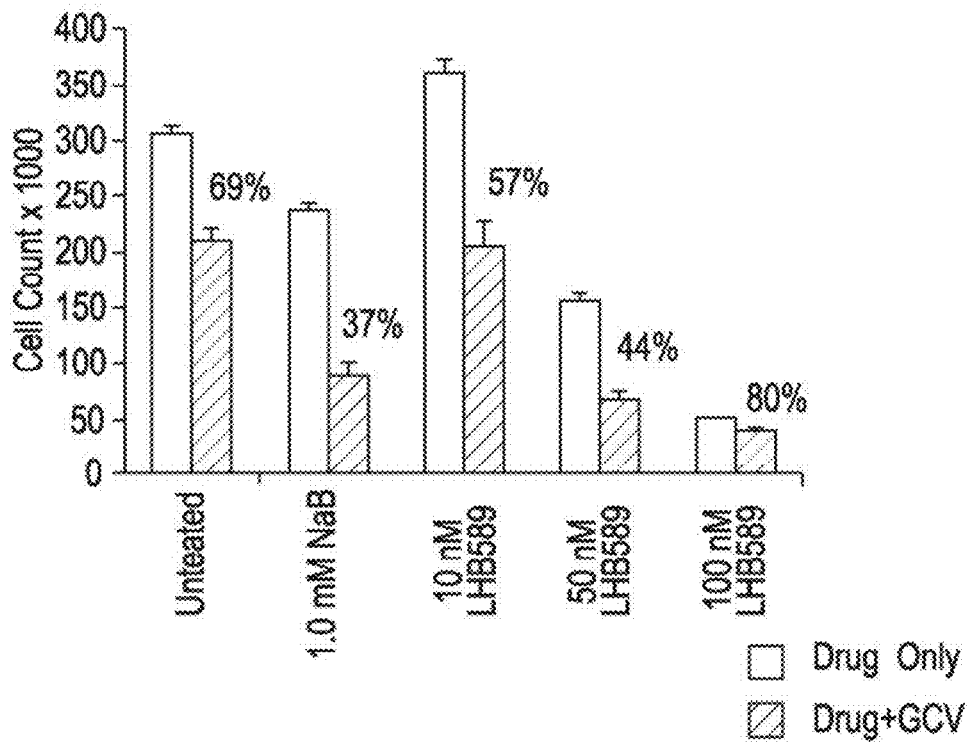
FIGS. 6A-6B illustrate results from analysis of efficacy of anti-virals using LHB589 (Panobinostat) as an inducing agent.
Figure 6B:
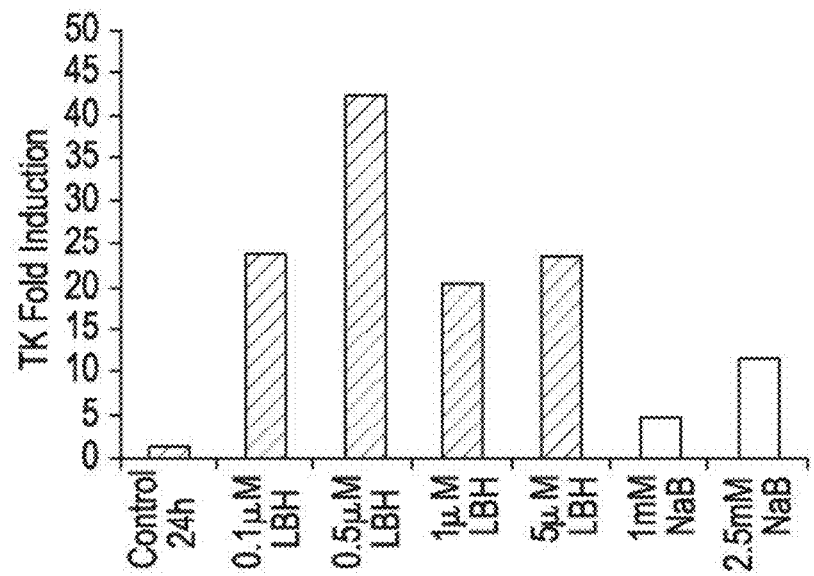

LHB589-Panobinostat:

The growth inhibitory activity of LHB589 at a 50 nM concentration was comparable to that of NaB at 1.0 mM (FIG. 6A). When the cells were treated for 3 days or longer, LHB589 was extremely toxic to the cells at any concentrations 100 nM or above. Although when treated for 24 h only, cells survived well even at a concentration of 5 µM. TK expression level in presence of LHB589 was quite high compared to optimum concentration of NaB (2.5 mM) (FIG. 6B). Thus, in some embodiments, the present invention contemplates a short administration of an oral HDAC inhibitor (e.g., less than 4 days, 3 days, 2 days, 36 h, 24 h, 12 h, or 6 h) in combination with or followed by an antiviral treatment.

Figure 7:
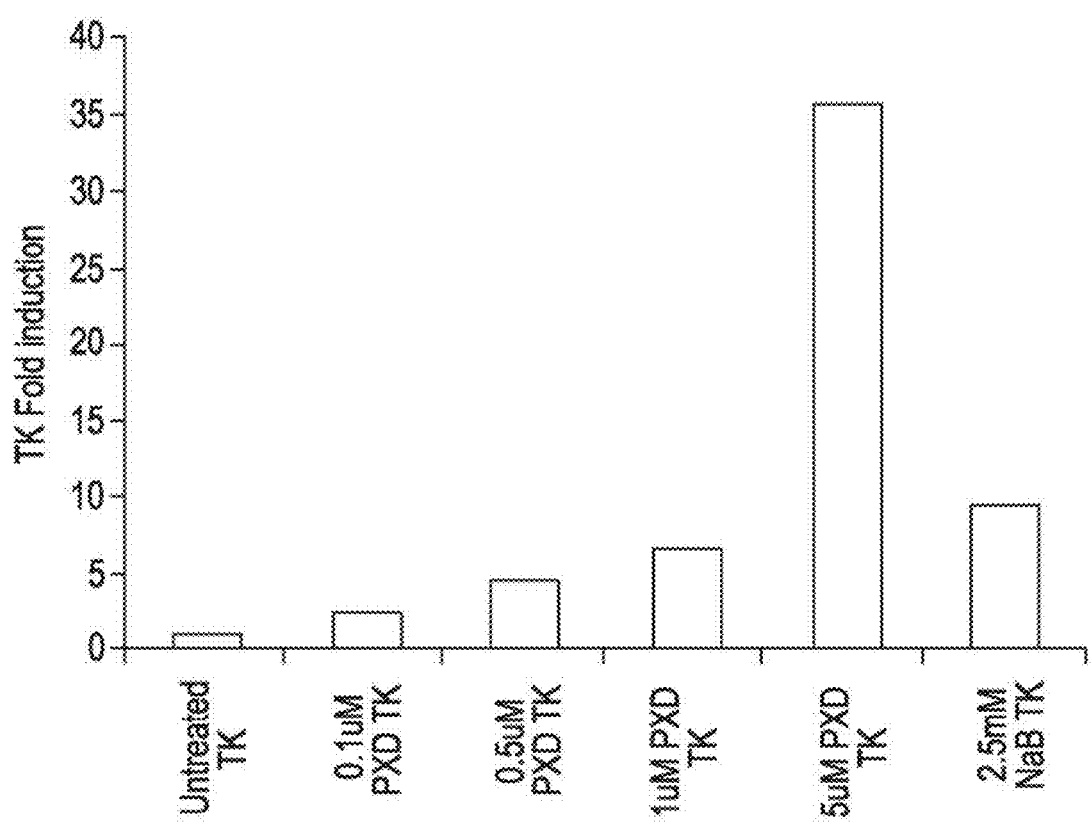
FIG. 7 illustrates results from analysis of efficacy of anti-virals using PXD101, which induced a high level of TK expression at the 5 µM concentration.

PXD101-Belinostat:

PXD101 induced high level of TK expression at the 5 µM concentration. (FIG. 7). Thus, the present invention contemplates using an HDAC inhibitor (preferably an oral HDAC inhibitor) to induce EBV kinase expression by at least 5-, 10-, 15-, 20-, 25-, 30-, or 35-fold.

Figure 8:
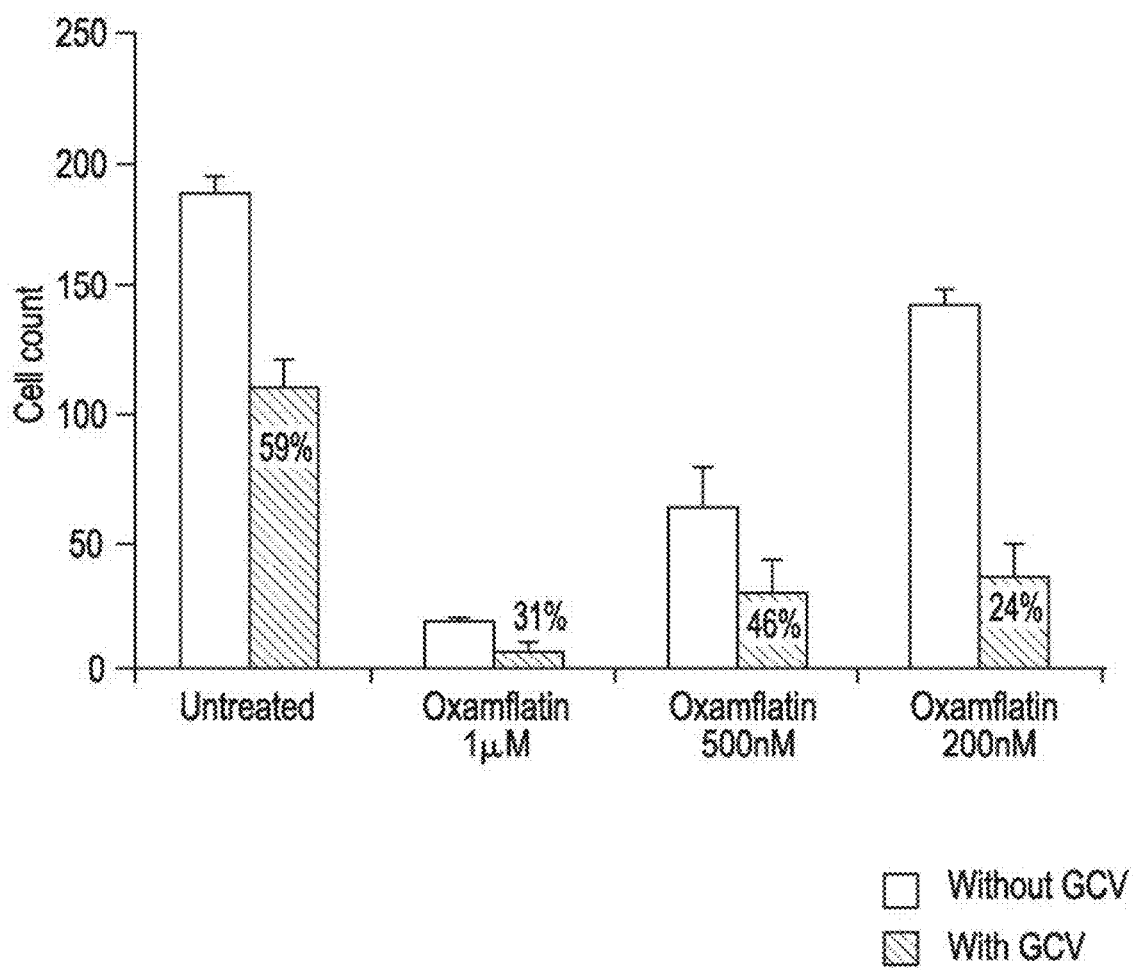
FIG. 8 illustrates results from analysis of efficacy of anti-virals using oxamflatin as an inducing agent.

Oxamflatin:

Oxamflatin showed synergistic activity with GCV towards reducing cell growth. At a 200 nM concentration, the activity level (growth suppression) was more than what typically seen with 1.0 mM NaB (FIG. 8).

As shown in the data, hydroxamic acid HDAC inhibitors synergistically with GCV reduce cell growth of P3HR1 cells. Furthermore, hydroxamic acid HDAC inhibitors induce EBV kinase expression by at least 2-, 5-, 10-, 20-, or 30-fold. In addition, hydroxamic acid HDAC inhibitors in combination with antiviral agents reduce the cell count of EBV infected cells to less than 70%, 60%, 50%, 40%, 30%, 20%, or 10% of cells treated without the HDAC inhibitor or antiviral treatment.

C. Cyclic Tetrapeptide

Figure 9:
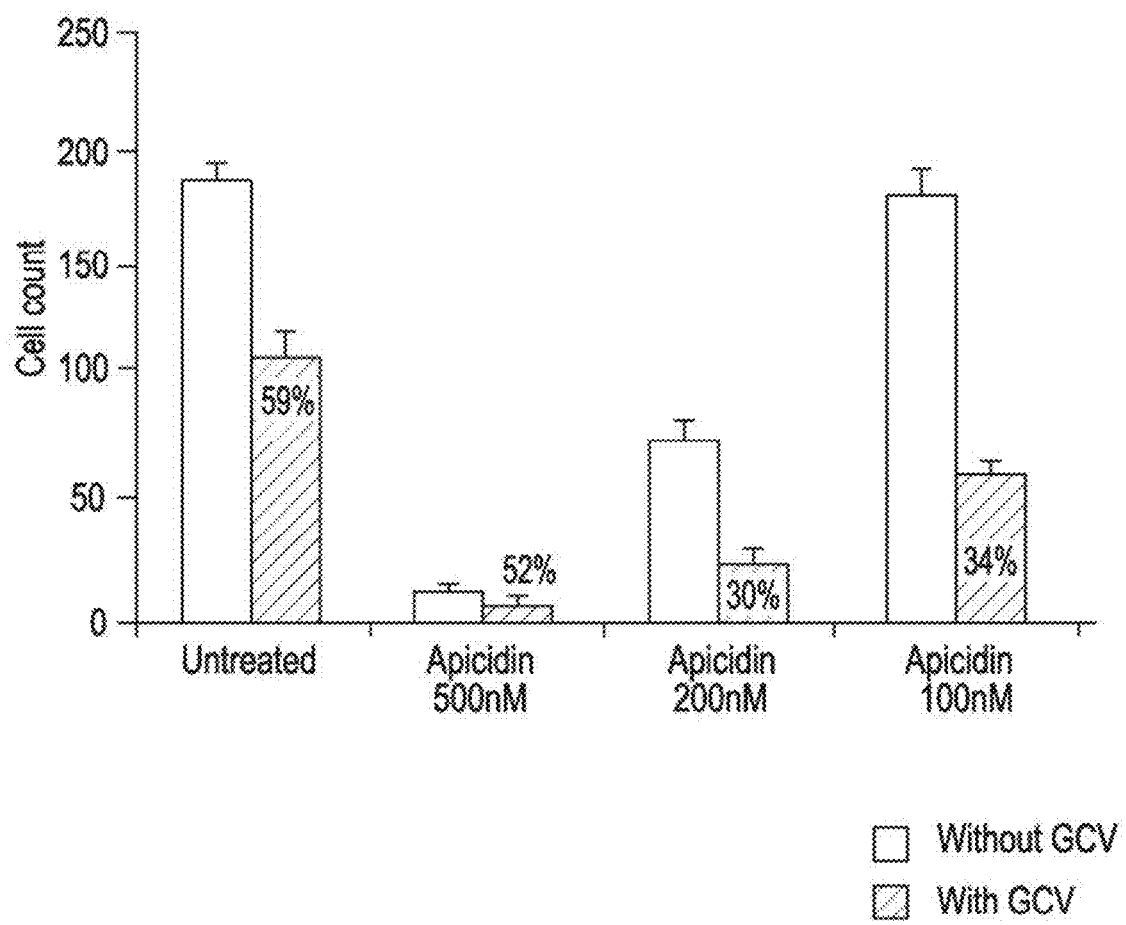
FIG. 9 illustrates results from analysis of efficacy of anti-virals using a cyclic tetrapeptide as an inducing agent.

Apicidin:

The cyclic tetrapeptide group of HDACi examined was apicidin. A toxicity assay with apicidin alone showed that concentrations of apicidin higher than 200 nM was quite toxic to the cells. The combination treatment assay (FIG. 9) showed that at 100 nM and 200 nM concentrations, apicidin reduced cell growth by 40-50% over cells treated with apicidin alone. However, the 200 nM concentration cell growth was significantly retarded without any GCV and a 500 nM concentration was very toxic to the cells.

D. Benzamide

Figure 10A:
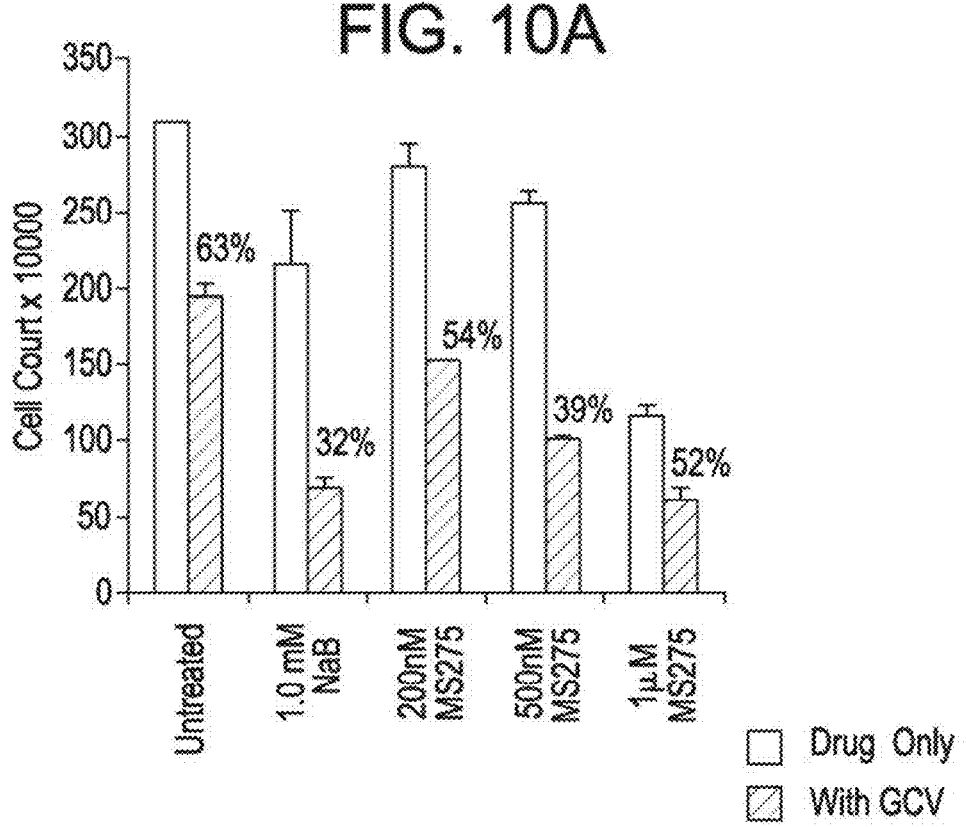
FIGS. 10A-10C illustrate results from analysis of efficacy of anti-virals using a benzamide (MS-275) as an inducing agent.
Figure 10B:
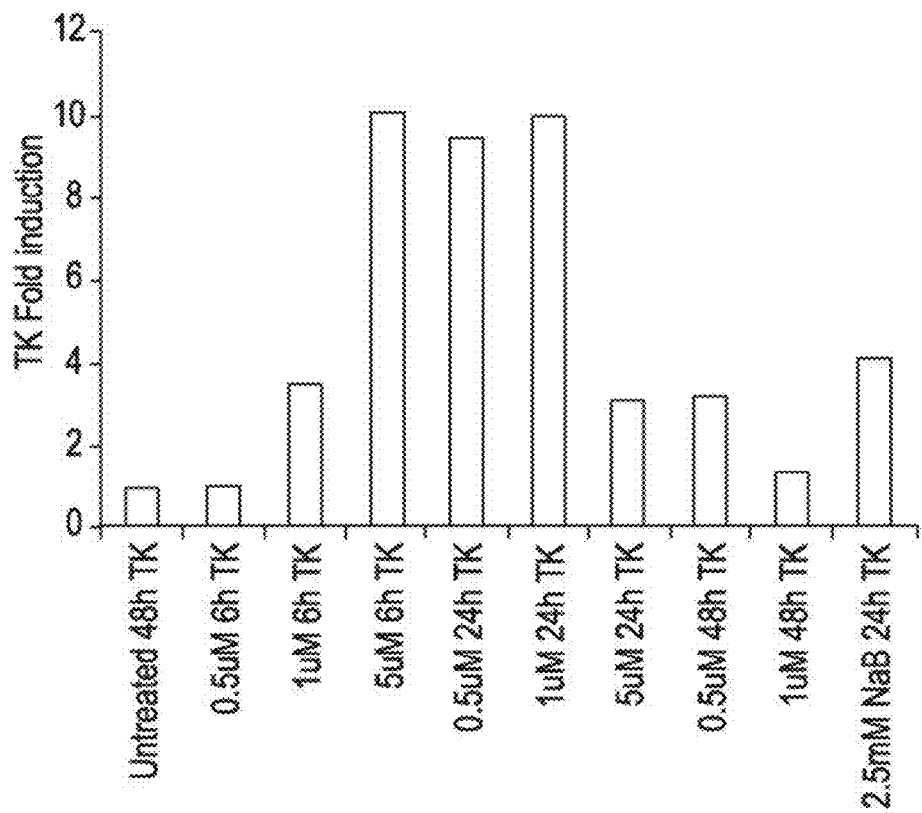
Figure 10C:
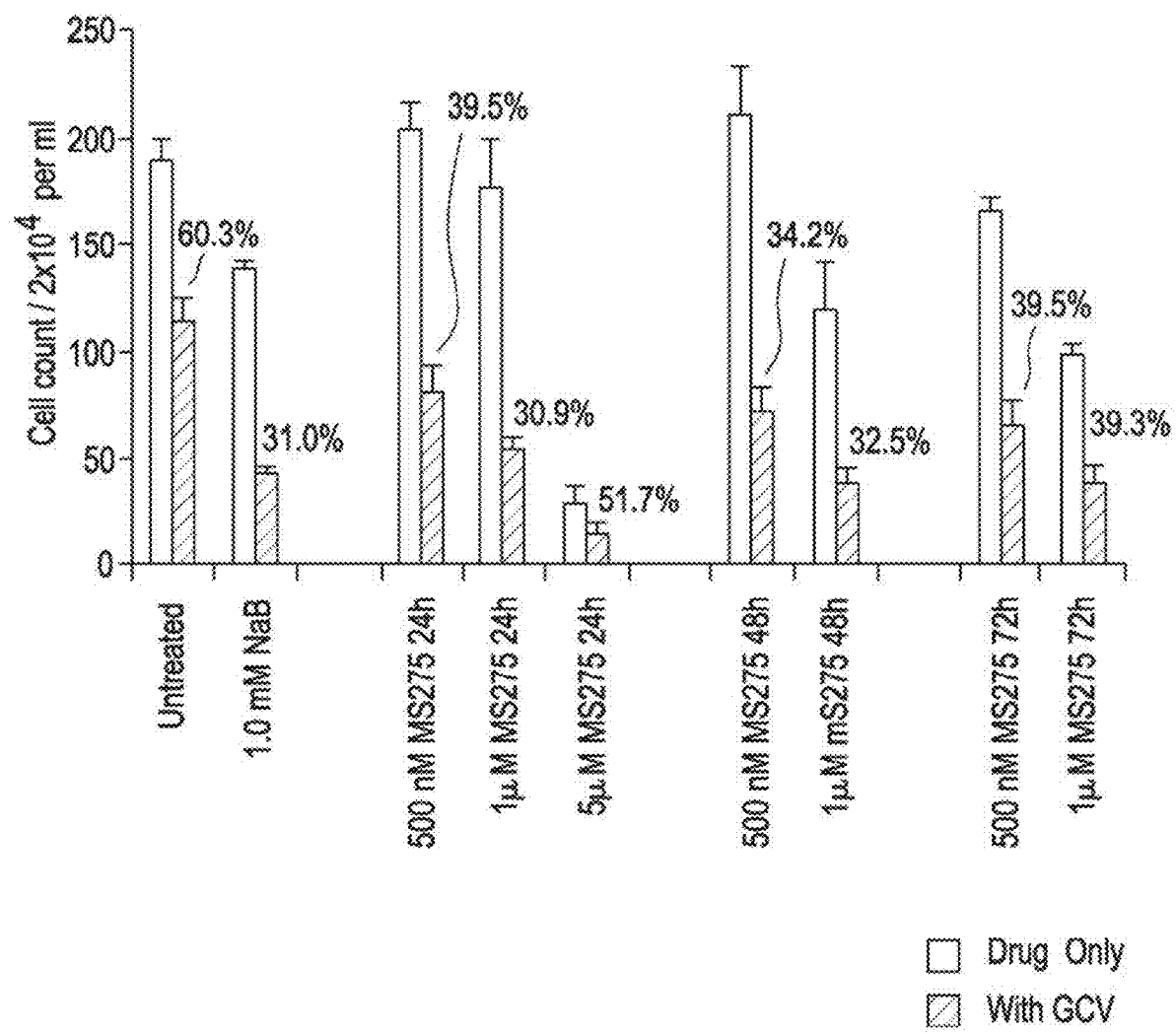
Figure 11B:
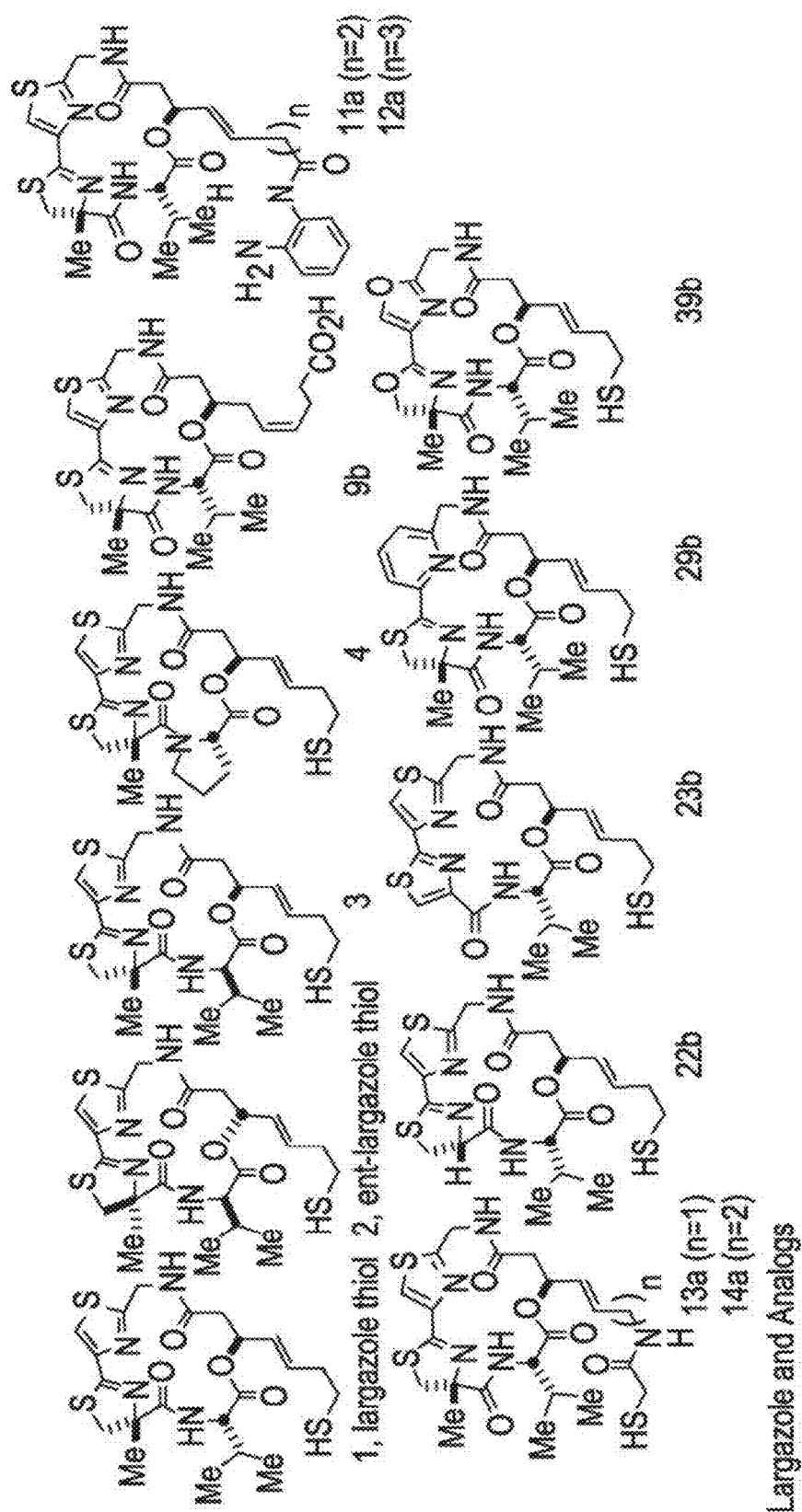

MS-275:

Experiments show that the benzamide class of HDAC inhibitors were extremely potent in sensitizing P3HR1 cells to GCV-mediated effects. As shown below (FIG. 10A) a 500 nM concentration of MS-275 was as efficient as 1.0 mM NaB. Higher concentrations were extremely toxic to the cells. Interestingly, MS-275 also strongly induced TK expression at 500 nM and higher concentrations (FIG. 10B). TK expression was also induced at only 6 hr post treatment. Based on these results, an even shorter exposure to MS-275 was examined to see if it would be sufficient to sensitize P3HR1 cells to GCV-mediated killing. Cells with were treated with MS-275 and GCV for shorter time periods of 24 hr or 48 hr (as opposed to 72 hr) and then further incubated in presence of GCV for up to 6 days, at which time the viable cell counts were enumerated. As shown in FIG. 10C, even at just 24 hr exposure to MS-275 sensitized the cells to GCV-mediated effects as efficiently as a 72 hr continuous treatment. This further demonstrates that MS-275 is very effective sensitizing agent for combination treatment studies.

E. Largazole

Figure 12A:
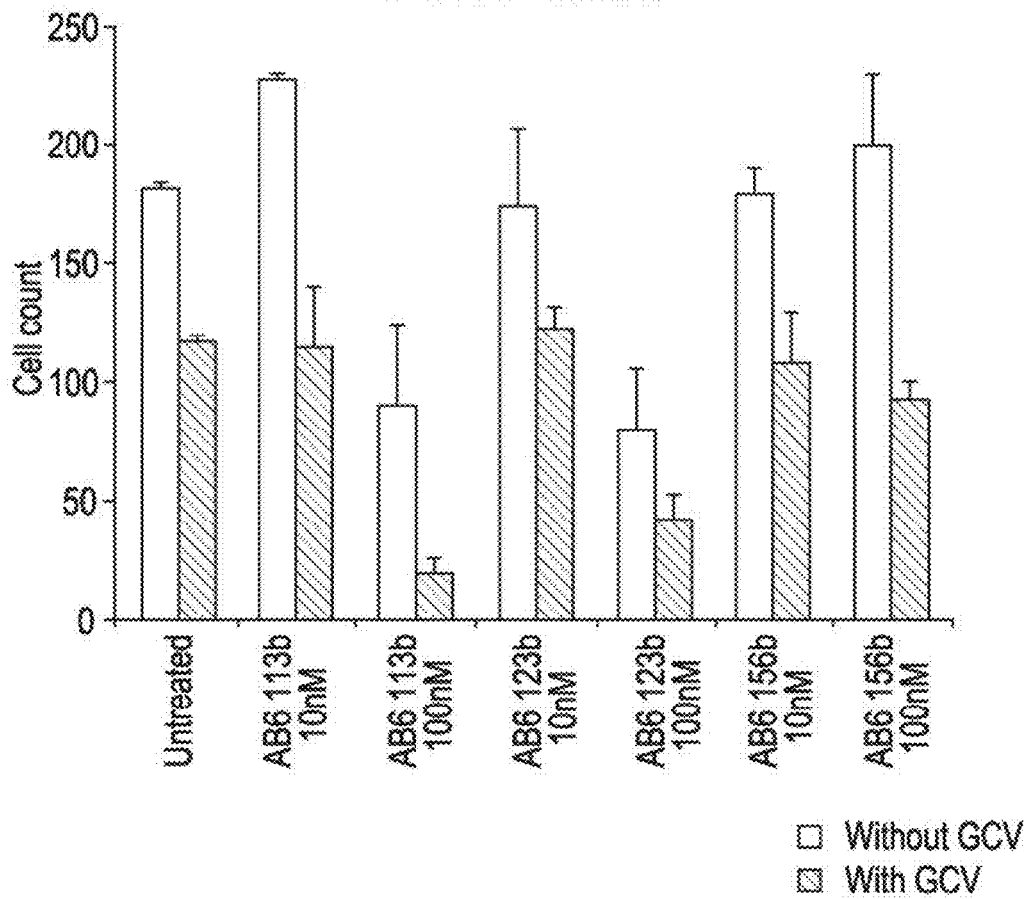
FIGS. 12A-12F illustrate results from analysis of efficacy of anti-virals using largazoles as an inducing agent.
Figure 12B:
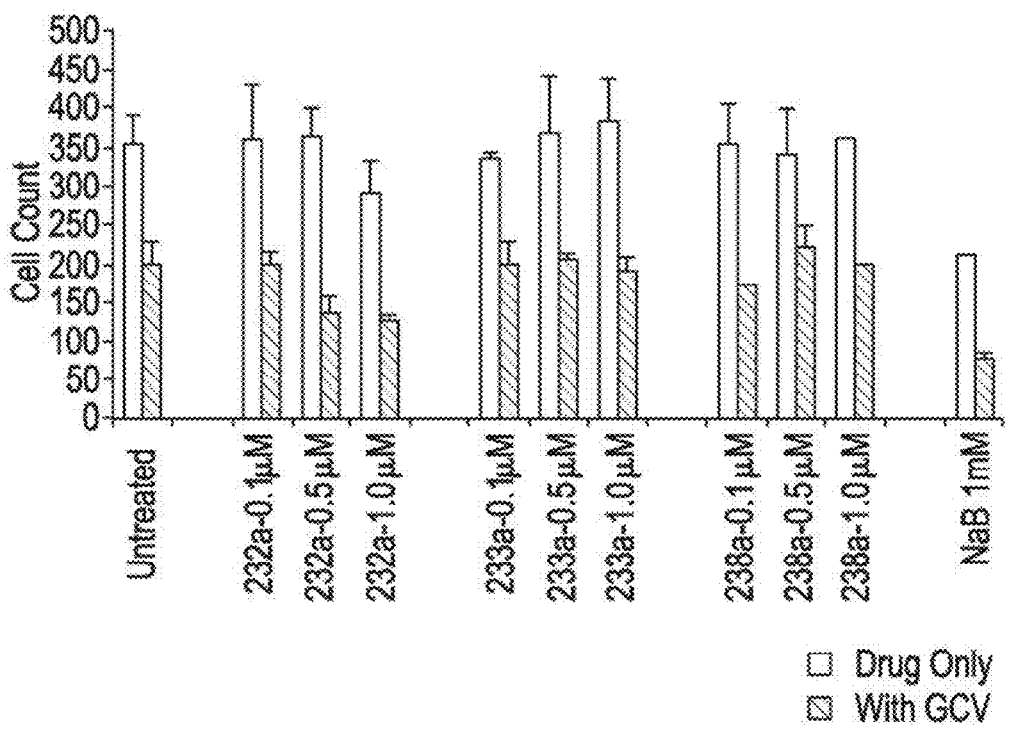
Figure 12C:
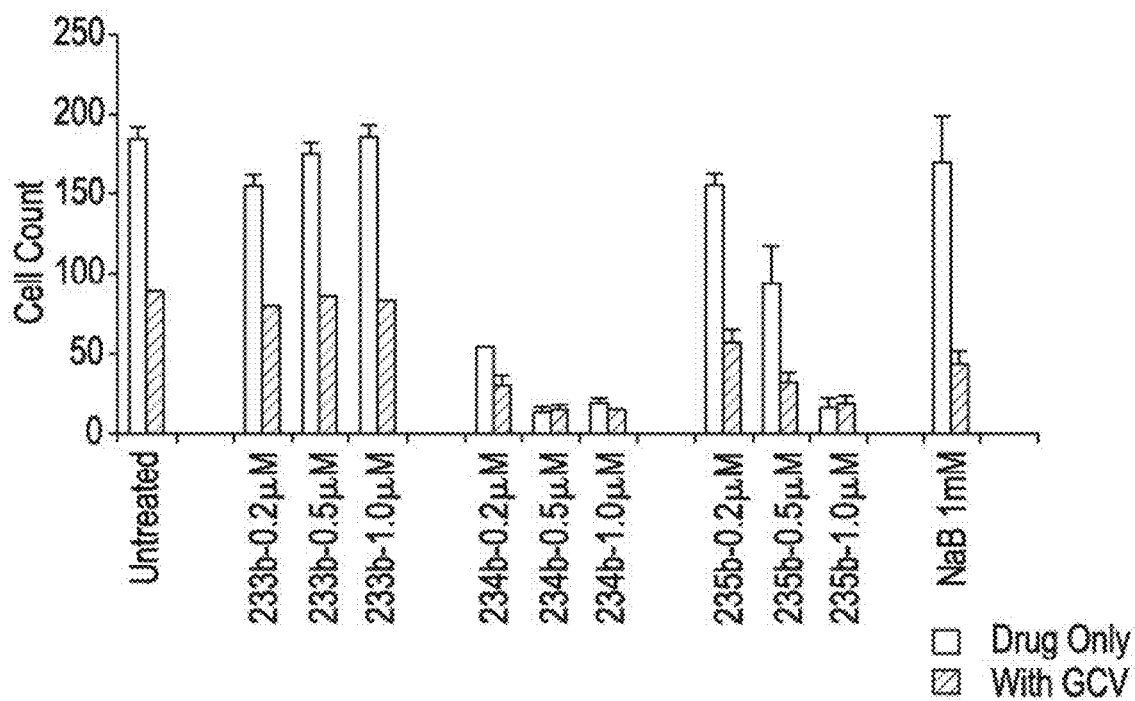
Figure 12D:
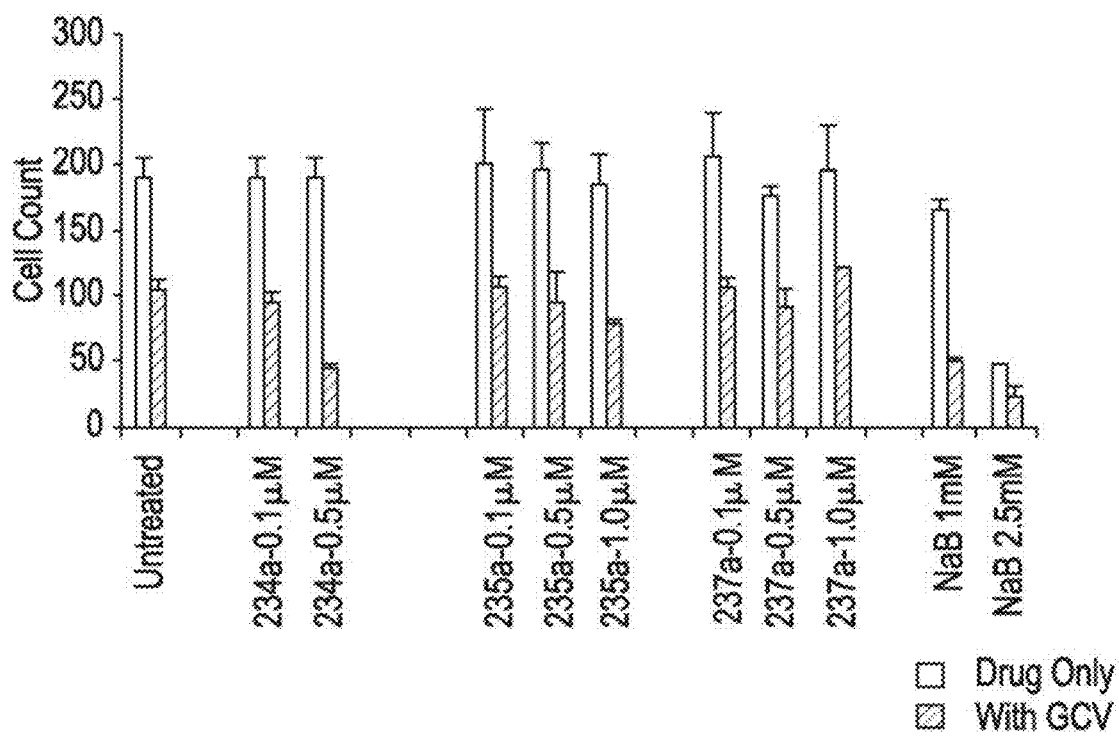
Figure 12E:
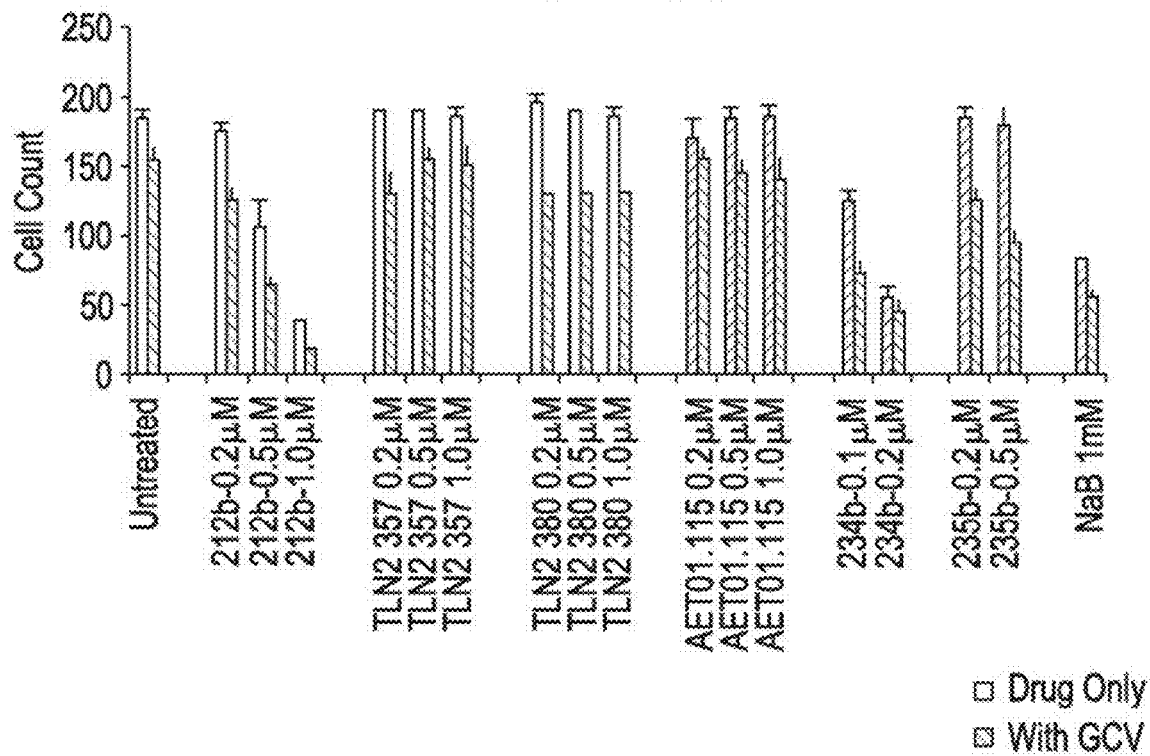
Figure 12F:
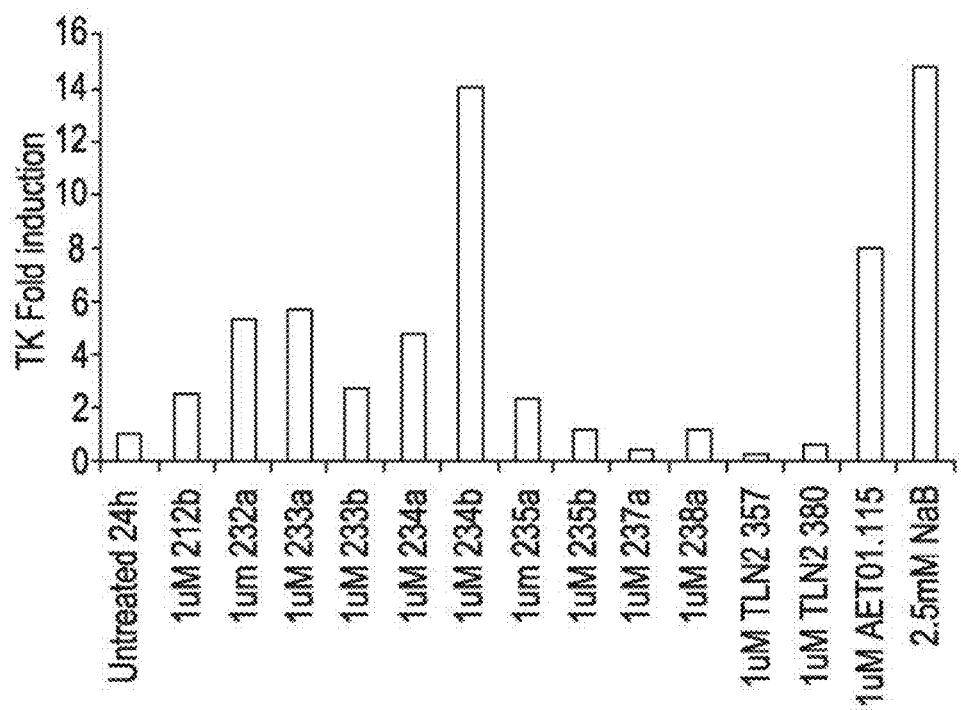

Largazole Derivatives:

Largazole is a member of macrocyclic depsipeptide that was originally isolated from coral reef cyanobacteria. Largazole is a potent HDAC inhibitor with specificity towards HDAC class 1 and 2 only. Additionally, largazole has very low IC 50 and HDAC isozyme specificity. 16 different analogs of the largazole were tested (ab6-113b, ab6-113a, ab6-123a, ab6-123b, ab6-164b, ab6-156b, 232a, 233a, 238a, 233b, 234b, 235b, 234a, 235a, 237a, 212b, TLN1 357, TNL2 380, ART01) for synergistic cell killing activity in combination with GCV (FIGS. 12A, B, C, D, and E). In some embodiments, the HDAC inhibitor and antiviral treatment reduces the number of EBV TK induced cells by at least 10%, 20%, 30%, 40%, 50%, 60%, 70%, 80%, or 90% as compared to untreated cells or cells treated with the antiviral agent only. 13 largazole derivatives were tested both in combination treatment approach and also for their ability to induce EBV TK (FIG. 12F). Several of the largazoles showed potent cell killing activity in combination with GCV. Thus, in some embodiments, an HDAC inhibitor of the invention is one that can induce EBV TK by at least 2-, 4-, 6-, 8-, 10-, 12-, or 14-fold as compared to cells not treated with an HDAC inhibitor. In any of the embodiments herein, the HDAC inhibitor is preferably suitable for oral formulation.

Figure 13:
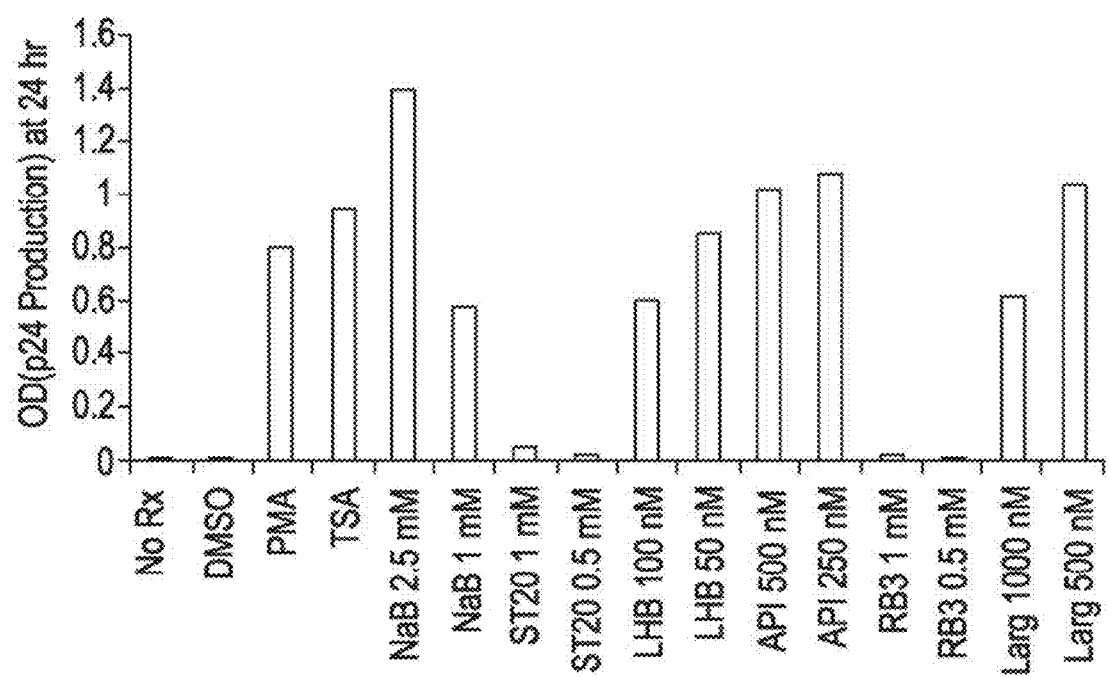
FIG. 13 illustrates results from treatment of an HIV-1-infected monocyte cell line with combination therapy. Viral release (p24 release) was measured through optical density (OD) measurement.
Figure 14:
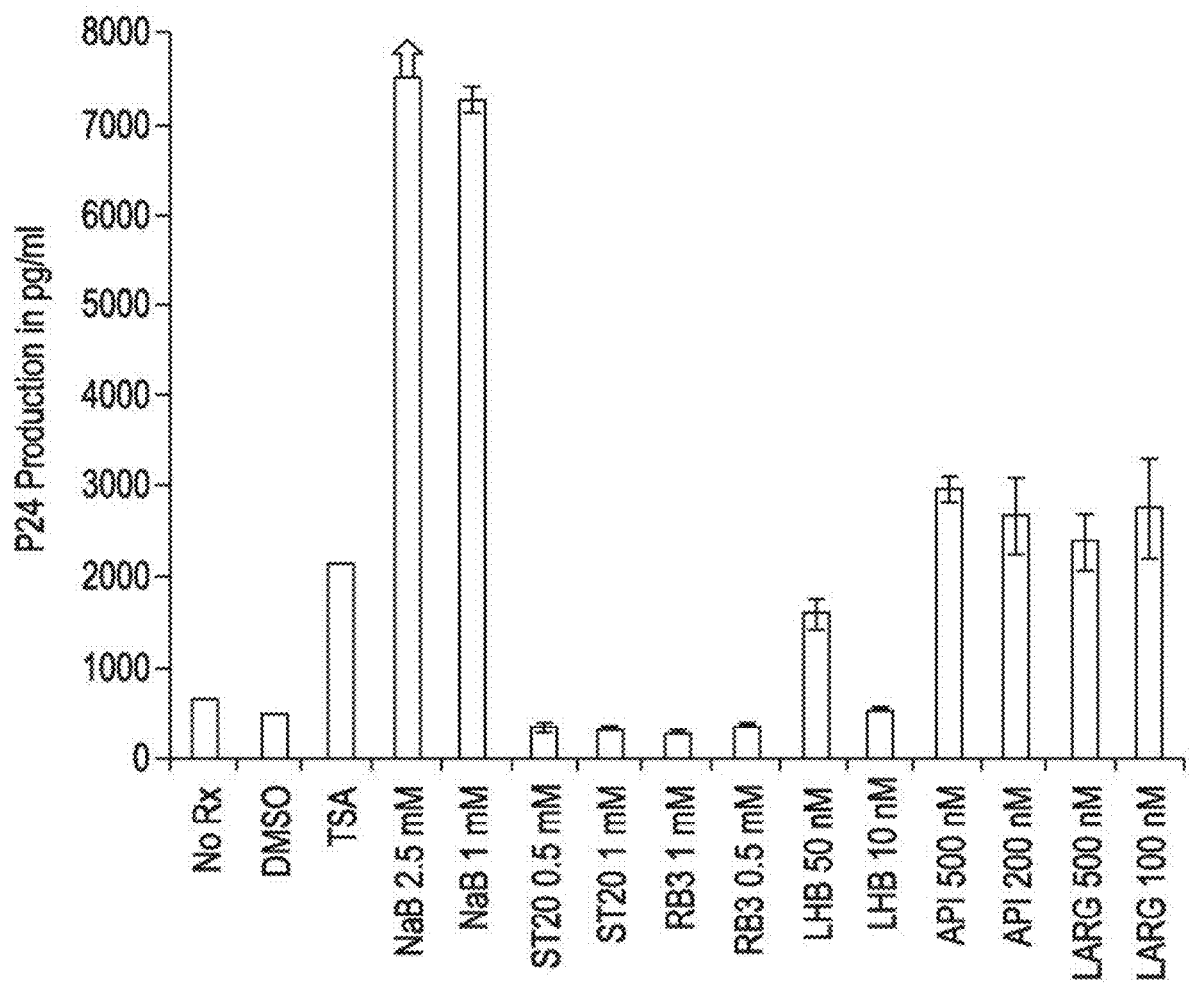
FIG. 14 illustrates results from treatment of an HIV-1-infected monocyte cell line with combination therapy. Viral release (p24 release) was measured through optical density (OD) measurement and then converted into pg of protein.

Example 5: Analysis of Efficacy of Combination Treatment with HIV-Infected Cells Virus production (p24 release) was examined in an HIV-1-infected monocyte line. Cells were treated or not treated with HDAC-inhibitors and other compounds. P24 release expressed as optical density ("OD") (FIG. 13), and then converted to pg of protein (FIG. 14). Arginine butyrate, phorbol myristate acetate (PMA), trichostatin A (TSA), LHB589, apicidin (API) and largazole (LARG) are shown to be active, whereas 2,2-dimethyl butyrate (ST20) and 2-(quinazolin-4-ylamino)butanoic acid (RB3) increased viral production at levels similar to the control of vehicle alone. DMSO was vehicle for some of the compounds tested.

Prophetic Example 1: Treatment of Multiple Sclerosis

Figure 15:
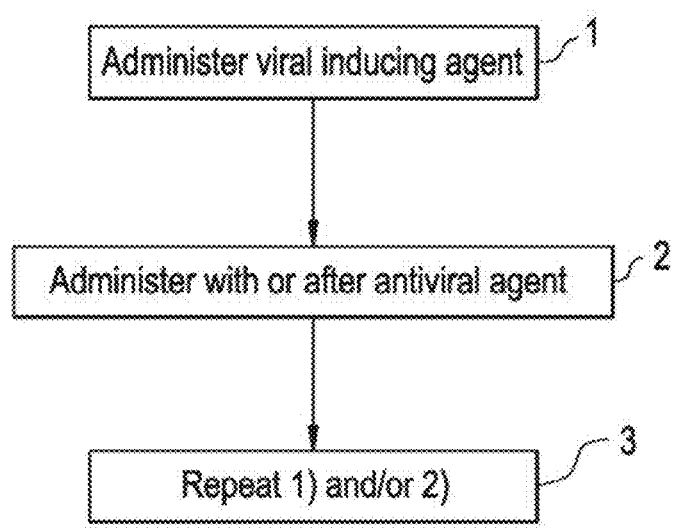
FIG. 15 is a flow diagram of one embodiment of the provided invention.

To treat a subject suspected of having Epstein-Barr virus-induced multiple sclerosis, a health care professional administers to the subject a dose of a pharmaceutical composition comprising a viral inducing agent, the HDAC inhibitor JNJ-26481585. A week later, a health care professional administers to the subject a dose of a pharmaceutical composition comprising an antiviral agent, valganciclovir. A cycle of administration is carried out for a period of a month (FIG. 15). During the period of administration of the viral inducing agent and the antiviral agent, the subject is also administered mitoxantrone to treat the multiple sclerosis. A cycle of HDAC inhibitor and antiviral treatment may be repeated at least 2, 4, 6, 8, 10, or 12 times as needed.

Prophetic Example 2: Treatment of Atherosclerosis

To treat a coronary artery condition patient suspected of having cytomegalovirus-induced atherosclerosis, a health care professional administers a dose of a pharmaceutical composition comprising a viral inducing agent, JNJ-26481585. A week later, a health care professional administers to the subject a dose of a pharmaceutical composition comprising valganciclovir. A cycle of administration is carried out for a period of a month. During the period of administration of the viral inducing agent and the antiviral agent, the subject is also administered rosuvastatin to treat the atherosclerosis.

Prophetic Example 3

A patient either diagnosed with or suspected of having an Epstein Barr Virus (EBV)-associated malignancy such as nasopharyngeal carcinoma, Hodgkin's disease, Burkitt's lymphoma, post-transplantation lymphoproliferative disease, or gastric carcinoma can be treated. A health care professional administers a dose of a pharmaceutical composition comprising JNJ-26481585 and valganciclovir co-formulated for oral administration. The patient is administered a single daily dose in tablet form, where the tablet contains 5 mg of JNJ-26481585 and 1500 mg of timed-release or slow-release valganciclovir. A cycle of administration is carried out for a period of 28 days. During the period of administration, the subject can optionally also be administered an additional chemotherapeutic agent to treat the malignancy.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating and/or preventing a viral or virally-induced condition comprising administering CHR-3996, wherein the CHR-3996 is administered at less than 2 mg/kg per dose, and an antiviral agent, wherein the antiviral agent is selected from the group consisting of valganciclovir, ganciclovir, acyclovir, famciclovir, and combinations thereof, wherein the viral or virally-induced condition is caused by a DNA virus.

2. The method of claim 1, wherein the DNA virus is a herpes virus.

3. The method of claim 1, wherein the DNA virus is an Epstein-Barr virus.

4. The method of claim 1, wherein the DNA virus is a cytomegalovirus.

5. The method of claim 1, wherein the DNA virus is a varicella zoster virus.

6. The method of claim 1, wherein the viral or virally-induced condition is a cancer selected from the group of lymphoma, chronic lymphocytic leukemia, nasopharyngeal carcinoma, gastric cancer, or Kaposi's sarcoma.

7. The method of claim 1, wherein the antiviral agent is valganciclovir.

8. The method of claim 1, wherein the antiviral agent is ganciclovir.

9. The method of claim 1, wherein the antiviral agent is acyclovir.

10. The method of claim 1, wherein the antiviral agent is famciclovir.

11. The method of claim 1, wherein the CHR-3996 and the antiviral agent are administered once daily.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agatgacgac ggcctctacc a                                              21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 2
cctccttctg tgcacgaagt                                               20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctcgtcgtc gacaacggct c                                             21

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caaacatgat ctgggtcatc ttctc                                         25
```